US008617860B2

(12) United States Patent
Schalk

(10) Patent No.: US 8,617,860 B2
(45) Date of Patent: Dec. 31, 2013

(54) METHOD FOR PRODUCING SCLAREOL

(75) Inventor: Michel Schalk, Collonges-Sous-Saleve (FR)

(73) Assignee: Firmenich SA, Geneva (CH)

( * ) Notice: Subject to any disclaimer, the term of this patent is extended or adjusted under 35 U.S.C. 154(b) by 329 days.

(21) Appl. No.: 12/865,298

(22) PCT Filed: Jan. 26, 2009

(86) PCT No.: PCT/EP2009/050816
§ 371 (c)(1),
(2), (4) Date: Jul. 29, 2010

(87) PCT Pub. No.: WO2009/095366
PCT Pub. Date: Aug. 6, 2009

(65) Prior Publication Data
US 2010/0311134 A1 Dec. 9, 2010

(30) Foreign Application Priority Data

Jan. 29, 2008 (EP) .................................... 08101075
Mar. 17, 2008 (EP) .................................... 08102661
Mar. 20, 2008 (EP) .................................... 08102811

(51) Int. Cl.
C12P 7/22 (2006.01)
(52) U.S. Cl.
USPC .......................................................... 435/156
(58) Field of Classification Search
USPC .......................................................... 435/156
See application file for complete search history.

(56) References Cited

U.S. PATENT DOCUMENTS

2011/0041218 A1* 2/2011 Schalk .......................... 800/298

OTHER PUBLICATIONS

Altschul, Stephen F., "Amino Acid Substitution Matrices from an Information Theoretic Perspective" *J. Mol. Biol.*, 219, 555-565 (1991).
Altschul, Stephen F. et al., "Basic Local Alignment Search Tool" *J. Mol. Biol.*, 215, 403-410 (1990).
Banthorpe, Derek V. et al., "Partial Purification of Farnesyl Pyrophosphate: Drimenol Cyclase and Geranylgeranyl Pyrophosphate: Sclareol Cyclase, Using Cell Culture as a Source of Material" *Phytochemistry*, 31(10), 3391-3395 (1992).
Dewick, Paul M., "The biosynthesis of $C_5$-$C_{25}$ terpenoid compounds" *Nat. Prod. Rep.*, 19, 181-222 (2002).
Emanuelsson, Olof et al., "ChloroP, a neural network based method for predicting chloroplast transit peptides and their cleavage sites" *Protein Science*, 8, 978-984 (1999).
Horton, Robert M. et al., "Engineering hybrid genes without the use of restriction enzymes: gene splicing by overlap extension" *Gene*, 77, 61-68 (1989).
Huang, Xiaoqiu "A Contig Assembly Program Based on Sensitive Detection of Fragment Overlaps" *Genomics*, 14, 18-25 (1992).
Huang, Qiulong et al., "Engineering *Escherichia coli* for the synthesis of Tazadiene, a Key Intermediate in the Biosynthesis of Taxol" *Bioorganic & Medicinal Chemistry*, 9, 2237-2242 (2001).
Keller, R. Kennedy et al., "Rapid synthesis of isoprenoid diphosphates and their isolation in one step using either thin layer or flash chromatography" *Journal of Chromatography*, 645, 161-167 (1993).
Margis-Pinheiro, Marcia et al., "Isolation and characterization of *Ds*-tagged rice (*Oryza sativa* L.) GA-responsive dwarf mutant defective in an early step of the gibberellins biosynthesis pathway" *Plant Cell Rep*, 23, 819-833 (2005).
Schardl, Christopher L. et al., "Design and construction of a versatile system for the expression of foreign genes in plants" *Gene.*, 61, 1-11 (1987).
Stemmer, Willem P.C., "DNA shuffling by random fragmentation and reassembly: In vitro recombination for molecular evolution" *Proc. Natl. Acad. Sci. USA*, 91, 10747-10751 (1994).
Tatusova,Tatiana A. et al., "BLAST 2 Sequences, a new tool for comparing protein and nucleotide sequences" *FEMS Microbiology Letters*, 174, 247-250 (1999).
Wendt, K Ulrich et al., "Isoprenoid biosynthesis: manifold chemistry catalyzed by similar enzymes" *Structure*, 6(2), 127-133 (1998).
Xu, Meimei et al., "Functional characterization of the rice kaurene synthase-like gene family" *Phytochemistry*, 68, 312-326 (2007).
XP-002494697, (2005).
XP-002494698, (2000).
Lange, B. Markus et al., "Probing essential oil biosynthesis and secretion by functional evaluation of expressed sequence tags from mint glandular trichomes" *PNAS*, 97(6), 2934-2939 (2000).
Guo, Zhenhua et al., "Biosynthesis of labdenediol and sclareol in cell-free extracts from trichomes of *Nicotiana glutinosa*" *Planta*, 197, 627-632 (1995).
Banthorpe, Derek V. et al., "Accumulation of the Anti-Fungal Diterpene Sclareol by Cell Cultures of *Saliva sclarea* and *Nicotiana glutinosa*" *Phytochemistiy*, 29(7), 2145-2148 (1990).
Nichols, Harold J., "Biosynthesis of Sclareol, β-Sitosterol, and Oleanolic Acid from Mevalonic Acid-2-$C^{14}$" *The Journal of Biological Chemistry*, 237(5), 1481-1484 (1962).
D'Auria, John C et al., "The secondary metabolism of *Arabidopsis thaliana*: growing like a weed" *Current Opinion in Plant Biology*, 8, 308-316 (2005).

* cited by examiner

*Primary Examiner* — Tekchand Saidha
(74) *Attorney, Agent, or Firm* — Scully, Scott, Murphy & Presser, P.C.

(57) ABSTRACT

The present invention provides a method of producing sclareol, the method comprising contacting a particular polypeptide having a sclareol synthase activity with labdenediol diphosphate (LPP). In particular, the method may be carried out in vitro or in vivo to produce sclareol, a very useful compound in the fields of perfumery and flavoring. The present invention also provides the amino acid sequence of the polypeptide used in the method. A nucleic acid derived from *Salvia sclarea* and encoding the polypeptide of the invention, an expression vector containing the nucleic acid, as well as a non-human organism or a cell transformed to harbor the same nucleic acid, are also part of the present invention.

9 Claims, 12 Drawing Sheets labdenediol diphosphate sclareol
(-)-(13R)-14-labdene-8,13-diol (-)-Ambrox geranylgeranyl diphosphate (GGPP)

ent-kaurene ent-cassa-12,15-diene

Figure 3B

```
                490       500       510       520       530       540       550       560
                ....|....|....|....|....|....|....|....|....|....|....|....|....|....|....|....|
                                                                                 -ATDDEVDVGGS-   Contig-33
                                                                       RIAE TSEVT DDEE           Contig-1610-fox2
                LAVEKFHVNQSVYQQELRVYLESWVAEFGLDELKFARVIPLQSLLSALVPLFPAELSDER AENCLT DDEEDGGS       Stemodene synthase 570       580       590       600       610       620       630       640
                ....|....|....|....|....|....|....|....|....|....|....|....|....|....|....|....|
                MEEMVNEVALIDEWDNHGEIGFCSMNVEIMFMAIYNTTKRMCAKAALVQNRCVMDHIAKQWQVMVRAMKTEAEWAASRH       Stemodene synthase 650       660       670       680       690       700       710       720
                ....|....|....|....|....|....|....|....|....|....|....|....|....|....|....|....|
                IPATMEEVMSVGEPSEALGEIVPLSAYLLGEELPEEAVRSPEVGQLIRHASAVGRLLMDVMTVEKEVLTWTPMSVLLQAL       Stemodene synthase 730       740       750       760       770       780       790       800
                ....|....|....|....|....|....|....|....|....|....|....|....|....|....|....|....|
                                                              EPC ELEW                           Contig-224
                AAARGGGESPTPPSPACAEAARGEVRRAIQASWRDLHRLVFRDDEGSS ERC ELEW STAKVANVFYQEVDGVTPKAM       Stemodene synthase 810
                ....|....|..
                RGMANAVILDPLHLQQ                                                                  Stemodene synthase
```

METHOD FOR PRODUCING SCLAREOL

RELATED APPLICATION

This application is a '371 application of PCT Application No. PCT/EP2009/050816, filed Jan. 26, 2009.

TECHNICAL FIELD

The present invention provides a method of producing sclareol, said method comprising contacting a particular polypeptide having a sclareol synthase activity with labdenediol diphosphate (LPP). In particular, said method may be carried out in vitro or in vivo to produce sclareol, a very useful compound in the fields of perfumery and flavoring. The present invention also provides the amino acid sequence of the polypeptide used in the method. A nucleic acid derived from *Salvia sclarea* and encoding the polypeptide of the invention, an expression vector containing said nucleic acid, as well as a non-human organism or a cell transformed to harbor the same nucleic acid, are also part of the present invention.

PRIOR ART

Sclareol is one member of the terpenoids or terpenes family, comprising a high number of natural products. Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Diterpenes, for example, are widely found in the plant kingdom and over 2500 diterpene structures have been described (Connolly and Hill, Dictionary of terpenoids, 1991, Chapman & Hall, London). Terpene molecules have been of interest for thousands of years because of their flavor and fragrance properties and their cosmetic, medicinal and antimicrobial effects. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. These enzymes convert a precursor in one or more terpene products. Most of the time, the precursor is an acyclic terpene precursor and, in particular, most diterpene synthases catalyze the cyclization of the acyclic precursor geranylgeranyl pyrophosphate. Nevertheless, in some special cases, terpene synthases catalyze the transformation of an already cyclic molecule into one or more terpene products.

Two types of cyclization mechanisms occur in nature and are related to two types of diterpene synthases which can be classified into class I and class II diterpene synthases (Wendt and Schulz, 1998, Structure. 6(2):127-33). For some diterpenes, the cyclization mechanism is similar to those of monoterpenes and sesquiterpenes as it is initiated by the ionization of the diphosphate ester function of GGPP, followed by the reaction of the resulting carbocation with an internal double bond. The diterpene synthases catalysing this type of cyclization are class I diterpene synthases. The second mode of cyclization in the biosynthesis of diterpenes, catalyzed by class II diterpene synthases, is initiated by the protonation of the terminal double bond of GGPP and leads, after internal rearrangement and proton elimination, to a cyclic diterpene diphosphate intermediate.

Genes and cDNAs encoding diterpene synthases from each of the two classes have been cloned and the recombinant enzymes characterized. The availability of genes encoding different types of diterpene synthases provides information on the primary structures of the enzymes. Some amino acid motifs are conserved in diterpene synthases and are related to either the protonation or the ionization dependent cyclization. A DDxxD motif is found in several class I diterpene synthases. Said motif is probably involved in binding and ionization of the diphosphate moiety. In class II synthases, a conserved DxDD motif is found, in which the second aspartate residue is involved as proton donor.

Sclareol is a naturally occurring diterpene molecule extensively used as starting material for the synthesis of fragrance molecules with ambergris notes. These syntheses were developed to provide an alternative to ambergris, a waxy substance secreted by the intestines of sperm whale. Ambergris is highly appreciated for its pleasant odor and has been historically used as a perfume ingredient. Due to its high price and the increasing demand for ambergris, and particularly due to the protection of the whale species, chemical synthesis of ambergris constituents and molecules with ambergris character have been developed. Amongst these molecules, Ambrox® (registered trademark of Firmenich SA, Switzerland) is the most largely appreciated substitute for Ambergris. The most widely used starting material for the synthesis of Ambrox® is the diterpene-diol sclareol.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years. Therefore, it would be an advantage to provide a source of sclareol, which is less subjected to fluctuations in availability and quality. Chemical synthesis would seem to be an evident option for the preparation of sclareol. However, given its highly complex structure, an economic synthetic process for the preparation of sclareol is still difficult. A biochemical pathway leading to the synthesis of sclareol would therefore be of great interest.

The biosynthesis of terpenes in plants and other organisms has been extensively studied and is not further detailed in here, but reference is made to Dewick, *Nat. Prod. Rep.*, 2002, 19, 181-222, which reviews the state of the art of terpene biosynthetic pathways.

Several diterpene synthases have already been identified. In particular, U.S. Pat. No. 7,238,514 discloses a number of diterpene synthases, the nucleic acids encoding them, as well as unicellular organisms transformed to express each of these synthases together with a GGPP synthase, thus producing diterpenes in vivo. Nevertheless, no method for the biosynthetic production of sclareol using a polypeptide having a sclareol synthase activity as provided herein is specifically disclosed in that patent. The amino acid and nucleotide sequences disclosed in it are very different from the sequences of the present invention. Among the diterpene synthases described in that document, the closest to the polypeptides of the present invention are a *Cucumis sativus* mRNA for an ent-kaurene synthase designated by SEQ ID NO:389 in U.S. Pat. No. 7,238,514 and a *Cucurbita maxima* mRNA for an ent-kaurene synthase B designated by SEQ ID NO:395 in U.S. Pat. No. 7,238,514 and by the accession number AAB39482.1. These polypeptides and the one of the invention only share 32% identity. Moreover, there is no suggestion in this prior art document that the described diterpene synthases are useful for the production of sclareol.

Terpene synthases having a certain percentage of sequence identity with the sequences of the present invention have also been found in the sequences databases. Nevertheless, the percentage of identity between the known diterpene synthases and the polypeptides of the invention is very low. The closest synthases to the ones of the invention are a teipenoid cyclase of undefined function (Accession number NCBI AAS98912) having 36% identity with the polypeptide of the invention, an ent-kaurene synthase of *Cucumis sativus* (accession number BAB19275) having 32% identity with the polypeptide of the invention, an ent-cassadiene synthase from *Oryza sativa* (accession number ABH10734 and published in Xu, Wilderman, Morrone, Xu, Roy, Margis-Pinheiro, Upadhyaya, Coates and Peters, Functional characterization of the rice kaurene synthase-like gene family, Phytochemistry, 68(3), 2007, 312-326) having 32% identity with the polypeptide of the invention and an ent-kaurene synthase from *Oryza sativa* (accession number AAQ72559 and published in Margis-Pinheiro, Zhou, Zhu, Dennis and Upadhyaya, Isolation and characterization of a DS-tagged rice (*Oryza sativa* L.) GA-responsive dwarf mutant defective in an early step of the gibberellins biosynthesis pathway, Plant Cell Rep., 23(12), 2005, 819-833) having 32% identity with the polypeptide of the invention. The potential ability of any of these sequences to catalyze the production of sclareol is never mentioned in the prior art.

In addition to the difference between the sequences themselves, it also has to be pointed out that the structure and the properties of ent-kaurene and ent-cassadiene are very different from those of sclareol. In particular, ent-kaurene is a tricyclic diterpene which does not contain any alcohol functional groups, unlike sclareol, which is a bicyclic diol. Moreover, ent-kaurene, which is a precursor of a plant hormone regulating growth, is of no use in the field of perfumery and flavoring, whereas sclareol is of high interest in these technical fields, as explained above.

One document of the prior art relates specifically to a sclareol synthase (Banthorpe, Brown and Morris, Partial purification of farnesyl pyrophosphate: Drimenol cyclase and geranylgeranyl pyrophosphate: Sclareol cyclase, using cell culture as a source of material, Phytochemistry 31, 1992, 3391-3395). In this reference, a partially purified protein from *Nicotiana glutinosa* is identified as a sclareol synthase, but no indication is given regarding the amino acid sequence of that protein, the nucleotide sequence of the nucleic acid encoding it or the use of that protein in a method for the biosynthesis of sclareol in vitro or in vivo.

Despite extensive studies of terpene cyclization, the isolation and characterization of the enzymes is still difficult, particularly in plants, due to their low abundance, their often transient expression patterns, and the complexity of purifying them from the mixtures of resins and phenolic compounds in tissues where they are expressed.

It is an objective of the present invention to provide methods for making sclareol in an economic way, as indicated above. Accordingly, the present invention has the objective to produce diterpenes while having little waste, a more energy and resource efficient process and while reducing dependency on fossil fuels. It is a further objective to provide enzymes capable of sythesizing sclareol, which is useful as perfumery and/or aroma ingredients.

| Abbreviations Used | |
|---|---|
| bp | base pair |
| kb | kilo base |
| BSA | bovine serum albumine |
| DNA | deoxyribonucleic acid |
| cDNA | complementary DNA |
| dT | deoxy thymine |
| dNTP | deoxy nucleotide triphosphate |
| DTT | dithiothreitol |
| GC | gaseous chromatograph |
| GGPP | Geranylgeranyl pyrophosphate |
| IPTG | isopropyl-D-thiogalacto-pyranoside |
| LB | lysogeny broth |
| LPP | labdenediol diphosphate |
| MOPSO | 3-(N-morpholino)-2-hydroxypropanesulfonic acid |
| MS | mass spectrometer |
| ORF | open reading frame |
| PCR | polymerase chain reaction |
| RMCE | recombinase-mediated cassette exchange |
| RT-PCR | reverse transcription - polymerase chain reaction |
| 3'-/5'-RACE | 3' and 5' rapid amplification of cDNA ends |
| RNA | ribonucleic acid |
| mRNA | messenger ribonucleic acid |
| nt | nucleotide |
| RNase | ribonuclease |
| RuBisCO | ribulose-1,5-bisphosphate carboxylase |
| SDS-PAGE | SDS-polyacrylamid gel electrophoresis |
| SsLPPs | *Salvia sclarea* labdenediol diphosphate synthase |
| UTR | Untranslated Region |

DESCRIPTION OF THE INVENTION

The present invention provides a method to biosynthetically produce sclareol in an economic, reliable and reproducible way.

One object of the present invention is therefore a method for producing sclareol comprising
a) contacting labdenediol diphosphate (LPP) with at least one polypeptide having a sclareol synthase activity and comprising an amino acid sequence at least 50% identical to SEQ ID NO:1; and
b) optionally, isolating the sclareol produced in step a).

The method can be carried out in vitro as well as in vivo, as will be explained in details further on.

Sclareol and LPP are defined by the way of their formulae as represented in FIG. 1.

As a "sclareol synthase" or as a "polypeptide having a sclareol synthase activity", we mean here a polypeptide capable of catalyzing the synthesis of sclareol starting from (LPP). The ability of a polypeptide to catalyze the synthesis of sclareol can be confirmed by performing the enzyme assay as detailed in the Examples.

According to the present invention, polypeptides are also meant to include truncated polypeptides provided that they keep their sclareol synthase activity as defined above and that they share at least the defined percentage of identity with the corresponding fragment of SEQ ID NO:1.

According to a preferred embodiment, the method for producing sclareol comprises contacting LPP with a polypeptide having a sclareol synthase activity and comprising an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, said polypeptide comprises the amino acid sequence SEQ ID NO:1. In an even more preferred embodiment, said polypeptide consists of SEQ ID NO:1.

According to a preferred embodiment, the sclareol synthase is a truncated polypeptide comprising an amino acid sequence at least 50% identical to SEQ ID NO:102. Preferably the polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:96. According to another preferred embodiment, the polypeptide comprises the amino acid sequence SEQ ID NO:96. According to a more preferred embodiment, the polypeptide consists of SEQ ID NO:96.

The percentage of identity between two peptidic or nucleotidic sequences is a function of the number of amino acids or nucleic acids residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for purposes of determining the percentage of amino acid or nucleic acid sequence identity can be achieved in various ways using computer programs and for instance publicly available computer programs available on the world wide web. Preferably, the BLAST program (Tatiana et al, FEMS Microbiol Lett., 1999, 174:247-250, 1999) set to the default parameters, available online from the National Center for Biotechnology Information (NCBI), can be used to obtain an optimal alignment of peptidic or nucleotidic sequences and to calculate the percentage of sequence identity.

The polypeptide to be contacted with LPP in vitro can be obtained by extraction from any organism expressing it, using standard protein or enzyme extraction technologies. If the host organism is a unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptides, either in an isolated form or together with other proteins, for example in a crude protein extract obtained from cultured cells or microorganisms, may then be suspended in a buffer solution at optimal pH. If adequate, salts, DTT, BSA and other kinds of enzymatic co-factors, may be added in order to optimize enzyme activity. Appropriate conditions are described in more details in the Examples further on.

LPP may then be added to the suspension or solution, which is then incubated at optimal temperature, for example between 15 and 40° C., preferably between 25 and 35° C., more preferably at 30° C. After incubation, the sclareol produced may be isolated from the incubated solution by standard isolation procedures, such as solvent extraction and distillation, optionally after removal of polypeptides from the solution.

LPP can be obtained by contacting GGPP with an isolated LPP synthase. Examples 1 to 3 below show a method to isolate a LPP synthase encoding cDNA from *Salvia sclarea*, a method for the heterologous expression of said cDNA in *E. coli*, a method for the purification of the LPP synthase so produced and a method for the in vitro production of LPP using the isolated LPP synthase.

According to another preferred embodiment, the method for producing sclareol is carried out in vivo. In this case, step a) of the above-described method comprises cultivating a non-human organism or cell capable of producing LPP and transformed to express a polypeptide having a sclareol synthase activity and comprising an amino acid sequence at least 70% identical to SEQ ID NO:1 under conditions conducive to the production of sclareol.

According to a more preferred embodiment, the method further comprises, prior to step a), transforming a non human organism or cell capable of producing LPP with at least one nucleic acid encoding a polypeptide having a sclareol synthase activity and comprising an amino acid sequence at least 70% identical to SEQ ID NO:1, so that said organism expresses said polypeptide.

According to a preferred embodiment, the nucleic acid used to transform the host organism or cell comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2 or the complement thereof. According to another preferred embodiment, the nucleic acid comprises the nucleotide sequence SEQ ID NO:2 or the complement thereof. According to a more preferred embodiment, the nucleic acid consists of SEQ ID NO:2 or the complement thereof.

According to a further preferred embodiment, the nucleic acid used to transform the host organism or cell is a truncated nucleic acid comprising a nucleotide sequence at least 50%, preferably at least 55%, preferably at least 60%, preferably at least 70%, preferably at least 75%, preferably at least 80%, preferably at least 85%, preferably at least 90%, more preferably at least 95% and even more preferably at least 98% identical to SEQ ID NO:93 or the complement thereof. According to another preferred embodiment, the nucleic acid comprises the nucleotide sequence SEQ ID NO:93 or the complement thereof. According to a more preferred embodiment, the nucleic acid consists of SEQ ID NO:93 or the complement thereof.

These embodiments of the invention are particularly advantageous since it is possible to early out the method in vivo without previously isolating the polypeptide. The reaction occurs directly within the organism or cell transformed to express said polypeptide.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human organism or cell will be described later on in the part of the specification that is dedicated to such transformed non-human organisms or cells as specific objects of the present invention and in the Examples.

A particular organism or cell is meant to be "capable of producing LPP" when it produces LPP naturally or when it does not produce LPP naturally but produces GGPP (or is so transformed) and is transformed to express a LPP synthase, either prior to the transformation with a nucleic acid encoding a sclareol synthase or together with said nucleic acid. Organisms or cells transformed to produce a higher amount of LPP than the naturally occurring organism or cell are also encompassed by the "organisms or cells capable of producing LPP". According to a preferred embodiment, the organism accumulates LPP naturally or is transformed to accumulate LPP.

Methods for transforming organisms so that they express a LPP synthase, can be any method known in the art to transform a host organism. Such methods are exposed in more details later on and a specific example of the expression of a LPP synthase in *E. coli* is given in Example 2. Methods for transforming an organism to produce GGPP are also known in the art. Such methods can for example be found in Huang, Roessner, Croteau and Scott, Engineering *Escherichia coli* for the synthesis of taxadiene, a key intermediate in the biosynthesis of taxol, Bioorg Med Chem., 9(9), 2001, 2237-2242.

To carry out the invention in vivo, the host organism or cell is cultivated under conditions conducive to the production of sclareol. Accordingly, if the host is a transgenic plant, optimal growth conditions are provided, such as optimal light, water and nutrient conditions, for example. If the host is a unicellular organism, conditions conducive to the production of sclareol may comprise addition of suitable cofactors to the culture medium of the host. In addition, a culture medium may be selected, so as to maximize sclareol synthesis. Optimal culture conditions are described in a more detailed manner in the following Examples.

Non-human organisms suitable to carry out the method of the invention in vivo may be any non-human multicellular or unicellular organisms. In a preferred embodiment, the non-human organism used to carry out the invention in vivo is a plant, a prokaryote or a fungus.

Any plant, prokaryote or fungus may be used to carry out the method of the invention in vivo. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human organism is a microorganism. According to an even more preferred embodiment said microorganism is a bacteria or a fungus, preferably said fungus is yeast. Most preferably, said bacteria is *E. coli* and said yeast is *Saccharomyces cerevisiae*.

Most of these organisms do not produce LPP naturally. To be suitable to carry out the method of the invention, these organisms have to be transformed to produce said precursor. They can be so transformed either before the modification with the nucleic acid encoding the polypeptide having a sclareol synthase activity or simultaneously, as explained above.

Isolated higher eukaryotic cells can also be used, instead of complete organisms, as hosts to carry out the method of the invention in vivo. Suitable eukaryotic cells may be any non-human cell, but are preferably plant cells.

According to another preferred embodiment, the polypeptide or the nucleic acid used in the method of any of the embodiments above is derived from *Salvia sclarea*.

An important tool to carry out the method of the invention is the polypeptide itself. A polypeptide having a sclareol synthase activity and comprising an amino acid sequence at least 50% identical to SEQ ID NO:1 is therefore another object of the present invention.

According to a preferred embodiment, the sclareol synthase comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to another preferred embodiment, the polypeptide comprises the amino acid sequence SEQ ID NO:1. According to a more preferred embodiment, the polypeptide consists of SEQ ID NO:1.

According to another preferred embodiment of the invention, the polypeptide is derived from *Salvia sclarea*.

As used herein, the terms "sclareol synthase" or "polypeptide having a sclareol synthase activity" refers to a genus of polypeptides or peptide fragments that encompasses the amino acid sequences identified herein, as well as truncated or variant polypeptides, provided that they keep their sclareol synthase activity as defined above and that they share at least the defined percentage of identity with the corresponding fragment of SEQ ID NO:1.

According to a preferred embodiment, the sclareol synthase comprises an amino acid sequence at least 50% identical to SEQ ID NO:96. Preferably the sclareol synthase comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:96. According to another preferred embodiment, the polypeptide comprises the amino acid sequence SEQ ID NO:96. According to a more preferred embodiment, the polypeptide consists of SEQ ID NO:96.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by mutation of a nucleic acid of the invention, as described thereafter, are also encompassed by the invention.

The nucleic acid encoding the polypeptide having a sclareol synthase activity, as defined above, is a necessary tool to modify non-human organisms or cells intended to be used when the method is carried out in vivo. A nucleic acid encoding a polypeptide as defined in any of the above embodiments is therefore another object of the invention.

According to a preferred embodiment, the nucleic acid comprises a nucleotide sequence at least 50% identical to SEQ ID NO:2 or the complement thereof. According to a more preferred embodiment, said nucleic acid comprises a nucleotide sequence at least 55%, preferably at least 60%, preferably at least 65%, preferably at least 70%, preferably at least 75%, preferably at least 80%, more preferably at least 85%, more preferably at least 90%, more preferably at least 95% and even more preferably at least 98% identical to SEQ ID NO:2 or the complement thereof. According to a more preferred embodiment, the nucleic acid comprises a nucleotide sequence identical to SEQ ID NO:2 or the complement thereof. According to an even more preferred embodiment, the nucleic acid consists of SEQ ID NO:2 or the complement thereof.

According to another preferred embodiment of the invention, the nucleic acid is derived from *Salvia sclarea*.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above. Particularly useful truncated nucleic acids are the nucleic acids at least 70% identical to SEQ ID NO:93 or the complement thereof.

The nucleic acids obtained by mutations of SEQ ID NO:2 or of the complement thereof are also encompassed by the invention, provided that they share at least the defined percentage of identity with the corresponding fragment of SEQ ID NO:2 and that they encode polypeptides having a sclareol synthase activity, as defined above. Mutations may be any kind of mutations of these nucleic acids, such as point mutations, deletion mutations, insertion mutations and/or frame shift mutations. Variant nucleic acids may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

According to a further preferred embodiment, the nucleic acid is a truncated nucleic acid comprising a nucleotide sequence at least 50%, preferably at least 55%, preferably at least 60%, preferably at least 70%, preferably at least 75%, preferably at least 80%, preferably at least 85%, preferably at least 90%, more preferably at least 95% and even more preferably at least 98% identical to SEQ ID NO:93 or the complement thereof. According to another preferred embodiment, the nucleic acid comprises the nucleotide sequence SEQ ID NO:93 or the complement thereof According to a more preferred embodiment, the nucleic acid consists of SEQ ID NO:93 or the complement thereof.

Generally speaking, the nucleic acid of the invention can be isolated using a massively parallel sequencing approach, which is extensively developed in Examples 5 and 6. The first step of this method is the global sequencing of the cDNA library. The cDNA library is first fragmented by nebulization. The fragments are then amplified by PCR and the sequencing reaction is carried out. Short sequences of 35 bases named "reads" are obtained. "Reads" are reassembled in contiguous sequences ("contigs") using a software with defined minimum length of overlap and percentage of homology settings. "Reads" and "contigs" are then searched for sequence identity with known enzymes of the same type. On the basis of these homologies, "reads" and "contigs" are selected and used to synthesize primers in order to carry out the PCR amplification of the full length sclareol synthase.

Another important tool for transforming host organisms or cells suitable to carry out the method of the invention in vivo is an expression vector comprising at least one nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vectors include the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides having a sclareol synthase activity, as disclosed further below.

Recombinant non-human organisms and cells transformed to harbor at least one nucleic acid of the invention, so that it heterologously expresses or over-expresses at least one polypeptide of the invention are also very useful tools to carry out the method of the invention. Such non-human organisms and cells are therefore another object of the present invention.

Non-human organisms of the invention may be any non-human multicellular or unicellular organisms. In a preferred embodiment, the non-human organism of the invention is a plant, a prokaryote or a fungus. Said organism may be any plant, prokaryote or fungus. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human organism is a microorganism. According to an even more preferred embodiment said microorganism is a bacteria or yeast and most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells or fungal cells.

The term "transformed" refers to the fact that the host was subjected to genetic engineering to comprise one, two or more copies of any of the nucleic acids of the invention. Preferably the term "transformed" relates to hosts heterologously expressing the polypeptides of the invention, as well as over-expressing them. Accordingly, in an embodiment, the present invention provides a transformed organism, in which the polypeptide of the invention is expressed in higher quantity than in the same organism not so transformed.

There are several methods known in the art for the creation of transgenic host organisms or cells such as plants, fungi, prokaryotes, or cell cultures of higher eukaryotic organisms. Appropriate cloning and expression vectors for use with bacterial, fungal, yeast, plant and mammalian cellular hosts are described, for example, in Pouwels et al., Cloning Vectors: A Laboratory Manual, 1985, Elsevier, N.Y. and Sambrook et al., Molecular Cloning: A Laboratory Manual, $2^{nd}$ edition, 1989, Cold Spring Harbor Laboratory Press. Cloning and expression vectors for higher plants and/or plant cells in particular are available to the skilled person. See for example Schardl et al. Gene 61: 1-11, 1987.

Methods for transforming host organisms or cells to harbor transgenic nucleic acids, such as those of the present invention, are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardement, microinjection of plant cells, and transformation using viruses.

In one embodiment, transformed DNA is integrated into a chromosome of a non-human host organism and/or cell such that a stable recombinant systems results. Any chromosomal integration method known in the art may be used in the practice of the invention, including but not limited to, recombinase-mediated cassette exchange (RMCE), viral site-specific chromosomal insertion, adenovirus, and pronuclear injection.

In order to carry out the method for producing sclareol in vitro, as exposed herein above, it is very advantageous to provide a method of making at least one polypeptide having a sclareol synthase activity. Therefore, the invention provides a method for producing at least one polypeptide having a sclareol synthase activity comprising
a) culturing a non-human organism or cell transformed with the expression vector of the invention, so that it harbors a nucleic acid according to the invention and expresses or over-expresses a polypeptide encoded by said nucleic acid and having a sclareol synthase activity;
b) isolating the polypeptide having a sclareol synthase activity from the non-human organism or cell cultured in step a).

According to a preferred embodiment, said method further comprises, prior to step a), transforming a non-human host organism or cell with at least one expression vector of the invention, so that it harbors at least one nucleic acid according to the invention and expresses or over-expresses at least one polypeptide encoded by said nucleic acid.

Transforming and culturing of the non-human organism or cell can be carried out as described above for the method of producing sclareol in vivo. Step b) may be performed using any technique well known in the art to isolate a particular polypeptide from an organism or cell.

A "polypeptide variant" as referred to herein means a polypeptide having a sclareol synthase activity and being substantially homologous to a native polypeptide, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physicochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, Biochemistry, Addison-Wesley Pub. Co., (1983). The effects of such substitutions can be calculated using substitution score matrices such a PAM-120, PAM-200, and PAM-250 as discussed in Altschul, (J. Mol. Biol. 219:555-65, 1991). Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the polypeptides of the invention may be used to attain desired enhanced or reduced enzymatic activity, modified regiochemistry or stereochemistry, or altered substrate utilization or product distribution. Furthermore, variants may be prepared to have at least one modified property, for example an increased affinity for the substrate, an improved specificity for the production of one or more desired compounds, a different product distribution, a different enzymatic activity, an increase of the velocity of the enzyme reaction, a higher activity or stability in a specific environment (pH, temperature, solvent, etc), or an improved expression level in a desired expression system. A variant or site directed mutant may be made by any method known in the art. As stated above, the invention provides recombinant and non-recombinant, isolated and purified polypeptides, such as from *Salvia sclarea*. Variants and derivatives of native polypeptides can be obtained by isolating naturally-occurring variants, or the nucleotide sequence of variants, of other or same plant lines or species, or by artificially programming mutations of nucleotide sequences coding for native sclareol synthases. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides.

Therefore, in an embodiment, the present invention provides a method for preparing a variant polypeptide having a sclareol synthase activity and comprising the steps of:
(a) selecting a nucleic acid according to any of the embodiments exposed above;
(b) modifying the selected nucleic acid to obtain at least one mutant nucleic acid;
(c) transforming host cells or unicellular organisms with the mutant nucleic acid sequence to express a polypeptide encoded by the mutant nucleic acid sequence;
(d) screening the polypeptide for at least one modified property; and,
(e) optionally, if the polypeptide has no desired variant sclareol synthase activity, repeat the process steps (a) to (d) until a polypeptide with a desired variant sclareol synthase activity is obtained;
(f) optionally, if a polypeptide having a desired variant sclareol synthase activity was identified in step d), isolating the corresponding mutant nucleic acid obtained in step (c).

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. Proc Natl Acad Sci USA., 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, SEQ ID NO:2 or 93 may be recombined with any other diterpene synthase encoding nucleic acids, for example isolated from an organism other than Salvia sclarea. Thus, mutant nucleic acids may be obtained and separated, which may be used for transforming a host cells according to standard procedures, for example such as disclosed in the present Examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present Examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

In an embodiment, the present invention provides a method for preparing a nucleic acid encoding a variant polypeptide having a sclareol synthase activity, the method comprising the steps (a)-(e) disclosed above and further comprising the step of:

All the publications mentioned in this application are incorporated by reference to disclose and describe the methods and/or materials in connection with which the publications are cited.

DESCRIPTION OF THE DRAWINGS

FIGS. 3A-3B: Alignment of amino acid sequences from the class I diterpene synthase-like fragments Contig-250 (SEQ ID NO:44), Contig-231 (SEQ ID NO:45), Contig-147 (SEQ ID NO:46), Contig-33 (SEQ ID NO:47), Contig-1610-fox2 (SEQ ID NO:104), and Contig-224 (SEQ ID NO:48), with the sequence of the stemodene synthase from Oriza sativa (SEQ ID NO:99, Access. No. AAZ76733).

Figure 4A:
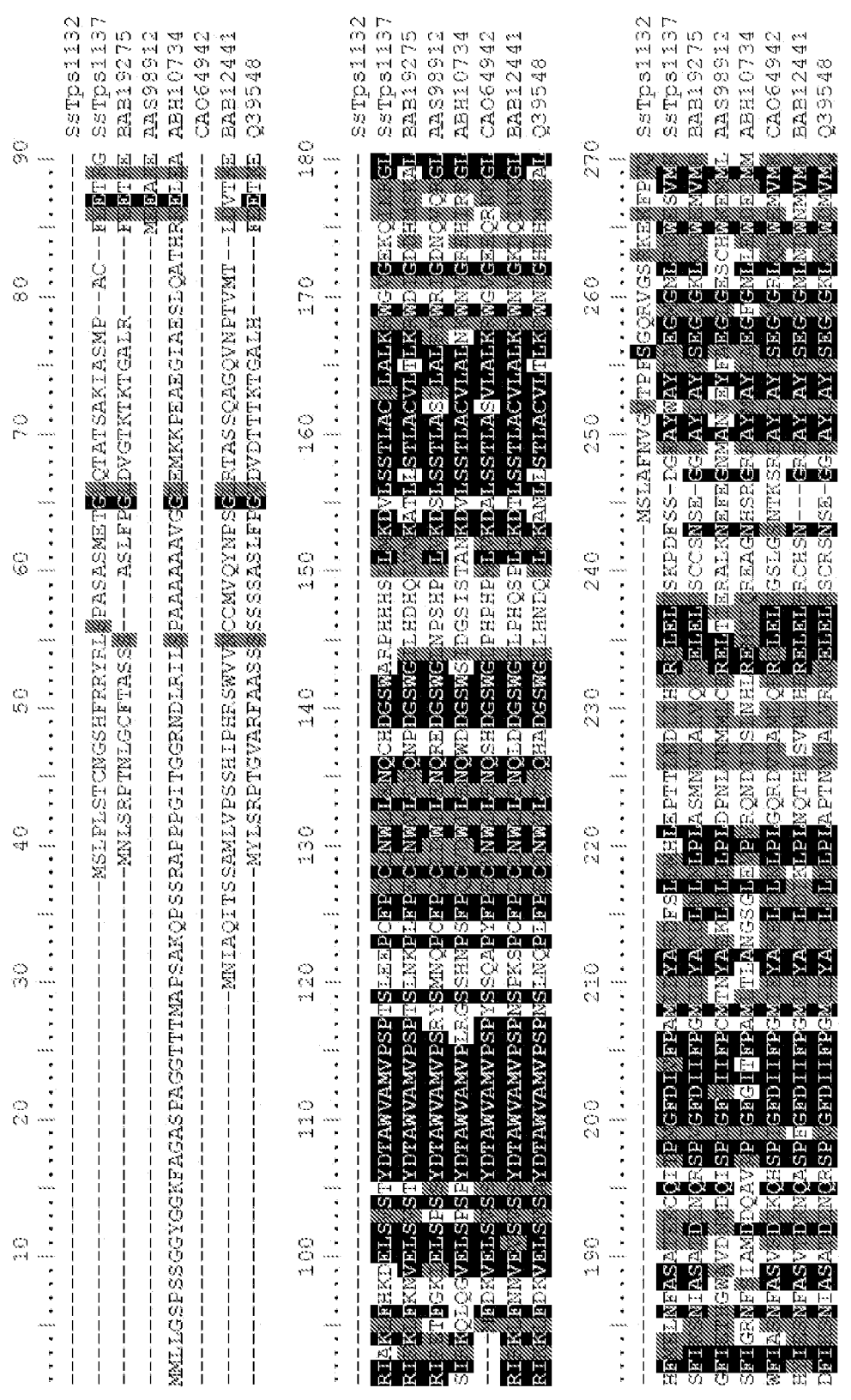
Figure 4C:
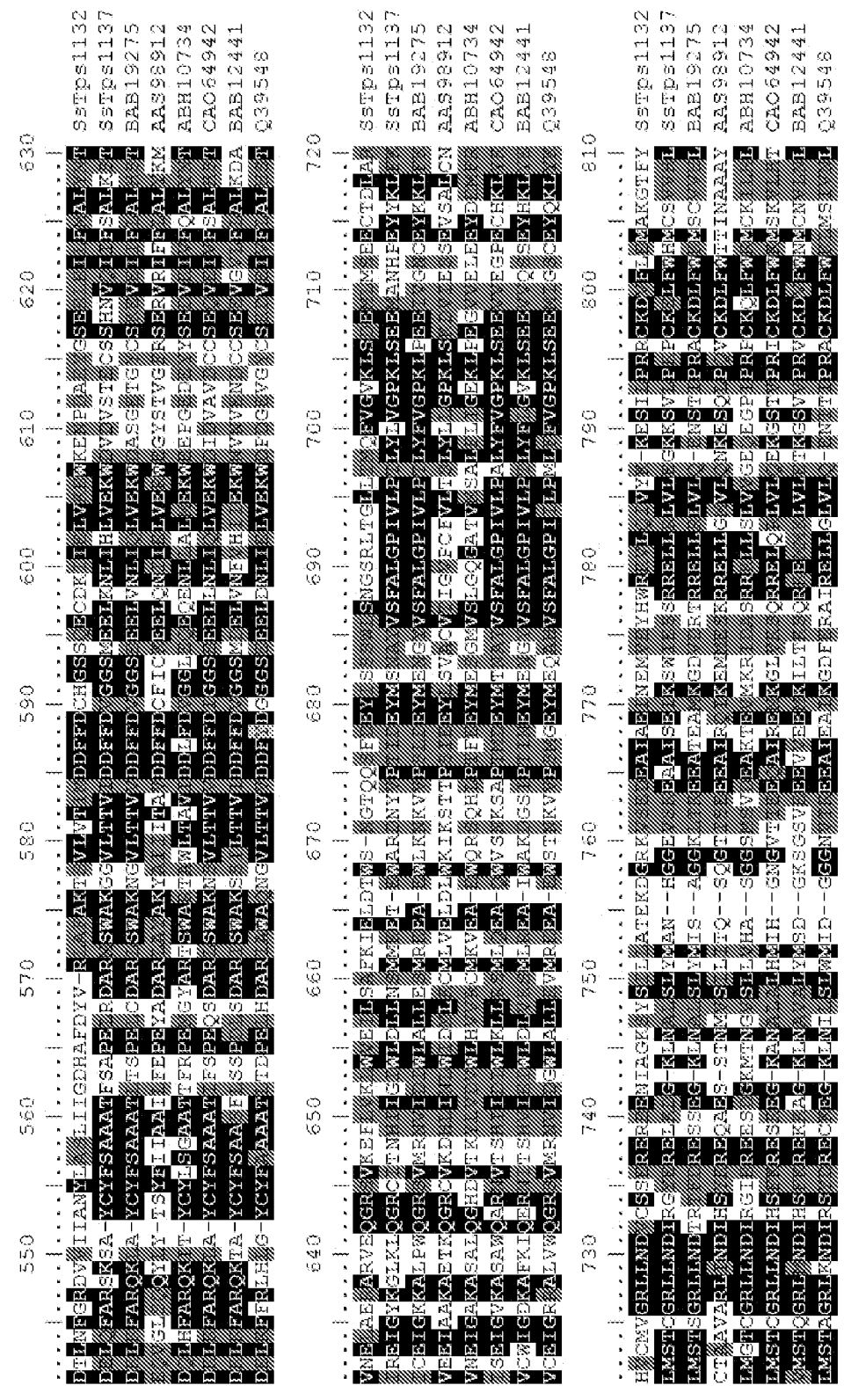
Figure 4D:
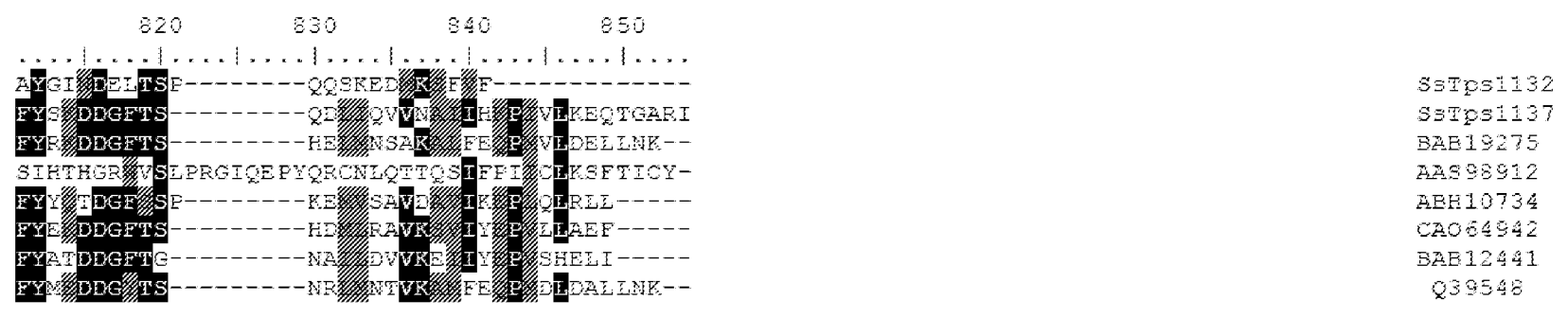

FIGS. 4A-4D: Alignment of the amino acid sequence deduced from SsTps1132 (SEQ ID NO:1) and SsTps1137 (SEQ ID NO:86) with diterpene synthases amino acid sequences BAB19275 (SEQ ID NO:106), AAS98912 (SEQ ID NO:107), ABH10734 (SEQ ID NO:108), CAO64942 (SEQ ID NO:109), BAB12441 (SEQ ID NO:110), and Q39548 (SEQ ID NO:111) selected from the database.

SPECIFIC EMBODIMENTS OF THE INVENTION OR EXAMPLES

Figure 1:
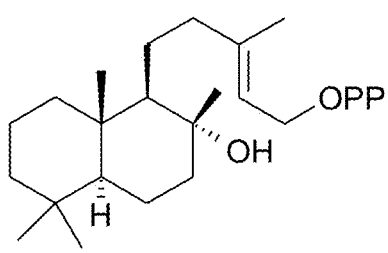
FIG. 1: Structures of the diverse compounds cited in the description.
Figure 1:
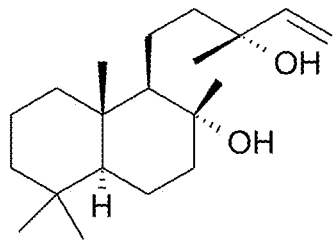
Figure 1:
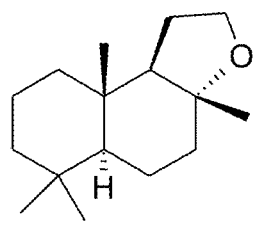
Figure 1:
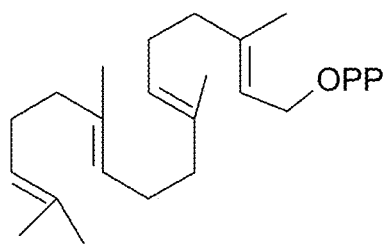
Figure 1:
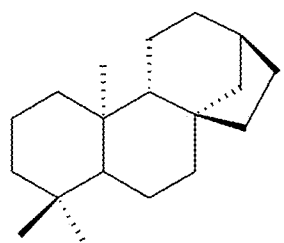
Figure 1:
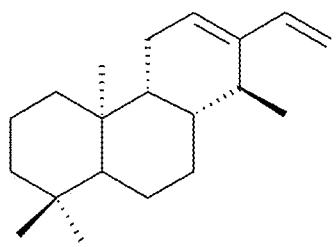
Figure 2:
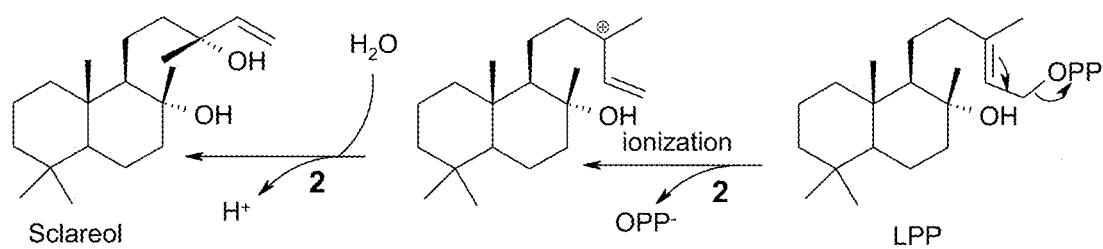
FIG. 2: Putative biosynthesis of sclareol from LPP, which is catalyzed by the SsTps1132 (SEQ ID NO:1).

The invention will now be described in further detail by way of the following Examples.

Example 1

Isolation of LPP Synthase Encoding cDNAs from Salvia clarea by a PCR Approach.

A. Plant Material and RNA Extraction.

Salvia sclarea developing flower buds (1.5 to 2 cm length, 1-2 days old) were collected in fields of Bassins (Switzerland) and directly frozen in liquid nitrogen.

Total RNA was extracted using the Concert™ Plant RNA Reagent from Invitrogen (Carlsbad, Calif.) and the mRNA was purified by oligodT-cellulose affinity chromatography using the FastTrack® 2.0 mRNA isolation Kit (Invitrogen, Carlsbad, Calif.) according to the manufacturer's instructions. A cDNA library was constructed using the Marathon™ cDNA Amplification Kit (Clontech, Mountain View, Calif.).

B. Polymerase Chain Reactions for Amplification of Diterpene Synthases cDNAs

PCR were performed using the forward primer DT3F (5'-GAYRTNGAYGAYACNGCNATGG-3' (SEQ ID NO:3)) and the reverse primer DT4R (5'-GTYTTNCCNAKC-CANACRTCRYYT-3' (SEQ ID NO:4)). The PCR mixture contained 0.4 µM of each primer, 300 µM each dNTPs, 5 µL of 10× HotStartTaq® DNA polymerase buffer (Qiagen), 2 µL of 100 fold diluted cDNA, 0.5 µL of HotStartTaq® DNA polymerase in a final volume of 50 µL. The cycling conditions were: 35 cycles of 45 sec at 94° C., 45 sec at 50° C. and 2 min at 72° C.; and 10 min at 72° C. The sizes of the PCR products were evaluated on a 1% agarose gel. The bands corresponding to the expected size were excised from the gel, purified using the QIAquick® Gel Extraction Kit (Qiagen) and cloned in the pCR®2.1-TOPO vector using the TOPO TA cloning Kit (Invitrogen, Carlsbad, Calif.). Inserted cDNAs fragments were then subject to DNA sequencing and the sequence was compared against the GenBank non-redundant protein database (NCBI) using the BLASTX algorithm (Altschul et al, J. Mol. Biol. 215, 403-410, 1990). A 354 bp sequence named FN23 (SEQ ID NO:5) was obtained. This DNA fragment possessed the expected size and showed sequence homology to diterpene synthases.

C. Full Length cDNA Isolation by Rapid Amplification of cDNA Ends (RACE).

Oligonucleotides specific for the FN23 sequence (SEQ ID NO:5) were designed: FN23-F1 (3'-GCACGGATAC-GACGTCGATCCAAATGTAC-5' (SEQ ID NO:6)), FN23-F2 (3'-GGGCTGCTCAACTAAGATTTCCAGGAG-5' (SEQ ID NO:7)) and FN23-F3 (5'-GGGTGATATCCGAC-CACTTATTTGATGAG-5' (SEQ ID NO:8)). These primers were used in RT-PCR in combination with oligodT primers extended with an adaptor sequence (5'-AATTCGGTAC-CCGGGATCC(T)$_{17}$-3') (SEQ ID NO:9). The composition of the RT-PCR reaction mixture was the following: 10 µl 5× Qiagen OneStep RT-PCR buffer, 400 µM each dNTP, 400 nM each primer, 2 µl Qiagen OneStep RT-PCR Enzyme Mix, 1 µl RNasin® Ribonuclease Inhibitor (Promega Co., Madisson, Wis.) and 1250 ng total RNA in a final volume of 50 ml. The thermal cycler conditions were: 30 min at 50° C. (reverse transcription); 15 min at 95° C. (DNA polymerase activation); 35 cycles of 45 sec at 94° C., 45 sec at 50° C. and 90 sec at 72° C.; and 10 min at 72° C. A second round of PCR was performed using the RT-PCR products as template with the adapterP primer (5'-AATTCGGTACCCGGGATCC-3' (SEQ ID NO:10)) in combination with the same or nested FN23-specific primers. This PCR approach provided a 1271 bp cDNA fragment (FN30 (SEQ ID NO:11)) having a 192 bp perfect overlap with the FN23 fragment (SEQ ID NO:5) and containing the 3'end including the stop codon and the 3' non-coding sequence of the corresponding cDNA.

For amplification of the 5' end of the cDNA, anti-sense oligonucleotides specific for FN23 were designed: FN23-R1 (5'-CATGGCATCTTCAACCCCAGCTTTATCTCATC-3' (SEQ ID NO:12)), FN23-R2 (5'-GTGGTCGGATATCAC-CCATCTTTCTTGAAGTCG-3' (SEQ ID NO:13)), FN23-R3 (5'-CATTGGAGATGCAGACTCGACCGATTGACC-3' (SEQ ID NO:14)). These primers were used for 5'RACE using the S. sclarea cDNA library following the Marathon™ cDNA Amplification Kit protocol (Clontech, Mountain View, Calif.). The thermal Cycling conditions were as follows: 1 min at 94° C., 5 cycles of 30 sec at 94° C. and 4 min at 72° C., 5 cycles of 30 sec at 94° C. and 4 min at 70° C., 20 cycles of 30 sec at 94° C. and 4 min at 68° C. This 5'RACE provided a 1449 bp cDNA fragment (FN40 (SEQ ID NO:15)) having a 227 bp perfect overlap with FN23 (SEQ ID NO:5). Comparison with known diterpene synthases sequences revealed that the FN40 fragment (SEQ ID NO:15) contained the translation initiation codon and a 87 bp non-coding region. The assembling of the three cDNA fragments (FN23, FN30 and FN40 (SEQ ID NO:5, 11 and 15) provided a full length cDNA sequence (SaTps1) of 2655 bp (SEQ ID NO:16) with an open reading frame of 2355 bp coding for a 785 residues protein (SEQ ID NO:17).

Example 2

Heterologous Expression of the S. sclarea LPP Synthase in E. coli.

The pETDuet-1 (Novagen, Madison, Wis.), designed for expression under the control of a T7 promoter, was used for expression in E. coli cells. To construct the expression plasmid, the open reading frame of SaTps1 (SEQ ID NO:16) was amplified by PCR from the cDNA library with the forward and reverse primers SaTps-Nde (3'-TACTGACATATGACT-TCTGTAAATTTGAGCAGAGCACC-5' (SEQ ID NO:18)) and SaTps-Kpn (3'-TTGGTACCTCATACAACCGGTC-GAAAGAGTACTTTG-5' (SEQ ID NO:19)) designed to introduce an NdeI site immediately before the start codon and a KpnI site after the stop codon. Since the open reading frame contains an NdeI site at position of 1614 of the open reading frame, this amplification was performed in two steps by overlap extension PCR (Horton et al, Gene 77, 61-68, 1989), using the primers SaTps-Nde (SEQ ID NO:18) and SaTps-Kpn (SEQ ID NO:19) in combination with the primers Satps-mut1f (5'-GTTGGAGTGGATCCACATGCAGGAATGG-TAC-3' (SEQ ID NO:20)) and Satps-mut1r (3'-GTACCAT-TCCTGCATCTGGATCCACTCCAAC-5' (SEQ ID NO:21)), designed to remove the NdeI site without altering the amino acid sequence. The resulting cDNA were first ligated in the PCR2.1-Topo plasmid using the TOPO TA Cloning Kit (Invitrogen, Carlsbad, Calif.) and the sequences of the inserts were verified prior to sub-cloning as NdeI-KpnI fragment into the pETDuet-1 vector.

Analysis of the sequence of several clones obtained by amplification from the cDNA library with the SaTps1 specific primers showed some variability in several positions of the cDNA sequence. Seven positions were identified, in which two different amino acids can be found. One position was found were insertion of a serine residue occurred in some of the clones. These positions are listed in the table below.

| Positions (relative to the amino acid sequence) | Amino acid |
| --- | --- |
| 34 | Ile or Thr |
| 40 | Phe or Leu |
| 174 | Gln or His |
| 222 | Gly or Asp |
| 538 | Gln or His |
| 560 | Arg or Leu |
| 596 | Asn or Lys |
| 612 | Insertion of a Ser |

These variations seemed to occur in a random manner in eleven different clones sequenced, suggesting that at least two very closely related isoforms of a diterpene synthase are present in the S. sclarea genome and that the PCR amplification approach leaded to shuffling of the sequences. Two clones, SsLPPs3 (SEQ ID NO:22) and SsLPPs9 (SEQ ID NO:23) representative of the sequences variability, were selected for the heterologous expression and enzyme characterization experiments.

The plasmids pETDuet-SsLPPs3 and pETDuet-SsLPPs9 were transferred into B121(DE3) E. Coli cells (Novagen, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g), and the supernatants containing the soluble proteins were used for further experiments.

The crude protein extracts from pETDuet-SsLPPs3 and pETDuet-SsLPPs9 transformed cells were analyzed by SDS-PAGE and compared to protein extracts obtained from cells transformed with the empty pETDuet plasmid. The recombinant SsLPPs3 and SsLPPs9 proteins (SEQ ID NO:24 and 25) were clearly detected and the apparent molecular weight estimated at 90 KDa, a value in concordance with the calculated molecular weight of 83 KDa.

Example 3

Purification of the LPP Synthase from *Salvia sclarea* and Enzymatic Activities

The PCR2.1-Topo plasmids containing the SsLPPs3 and SsLPPs9 cDNA (SEQ ID NO:22 and 23) (Example 2) were digested with NdeI and SacI and the inserts were ligated into the pET28a(+) plasmid (Novagen). The resulting expression plasmids (pET28-SsLPPs3 and pET28-SsLPPs9) contain the cDNAs with a 5'-end modification designed to express the proteins with an N-terminal hexa-histidine tag (His-tag). Purification was performed under native conditions using the ProBond™ Purification System (Invitrogen) following the manufacturer protocol excepted that, for the elution, imidazole was replaced by L-histidine to minimize inhibition of the enzyme. Using this approach, the SsLPPs3 and SsLPPs9 "His-tag" recombinant enzymes (SEQ ID NO:97 and 98) could be purified to apparent homogeneity.

The affinity purified enzymes were incubated 12 hours at 30° C. with 200 µM GGPP and 1 mM DTT in MOPSO pH 7, 10% glycerol, 1 mM DTT. No diterpene product was observed by extracting the incubation medium with pentane and analysis of the extract by GC or GC-MS. Treatment of the same extract by alkaline phosphatase (Sigma, 6 units/ml), followed by extraction with pentane and GC analysis, showed the formation of labdenediol and demonstrated the enzymatic formation of labdenediol-diphosphate (LPP) as unique product from GGPP by the recombinant diterpene synthase.

The GC analysis was performed on an Agilent 6890 Series GC system equipped with a flame ionization detector using a 0.25 mm inner diameter by 30 m SPB-1 capillary column (Supelco, Bellefonte, Pa.). The carrier gas was He at a constant flow of 1.5 mL/min. The initial oven temperature was 100° C. (1 min hold) followed by a gradient of 10° C./min to 300° C. The GC-MS analysis was performed in the same conditions and the spectra were recorded on an Agilent 5975 mass detector.

Example 4

PCR Approach for the Homology Cloning of Class I Diterpene Synthases (Sclareol Synthase) from *S. sclarea*.

The cloning and characterization of SsLPPs3 (SEQ ID NO:24) and SsLPPs9 (SEQ ID NO:25), in Examples 1 to 3, suggest that the biosynthesis of sclareol in *S. sclarea* involves two proteins, the SsLPPs and a class I diterpene synthase, the sclareol synthase, catalyzing the conversion of LPP to sclareol.

A PCR approach was used in a first attempt for the isolation of class I diterpene synthases cDNA sequences. Oligonucleotides were designed based on conserved sequences in plant diterpene synthases and especially in diterpene synthases catalyzing the cyclization of $C_{20}$-diphosphate esters via an ionization mechanism. The sequences with accession numbers BAB19275, AAB39482, AAD30231, AAD34295, CAE05201, BAB12441, AAT49066, CAE05199, AAU05906, BAD17672, AAQ72565, AAL09965, AAK83563, AAS47691, AAS47690 and AAR13860, were selected from the National Center for Biotechnology Information online public sequence databases. All these protein sequences correspond to class I diterpene synthases and contain the DDxxD motif (wherein x represents any amino acid) characteristic of ionization-dependent cyclization mechanism in terpene synthases. From the alignment of these sequences, two conserved motifs were first selected in the N-terminal region and used for the design of sense oligonucleotides: YDT(A/S)WVA and (D/N)GSWG. In the amino acid sequence of the SsLPPs (SEQ ID NO:24 and 25, Examples 1 to 3) these two motifs were also conserved, though with some differences for the first motif (YDTAVIA). Thus the sequence of SsLPPs was also taken into account for the design of the sense oligonucleotides. From the first motif, three oligonucleotides were design to cover all the sequences variations: DiTpsTB_F1, 5'-TATGATACNGCNGT-NATDGC-3' (SEQ ID NO:26); DiTpsTB_F2, 5'-TATGA-CACGGCAGTGATCGC-3' (SEQ ID NO:27); DiTpsTB_F3, 3'-TATGACACGGCAKKGRTNGC-5' (SEQ ID NO:28). From the second motif, two oligonucleotides were designed: DiTpsTB_F4, 5'-CAACTGGCTGATGGNTCNTGGGG-3' (SEQ ID NO:29); DiTpsTB_F5, 5'-CAACTGGCTGATG-GCTCATGGGG-3' (SEQ ID NO:30). The DDxxD motif, located in the C-terminal region of the proteins and involved in the binding of the diphosphate moiety in the active site, was used to design two anti-sense oligonucleotides: DiTpsTB_R1, 5'-GATCCTCCAACRTCRWARARRTCRTC-3' (SEQ ID NO:31), DiTpsTB_R2, 5'-GATCCTCCACGTCG-WAGAAGTCGTC-3' (SEQ ID NO:32).

These primers were used for PCR amplification from a *Salvia sclarea* cDNA library (prepared as described in Example 1). The PCRs were performed using the Advantage® 2 Polymerase Mix (Clontech). Each PCR mixture contained, in total volume of 50 µL, 5 µL of Advantage® 2 PCR Buffer, 200 µM dNTPs, 200 nM each oligonucleotide primer, 5 µL of 200 fold diluted cDNA, 1 µL of Advantage® 2 Polymerase Mix. The following conditions were used for the amplifications: 3 minutes of denaturation at 94° C.; 15 cycles of 1 minutes denaturation at 94° C., 1 min of annealing at 65° C. for the first cycle and minus one degree for each following cycle, and 2 minutes extension at 72° C.; 20 cycles of 1 minutes denaturation at 94° C., 1 min of annealing at 58° C. and 2 minutes extension at 72° C.; and finally 10 minutes extension at 72° C. Different PCR were performed with the possible combinations of sense and anti-sense oligonucleotides. The amplicons were screened for the expected sizes and for sequence homology to diterpene synthases. Unfortunately, using this PCR approach, no diterpene-related sequence could be obtained.

Example 5

Massively Parallel Sequencing of a *S. sclarea* Flower cDNA Library.

Since the classical homology-based cloning approach did not succeed in the cloning of class I diterpene synthase from *S. sclarea*, we undertook to use an approach based on the global sequencing of the cDNA library. We used the technology of massive parallel sequencing of small DNA fragments developed by Illumina (San Diego, Calif.) to obtain sequence information of all the transcripts (transcriptome) present in the *Salvia sclarea* flowers. This sequencing technique uses a reversible terminator-based sequencing chemistry and the Cluster Station and Genome Sequencer apparatuses developed by Solexa and Illumina.

The technology and equipment was set up at Fasteris SA (Geneva, Switzerland) and the preparation of the DNA samples and the sequencing were performed by Fasteris SA. An aliquot (1 µg) of the cDNA library generated from *S. sclarea* developping flowers and using the Marathon™ cDNA Amplification Kit (Clontech, Mountain View, Calif.) (Example 1), was treated using the Genomic Sample Prep Kit (Illumina). Briefly, the DNA is fragmented by nebulization, the ends are repaired to generate blunt ends, adapters are ligated to the ends of the DNA fragments and the adapter-modified DNA fragments are amplified by PCR. After controlling the quality of the library by gel electrophoresis, the generation of the DNA clusters on the flow cell and the sequencing reaction is performed on the Cluster Station and Genome Sequencer equipments. Using this technology, 1.9 millions of short sequences (reads) of 35 bases were obtained.

The Edena software (Dr David Hernandez, Genomic Research Laboratory, University of Geneva Hospitals, Geneva, Switzerland) was used to reassemble contiguous sequences. The five last bases were first removed from each read because of possible miss-incorporations due to the lower fidelity in the last cycles of the sequencing procedure. The parameters of the software were set such as to allow 15 bases minimum length for the overlaps with strict (100%) identity. The contigs (contiguous sequences) with a length of at least 50 bases were retained. In these conditions, 2054 contigs of 50 to 1330 bases in length could be reconstituted.

To evaluate the quality of the assembling, the contigs were searched for sequence identity with the DNA sequence of SsLPPs, the class II diterpene synthases first isolated from the *S. sclarea* cDNA library (SsLPPs3 (SEQ ID NO:22), Example 2). This search was performed using the BLASTn method (Altschul et al, *J. Mol. Biol.* 215, 403-410, 1990). Surprisingly, only 3 contigs of lengths of 81, 73 and 52 bases were found and only forty reads had been used by the Eland software to generate these contigs. Alignment with the SsLPPs3 reference sequence showed that the 3 contigs (SEQ ID NO:33 to 35 covered only 8.7% of the full-length sequence although with an identity of 99%).

Very limited sequence information has been reported in the public databases for *Salvia sclarea*. The only gene sequence available from the NCBI database was the sequence of the large subunit of the ribulose-1,5-bisphosphate carboxylase (RuBisCO) from *salvia sclarea* (NCBI access No. Z37450). Search of the contigs for DNA identity with this *S. sclarea* RuBisCO DNA sequence (BLASTn Search) provided two contigs of 870 and 547 bases respectively (SEQ ID NO:36 and 37). Alignment of the two contigs with the RuBisCO sequence showed coverage of 98%: only 27 bases (between position 858 and 884) out of 1420 bases were not present in the contigs. In addition to this almost complete coverage, the identity between the reference sequence and the contigs was 99.5%, representing a difference of only 7 nucleotides.

All reads (non-assembled data) were then searched for sequence identity with the SsLPPs3 sequence (SEQ ID NO:22). The Eland software (Illumina) was used to perform this search allowing a maximum of 2 mismatches with the reference sequence. A total of 616 reads where recovered. Alignment of the selected fragments with the reference sequence revealed that the SsLPPs3 sequence (SEQ ID NO:22) was covered on the whole length with a slightly higher coverage (more reads) towards the 3' end. The same manipulation with the RuBisCO sequence showed that 1650 reads were obtained for this sequence. The coverage of the reference sequence with the reads was much higher for the RuBisCo than for SsLPPs3 (SEQ ID NO:22). For SsLPPs3 (SEQ ID NO:22), several small regions with no coverage and regions with sequence ambiguity between reads were found. This incomplete coverage prevents the complete re-assembling and is certainly the reason for the generation of only a few very small contigs.

The number of reads obtained for a given cDNA is proportional to the abundance of this cDNA. Thus, relative abundances can be estimated by dividing the number of reads obtained for given cDNAs by their total lengths. Performing this calculation for the RuBisCO and SsLPPs3 (SEQ ID NO:22) gave values of 1160 and 260 reads/Kb respectively, reflecting a 4.5 higher abundance of the RuBisCO cDNA relative to the SsLPPs cDNAs. The RubisCo is an enzyme involved in the primary metabolism of plants and catalyzing the fixation of carbon in the Calvin cycle. The higher relative abundances of the RuBisCO reflects a high representation of genes involved in primary metabolisms compared to gene involved in secondary metabolism such as diterpene synthesis. BLAST search analysis with the contigs showed that other enzymes from the Calvin cycles (e.g. phosphoglycerate kinase, glyceraldehyde 3-phosphate dehydrogenase, triose-phosphate isomerase) and primary metabolism were also abundantly represented in the cDNA library used herein. Thus, the cDNA coding for the enzymes involved in secondary metabolism and particularly in diterpene biosynthesis were in too low abundance to obtain a sufficient coverage and complete reassembling.

Example 6

Extraction of Class I Diterpene Synthases-Like Sequences from the Sequencing Data.

The Blast algorithm (Altschul et al, *J. Mol. Biol.* 215, 403-410, 1990) was used to search for homology of the deduced amino acid sequences with class I diterpene synthases sequences.

A Blastx search against a protein database was first performed with the 2054 contigs. This search provided only one contig (contig1610, SEQ ID NO:38) presenting sequence homology with class I diterpene synthases. The amino acid sequence deduced from this contig contained the DDxxD motif characteristic of ionization-initiated cyclization of pre-nyl-diphosphates.

A fraction of the row data, representing approximately $3 \times 10^5$ reads was then search for homology with class I diterpene synthases. The reads were search using the tBlastn algorithm with five selected class I diterpene synthase amino acid sequences (NCBI accession numbers AAC39443, BAB19275, BAB12441, AAD34295, AAS98912). This search selected 462 reads, which were then processes using the CAP program (Huang, Genomics 14(1), 18-25, 1992) to identify overlapping sequences. A small portion of the reads could be assembled in short contigs of maximum length of 111 bases. These contigs as well as the remaining isolated reads were used for Blastx search against a protein database to confirm their identity with class I diterpene synthases. Finally, 5 DNA fragments were retained (SEQ ID NO:39 to 43).

Figure 3A:
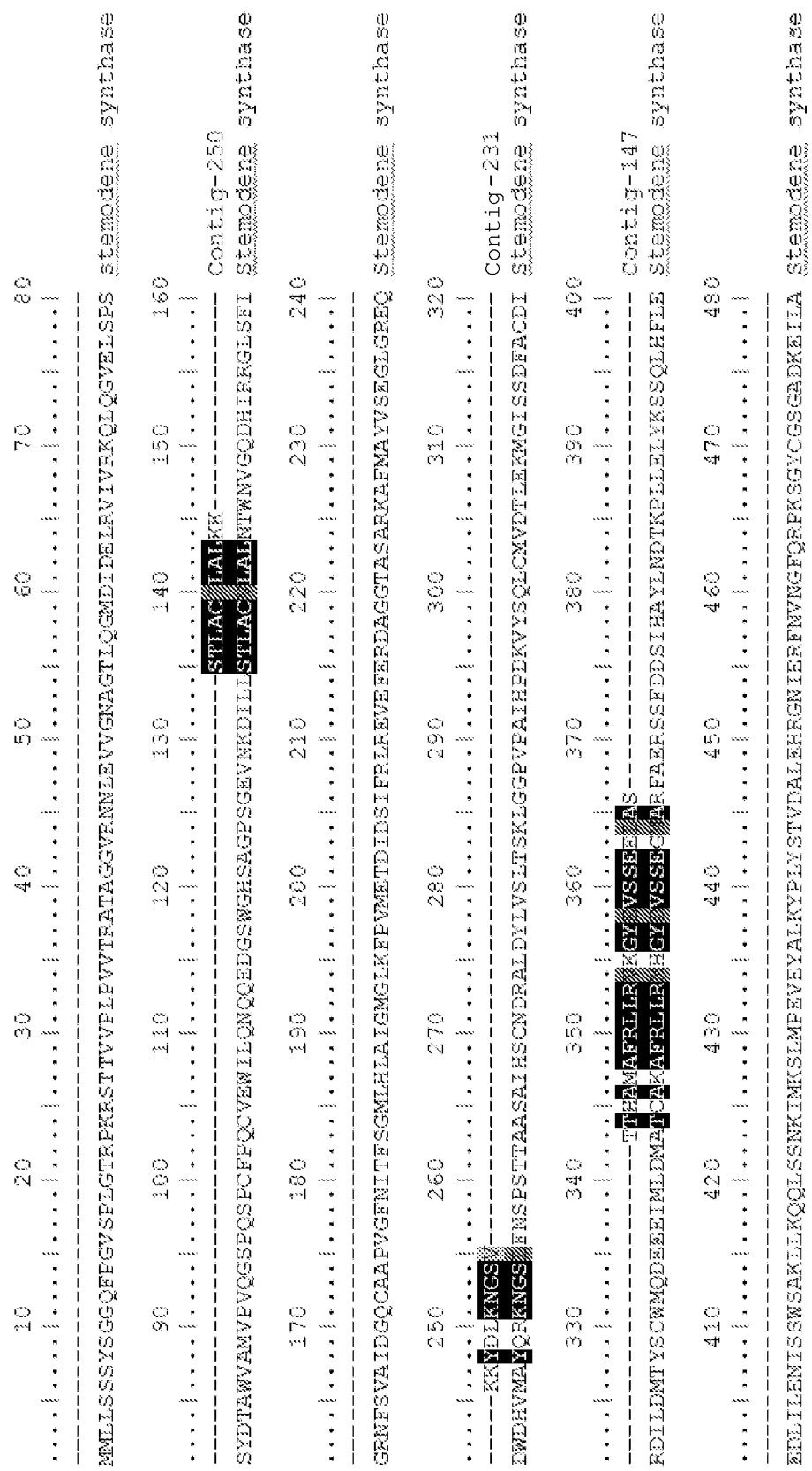
Figure 4B:
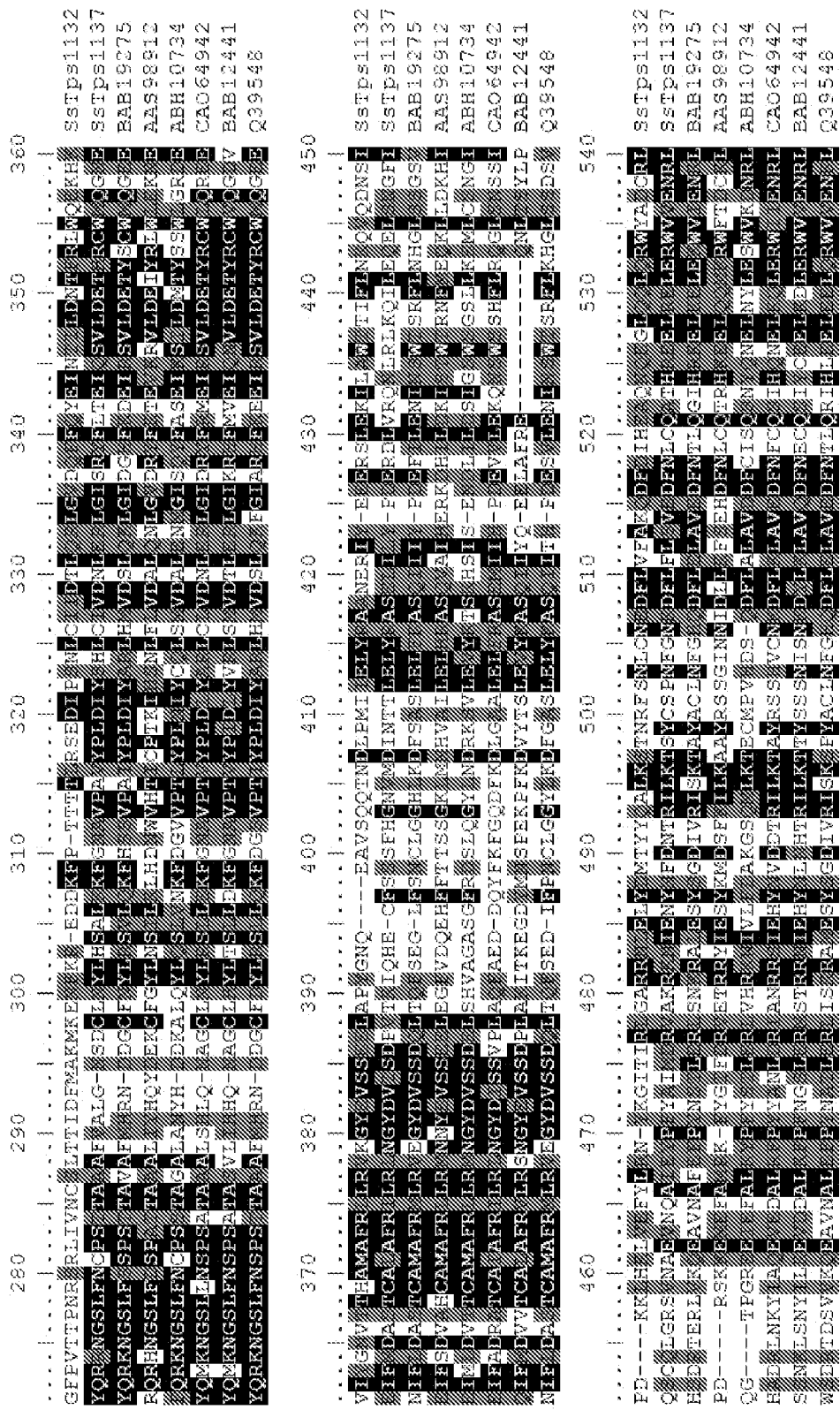

The amino acid sequences were deduced from the selected fragments (SEQ ID NO:44 to 48, and SEQ ID NO:104) and were aligned with references diterpene synthases sequences, allowing their relative positioning. FIGS. 3A-3B show an alignment of these sequences with a full-length diterpene synthase sequence, the stemodene synthase from *Oriza sativa* (Morrone et al, 2006; NCBI access No. AAZ76733) taken as reference.

Example 7

PCR Amplification of Full-Length Class I Diterpene Synthases cDNAs.

A set of forward and reverse oligonucleotides was deduced from the diterpene synthases-related DNA sequences selected from the sequencing of the *S. sclarea* cDNA library (Example 6). These primers were used in combination with cDNA adaptor primers in 3'/5'RACE type PCR amplifications. The amplifications were performed using the *S. sclarea* cDNA library, prepared as described above in Example 1, following the Marathon™ cDNA Amplification Kit protocol (Clontech, Mountain View, Calif.). The thermal Cycling conditions were as follows: 1 min at 94° C., 5 cycles of 30 sec at 94° C. and 4 min at 72° C., 5 cycles of 30 sec at 94° C. and 4 min at 70° C., 20 cycles of 30 sec at 94° C. and 4 min at 68° C.

Using the Cont250-Fwd primer (SEQ ID NO:49) a 547 bp DNA sequence (1130Cont250, SEQ ID NO:81) was obtained. Analysis of the sequence revealed that it corresponded to the 5'end of a diterpene synthase cDNA and contained 348 bp of the coding region. With the primer Cont147_fw1 (SEQ ID NO:51) and Cont147_fw2 (SEQ ID NO:52) we obtained a 1473 bp sequence (1132Cont147, SEQ ID NO:82) containing the 3'end and 1293 bp of the coding region of a diterpene synthase cDNA. The Cont224_fw primer (SEQ ID NO:57) provided a 207 bp DNA fragment (1137Cont224, SEQ ID NO:83) encoding for the 43 C-terminal amino acids of a diterpene synthases with a sequence distinct from 1132Cont147 (SEQ ID NO:82). The Cont147rev1 (SEQ ID NO:53) and Cont147_rev2 (SEQ ID NO:54) primers allowed the amplification of a 464 bp DNA fragment (1134Cont147, SEQ ID NO:84). The deduced amino acid showed homology with diterpene synthases but alignment with other diterpene synthases sequences suggested that 200 to 300 codons where still missing to reach the 5'end. All the sequences obtained by this series of amplification differed significantly from the sequences of SsLPPs previously isolated (SEQ ID NO:22 and 23). PCR with the other primers deduced from the diterpene synthases-related DNA sequences (primers cont224-rev (SEQ ID NO:58), cont250-rev (SEQ ID NO:50), cont33-fw1 (SEQ ID NO:55) and cont33-rev (SEQ ID NO:56)) did not provide diterpene synthase related sequences.

From the only sequence containing an obvious translation initiation region of a diterpene synthase (1130Cont250, SEQ ID NO:81), sense oligonucleotides were deduced from the 5' untranslated region (UTR) (1130-fw1 (SEQ ID NO:59) and 1130-fw2 (SEQ ID NO:60) and from the 5'end of the open reading frame (ORF) (1130-fw3, SEQ ID NO:61). From the two sequences containing the stop codon region of two distinct diterpene synthases (1132Cont147 (SEQ ID NO:82) and 1137Cont224 (SEQ ID NO:83)), reverse-sense primers were deduced either from the 3' UTR (1132-rev1 (SEQ ID NO:65) and 1137-rev1 (SEQ ID NO:62)) or from the 3' end of the open reading frame (1132-rev2 (SEQ ID NO:64) and 1137-rev2 (SEQ ID NO:63)). PCR were performed with different combinations of these forward and reverse primers. The combination of primers deduced from the 1130Cont250 (SEQ ID NO:81) sequence with the primers deduced from the 1137Cont224 (SEQ ID NO:83) sequence produced a fragment of 2388 bp (SEQ ID NO:85) coding for a protein of 795 amino acids (SsTps1137, SEQ ID NO:86)). Comparison with published sequences showed homologies with class I diterpene synthases and particularly ent-kaurene synthases B. Highest homology was with an uncharacterized protein from *Vitis vinifera* (NCBI access No. CAO64942, 59% identity), an ent-kauren synthase from *Cucumis sativus* (NCBI access No. BAB19275, 54% identity) and an ent-kauren synthase from *Lactuca sativa* (NCBI access No. BAB12441, 54% identity). The SsTps1137 (SEQ ID NO:86) amino acid sequence contained a DDFFD motif typical of ionization-dependent (class I) terpene synthases and did not contain the characteristic class II motif.

The combination of the same forward primers with the reverse primers deduced from the 1132Cont147 (SEQ ID NO:82) did not allow the amplification of any fragment, confirming that these two sequences did not arise from the same cDNA. A 5'RACE approach was then used to identify the 5'end of the ORF corresponding to the 1132Cont147 sequence (SEQ ID NO:82). Using the primers 1132_race1 (SEQ ID NO:67) and 1132_race2 (SEQ ID NO:68), a 536 bp sequence (1132RACE, SEQ ID NO:87) was obtained which had 41 bases overlap with the 1132Cont147 fragment (SEQ ID NO:82). This RACE product was identical to the previously obtained 1134Cont147 sequence (SEQ ID NO:84) and no extension at the 5'end was observed. As observed previously, this sequence had homology with diterpene synthases but seemed shorter by at least 200 codons than all other published diterpene synthases sequences. 5'RACE experiments were performed, in order to try to extend the sequence toward the 5'end of the 1132Cont147 sequence (SEQ ID NO:82) and to identify the true translation initiation codon. Several sets of oligonucleotides (1132_race3 to 1132_race9, SEQ ID NO:69 to 75) were designed but no additional sequence information was obtained. This led us to suppose that one of the ATG codon in the 1134Cont147 sequence (SEQ ID NO:84) was actually the initiation codon of the corresponding diterpene synthase gene. The nucleotidic sequence of this putative diterpene synthase (named SsTps1132, SEQ ID NO:2) was reconstituted from the 1132Cont147 (SEQ ID NO:82) and 1132RACE (SEQ ID NO:87) sequences. Taking the first ATG, the 1728 bp ORF of SsTps1132 (SEQ ID NO:2) encoded for a 575 amino acid protein (SEQ ID NO:1). This protein contained the ionization-dependent modif (DDFFD) and shared homology, but relatively low, with published diterpene synthases; the closest sequence being a terpene synthase from *Nicotiana tabacum* (NCBI acces No. AAS98912), with 37% identity.

Surprisingly, the identity between the SsTps1137 (SEQ ID NO:86) and SsTps1132 (SEQ ID NO:1) proteins was only 30% and these sequences shared only 21 to 23% identity with the class II SsLPPs first isolated from *S. sclarea* (SEQ ID NO:24 and 25, Examples 1-3). An alignment of these two proteins with selected diterpene synthases sequences BAB19275 (SEQ ID NO:106), AAS98912 (SEQ ID NO:107), ABH10734 (SEQ ID NO:108), CAO64942 (SEQ ID NO:109), BAB12441 (SEQ ID NO:110), and Q39548 (SEQ ID NO:111) is presented in FIGS. 4A-4D. The alignment shows that SsTps1132 (SEQ ID NO:1) is truncated at the N-terminal end by 150 to 240 amino acids compared to the other diterpene synthases. The ChloroP method (Emanuelsson et al, *Protein Science* 8, 978-984, 1999) was used to predict the presence of a chloroplast transit peptide in each protein sequence. For SsTps1137 (SEQ ID NO:86) and SsTps1132 (SEQ ID NO:1) chloroplast transit peptides of 22 and 51 amino acids respectively were predicted, arguing for a chloroplast localization of both proteins.

Search of all reads for sequences identical to the SsTps1137 (SEQ ID NO:85) and SsTps1132 (SEQ ID NO:2) DNA sequences, provided only 24 reads for SsTps1137 and 425 reads for SsTps1132. This difference in the number of reads generated from each transcript reflects a significant difference in the expression levels. Based on the relative number of reads obtained for each transcript, it can be estimated that the expression level of SsTps1132 (220 reads/Kb) was similar to the expression level of SsLPPs (260 reads/Kb) and that SsTps1137 was expressed at a much lower level (10 reads/Kb). With the assumption that enzymes catalyzing steps in the same metabolic pathway are generally expressed at a similar level, it can be speculated that SsTps1132 (SEQ ID NO:1) rather than SsTps1137 (SEQ ID NO:86) is involved in the same metabolic pathway as SsLPPs.

The contigs generated with the Edena software (Example 5) were searched for DNA sequences identical to the sequences of these two new putative class I diterpene synthases. For SsTps1137 (SEQ ID NO:85) no contig was found in accordance with the presumed low expression level of this enzyme. For SsTps1132 (SEQ ID NO:2), 4 contigs where found. The previously identified contig1610 (SEQ ID NO:38) and three additional contigs (of length of 53 to 96 bp) (SEQ ID NO:88 to 90) not previously identified as fragment of a diterpene synthase. Blastx search with these three sequences did not show homology with known protein sequences. The failure in finding homology for these contigs is due to the short lengths of these fragments and to the low homology of SsTps1132 (SEQ ID NO:1) with the diterpene synthases present in the databases. The observation of an N-terminal deletion of SsTps1132 (SEQ ID NO:1) compared to the other diterpene synthases also explains afterwards why the PCR approach first employed did not succeed. Indeed, the forward primers were designed from conserved regions present in the first 150 amino acids of diterpene synthases, a region absent in SsTps1132 (SEQ ID NO:1). The SsTps1137 sequence (SEQ ID NO:86) contains the conserved motifs used to design the primers and the corresponding DNA sequences are complementary to the primer sequences. Presumably, the amplification of SsTps1137 (SEQ ID NO:85) did not succeed in the PCR approach because of the low abundance of this transcript.

Example 8

Heterologous Expression of the *S. Sclarea* Class I Diterpene Synthases in *E. coli*.

To assign an enzymatic activity to SsTps1137 (SEQ ID NO:86) and SsTps1132 (SEQ ID NO:1), the recombinant proteins were expressed in *E. coli*. The full-length cDNAs were inserted into the pet101/D-TOPO vector using the Champion pET101 Directional TOPO Expression Kit.

For each enzyme, two constructs were prepared: one to express the full-length protein and one to express a truncated protein based on the chloroplast transit peptide prediction. The full-length SsTps1137 (SEQ ID NO:85) and SsTps1132 (SEQ ID NO:2) open reading frames were amplified from the cDNA library using the primer pairs 1137-start (SEQ ID NO:78) with 1137-stop (SEQ ID NO:80) and 1132-start1 (Seq ID No 76) with 1132-stop (SEQ ID NO:66) respectively. The primers 1137_start2 (SEQ ID NO:79) and 1137_stop (SEQ ID NO:80) were used to amplify a 72 bp truncated version of SsTps1137 designed to express the protein with 24 amino acids deleted at the N-terminal end. In the same manner, the primers 1132_start2 (SEQ ID NO:77) and 1132-stop (SEQ ID NO:66) were used to prepare a truncated version of SsTps1132 designed to express the protein with a 50 amino acid N-terminal deletion. All amplifications of cDNA for expression of the expression constructs were performed using the Pfu DNA polymerase (Promega), in a final volume of 50 µl containingti 5 µl of Pfu DNA polymerase 10× buffer, 200 µM each dNTP, 0.4 µM each forward and reverse primer, 2.9 units Pfu DNA polymerase and 5 µl of 100-fold diluted cDNA (prepared as described herein in Example 1 using the Marathon™ cDNA Amplification Kit (Clontech)). The thermal cycling conditions were as follows: 1.5 min at 95° C.; 30 cycles of 45 sec at 95° C., 30 sec at 58° C. and 5 min at 72° C.; and 10 min at 72° C.

Figure 5:
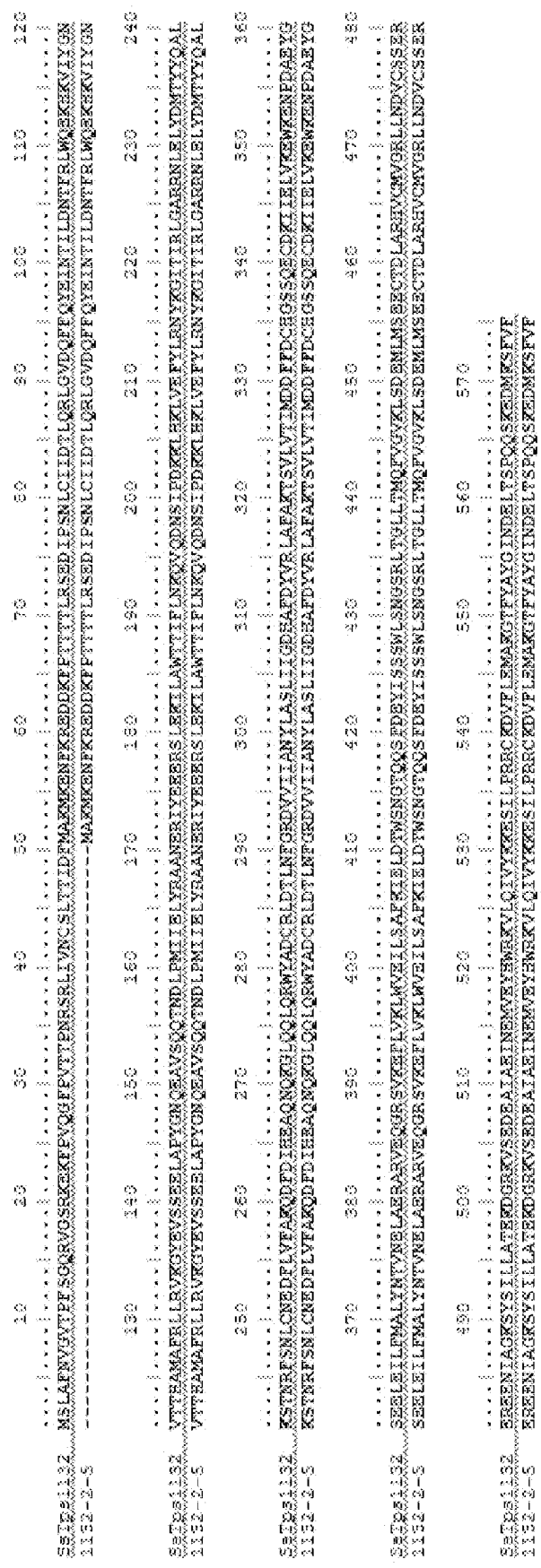
FIG. 5: Alignment of the amino acid sequences of SsTps1132 (SEQ ID NO:1) and 1132-2-5 (SEQ ID NO:96) which were heterologously expressed in E. coli.

After the ligation in the pET101 vector, several clones were selected for each construct and were sequenced to ensure that no mutation had been introduced during the PCR amplification. For SsTps1137 the two constructs 1137-B12 (SEQ ID NO:91) and 1137-2-B12 (SEQ ID NO:92) were selected containing the SsTps1137 cDNA respectively with and without the peptide signal (corresponding polypeptide sequences are SEQ ID NO:94 and 95). For SsTps1132, two constructs were selected: one with the complete sequence of SsTps1132 (SEQ ID nO:2) and a construct without peptide signal (1132-2-5, SEQ ID NO:93). The alignment of the two amino acid sequences (SEQ ID NO:1 and 96) deduced from these constructs is shown in FIG. 5.

The plasmids pET101-1137-B12, pET101-1137-2-B12, pET101-SsTps1132, and pET101-1132-2-5 were transferred into B121(DE3) *E. coli* cells (Novagene, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g), and the supernatants containing the soluble proteins were used for further experiments. The crude protein extracts were analysed by SDS-PAGE and compared to protein extracts obtained from cells transformed with the empty pET101 plasmid.

Example 9

Enzymatic Activity of the Recombinant *S. Sclarea* Class I Diterpene Synthases in *E coli*.

The crude *E. coli* protein extracts containing the recombinant proteins and prepared as described in Example 8 were used for the characterization of the enzymatic activities. The enzymatic assays were performed as described in Example 3. All assays were performed in 50 mM MOPSO pH 7, 10% glycerol, 1 mM DTT.

Figure 6:
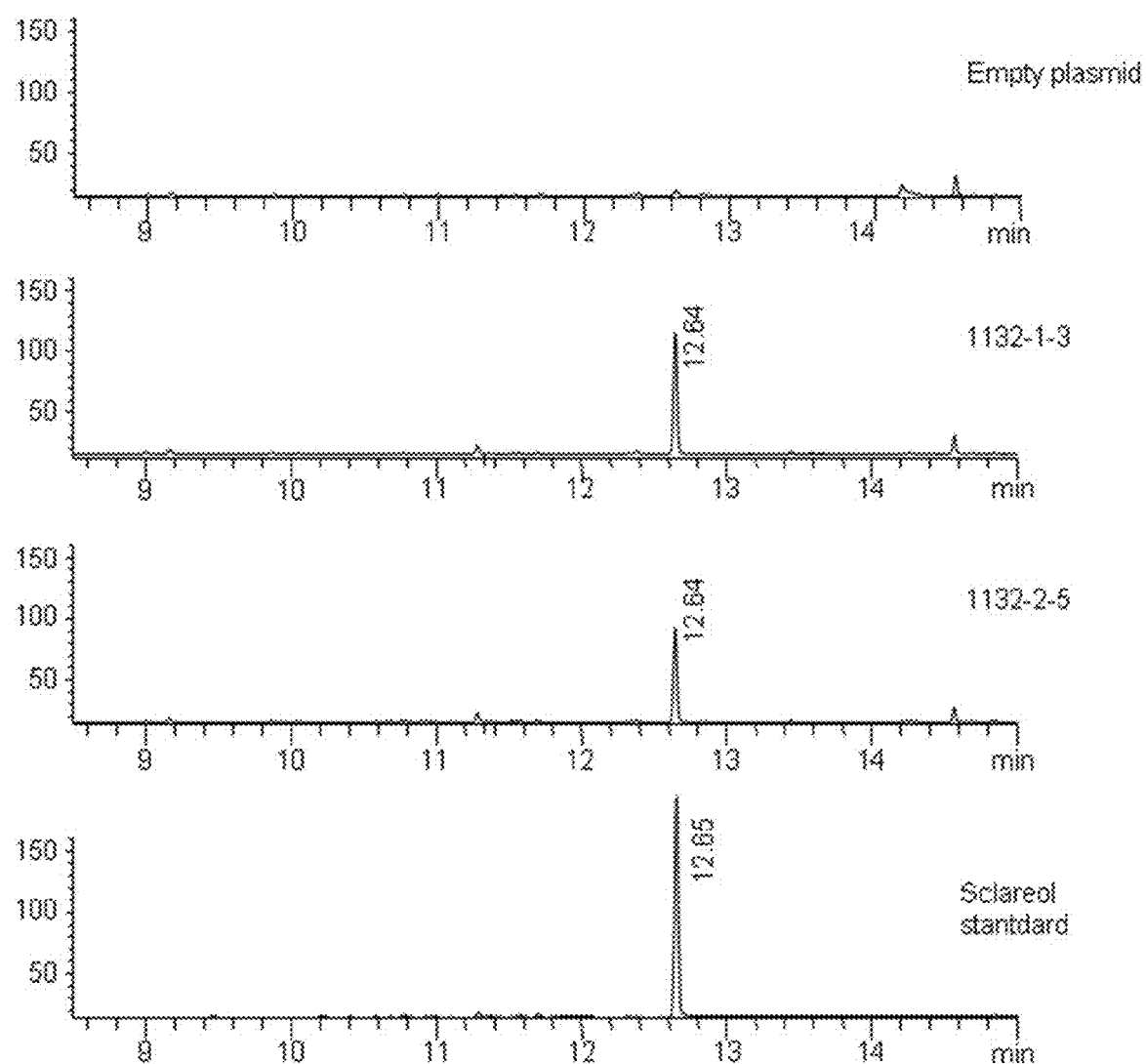
FIG. 6: GC analysis of the products obtained after incubation of the different 1132 recombinant proteins with LPP. Crude protein extracts from E. coli expressing the recombinant SsTps1132 and 1132-2-5 proteins (SEQ ID NO:1 and 96) were incubated with LPP in a in a final volume of 1 mL 50 mM MOPSO pH 7 supplemented with 15 mM $MgCl_2$ and 1 mM DTT.
Figure 7:
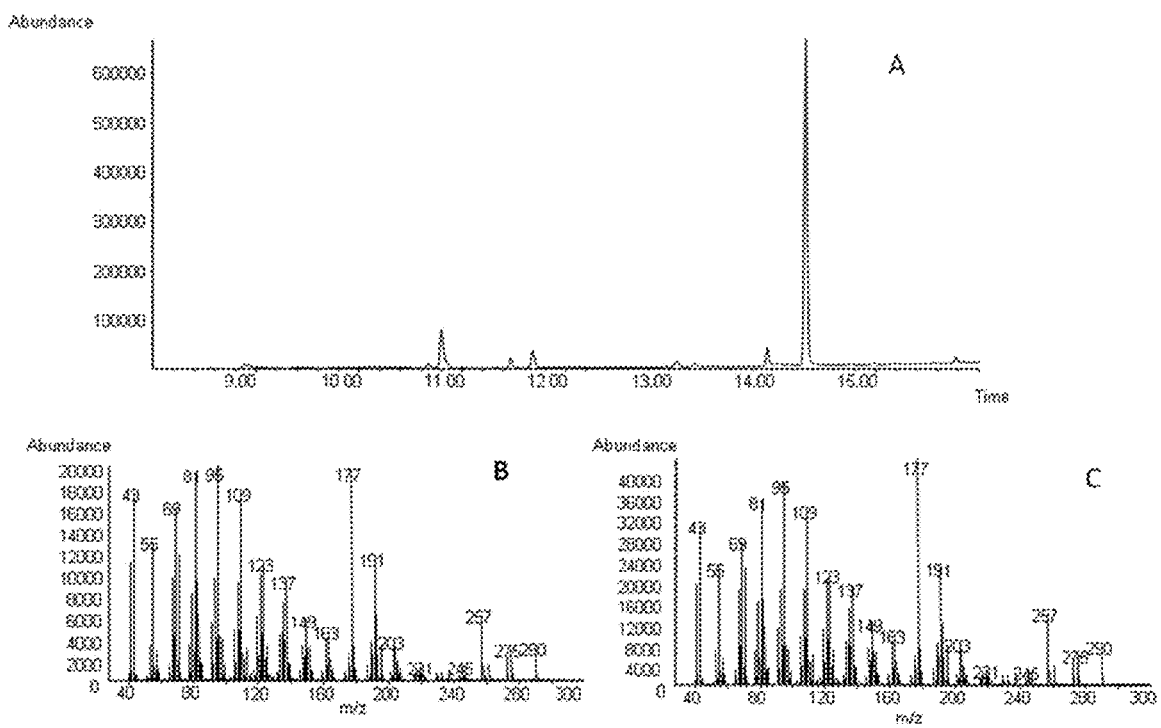
FIG. 7: GC-MS analysis of the products generated from LPP by the recombinant 1132-2-5 protein. (A) Total ion chromatogram of the products obtained from the incubation of LPP with a crude protein extract from E. coli transformed with pET101-1132-2-5 (SEQ ID NO:93). (B) Mass spectrum of the peak at retention time of 14.3. (C) Mass spectrum of an authentic sclareol standard.

The enzymatic activities were first evaluated using as substrate either GGPP or LPP, the product of SsLPPs (SEQ ID NO:22) and the presumed intermediate in the biosynthesis of sclareol (Examples 1 to 3). GGPP was synthesized as described by Keller and Thompson (*J. Chromatogr* 645(1), 1993, 161-167) and LPP was prepared enzymatically as described in Example 3. The assays were performed in the presence of 10 to 100 µM of substrate, 15 mM $MgCl_2$ and 0.1 to 0.5 mg of crude protein in a total volume of 1 mL. The tubes were incubated 4 to 12 hours at 30° C. and extracted twice with one volume of pentane. After concentration under a nitrogen flux, the extracts were analysed by GC and GC-MS (using the conditions described in Example 3) and compared to extracts from assay with control proteins (obtained from cells transformed with the empty plasmid). With GGPP as substrate, no activity was observed with any of recombinant proteins (data not shown). With LPP as substrate, no activity was observed with the proteins extracts containing SsTps1137 recombinant proteins but with SsTps1132, activity was observed with both SsTps1132 and 1132-2-5 (SEQ ID NO:1 and 96) (FIG. 6). The enzymes were also active in the absence of $MgCl_2$ and the same product profiles were observed with an overall activity roughly the same. The identity of product was confirmed by concordance of the retention times (FIG. 6) and matching of the mass spectrum with the spectrum of an authentic standard (FIG. 7). In all assays, a single peak of sclareol was observed with no trace of additional product.

Figure 8:
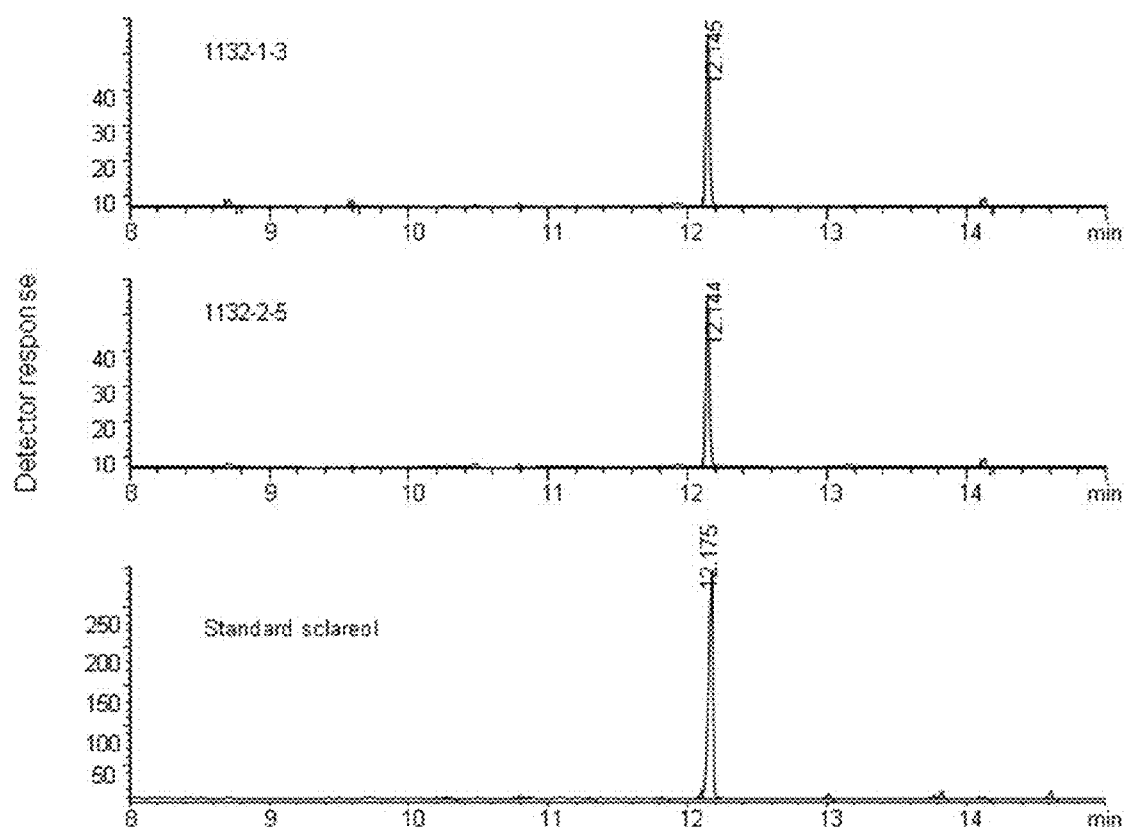
FIG. 8: GC analysis of the products obtained after co-incubation of SsTps1132 and 1132-2-5 recombinant proteins (SEQ ID NO:1 and 96) with the SsLPPs3 (SEQ ID NO:24) recombinant protein in the presence of GGPP.

Assays were then performed with co-incubation of the class II diterpene synthases (SsLPPs3, SEQ ID NO:24; Examples 1-3) and the class I diterpene synthases (1132 series, SEQ ID NO:1 and 96). Assays were performed in 50 mM MOPSO pH 7, 10% glycerol, 1 mM DTT, 50 µM GGPP, with 1 mM MgCl$_2$ and in the presence of 50 µL of the crude protein extracts from *E. coli* expressing the different constructs. Thus assays in the presence of 50 µL of crude protein extracts containing the SsLPPs3 (SEQ ID NO:24) recombinant enzyme and 50 µL of extracts containing SsTps1132 (SEQ ID NO:1) or 1132-2-5 (SEQ ID NO:96) were evaluated for the production of diterpene products. FIG. 8 shows the GC profiles of extracts from such incubations in the presence of MgCl$_2$. Sclareol was produced with both 1132 constructs (SEQ ID NO: 1 and 96) (FIG. 8), a result consistent with the assay described above with LPP as substrate. No significant difference was observed when omitting MgCl$_2$ from the incubations (data not shown).

In conclusion the SsTps1132 (SEQ ID NO:2) encodes for the sclareol synthase (SEQ ID NO:1) and catalyses the conversion of LPP to sclareol.

The invention claimed is:

1. A method for producing sclareol comprising
a) contacting labdenediol diphosphate (LPP) with an isolated polypeptide having a sclareol synthase activity and comprising the amino acid sequence of SEQ ID NO:1; and
b) optionally, isolating the sclareol produced in step a).

2. The method of claim 1, wherein said polypeptide consists of the amino acid sequence set out in SEQ ID NO:1.

3. The method of claim 1 wherein step a) is carried out by cultivating a non-human organism or cell capable of producing LPP and transformed to express said polypeptide under conditions conducive to the production of sclareol.

4. The method of claim 3, further comprising, prior to step a), transforming the non human organism or cell capable of producing LPP with a nucleic acid encoding said polypeptide, so that said organism expresses said polypeptide.

5. The method of claim 3 or 4, wherein said non-human organism is a plant, a prokaryote or a fungus.

6. The method of claim 3 or 4, wherein said non-human organism is a microorganism.

7. The method of claim 6, wherein said microorganism is a bacteria or yeast.

8. The method of claim 7, wherein said bacteria is *E. coli* and said yeast is *Saccharomyces cerevisiae*.

9. The method of claim 3 or 4, wherein said non-human cell is a higher eukaryotic cell selected from plant cells or fungal cells.

* * * * *

SEQUENCE LISTING

```
<160> NUMBER OF SEQ ID NOS: 111

<210> SEQ ID NO 1
<211> LENGTH: 575
<212> TYPE: PRT
<213> ORGANISM: Salvia sclarea

<400> SEQUENCE: 1

Met Ser Leu Ala Phe Asn Val Gly Val Thr Pro Phe Ser Gly Gln Arg
1               5                   10                  15

Val Gly Ser Arg Lys Glu Lys Phe Pro Val Gln Gly Phe Pro Val Thr
            20                  25                  30

Thr Pro Asn Arg Ser Arg Leu Ile Val Asn Cys Ser Leu Thr Thr Ile
        35                  40                  45

Asp Phe Met Ala Lys Met Lys Glu Asn Phe Lys Arg Glu Asp Asp Lys
    50                  55                  60

Phe Pro Thr Thr Thr Thr Leu Arg Ser Glu Asp Ile Pro Ser Asn Leu
65                  70                  75                  80

Cys Ile Ile Asp Thr Leu Gln Arg Leu Gly Val Asp Gln Phe Phe Gln
                85                  90                  95

Tyr Glu Ile Asn Thr Ile Leu Asp Asn Thr Phe Arg Leu Trp Gln Glu
            100                 105                 110

Lys His Lys Val Ile Tyr Gly Asn Val Thr Thr His Ala Met Ala Phe
        115                 120                 125

Arg Leu Leu Arg Val Lys Gly Tyr Glu Val Ser Ser Glu Glu Leu Ala
    130                 135                 140

Pro Tyr Gly Asn Gln Glu Ala Val Ser Gln Gln Thr Asn Asp Leu Pro
145                 150                 155                 160

Met Ile Ile Glu Leu Tyr Arg Ala Ala Asn Glu Arg Ile Tyr Glu Glu
                165                 170                 175

Glu Arg Ser Leu Glu Lys Ile Leu Ala Trp Thr Thr Ile Phe Leu Asn
            180                 185                 190

Lys Gln Val Gln Asp Asn Ser Ile Pro Asp Lys Lys Leu His Lys Leu
        195                 200                 205

Val Glu Phe Tyr Leu Arg Asn Tyr Lys Gly Ile Thr Ile Arg Leu Gly
    210                 215                 220

Ala Arg Arg Asn Leu Glu Leu Tyr Asp Met Thr Tyr Tyr Gln Ala Leu
225                 230                 235                 240

Lys Ser Thr Asn Arg Phe Ser Asn Leu Cys Asn Glu Asp Phe Leu Val
                245                 250                 255

Phe Ala Lys Gln Asp Phe Asp Ile His Glu Ala Gln Asn Gln Lys Gly
            260                 265                 270

Leu Gln Gln Leu Gln Arg Trp Tyr Ala Asp Cys Arg Leu Asp Thr Leu
        275                 280                 285
```

Asn Phe Gly Arg Asp Val Val Ile Ile Ala Asn Tyr Leu Ala Ser Leu
    290                 295                 300

Ile Ile Gly Asp His Ala Phe Asp Tyr Val Arg Leu Ala Phe Ala Lys
305                 310                 315                 320

Thr Ser Val Leu Val Thr Ile Met Asp Asp Phe Phe Cys His Gly
                325                 330                 335

Ser Ser Gln Glu Cys Asp Lys Ile Ile Glu Leu Val Lys Glu Trp Lys
            340                 345                 350

Glu Asn Pro Asp Ala Glu Tyr Gly Ser Glu Glu Leu Glu Ile Leu Phe
        355                 360                 365

Met Ala Leu Tyr Asn Thr Val Asn Glu Leu Ala Glu Arg Ala Arg Val
    370                 375                 380

Glu Gln Gly Arg Ser Val Lys Glu Phe Leu Val Lys Leu Trp Val Glu
385                 390                 395                 400

Ile Leu Ser Ala Phe Lys Ile Glu Leu Asp Thr Trp Ser Asn Gly Thr
                405                 410                 415

Gln Gln Ser Phe Asp Glu Tyr Ile Ser Ser Ser Trp Leu Ser Asn Gly
            420                 425                 430

Ser Arg Leu Thr Gly Leu Leu Thr Met Gln Phe Val Gly Val Lys Leu
        435                 440                 445

Ser Asp Glu Met Leu Met Ser Glu Glu Cys Thr Asp Leu Ala Arg His
    450                 455                 460

Val Cys Met Val Gly Arg Leu Leu Asn Asp Val Cys Ser Ser Glu Arg
465                 470                 475                 480

Glu Arg Glu Glu Asn Ile Ala Gly Lys Ser Tyr Ser Ile Leu Leu Ala
                485                 490                 495

Thr Glu Lys Asp Gly Arg Lys Val Ser Glu Asp Glu Ala Ile Ala Glu
            500                 505                 510

Ile Asn Glu Met Val Glu Tyr His Trp Arg Lys Val Leu Gln Ile Val
        515                 520                 525

Tyr Lys Lys Glu Ser Ile Leu Pro Arg Arg Cys Lys Asp Val Phe Leu
    530                 535                 540

Glu Met Ala Lys Gly Thr Phe Tyr Ala Tyr Gly Ile Asn Asp Glu Leu
545                 550                 555                 560

Thr Ser Pro Gln Gln Ser Lys Asp Met Lys Ser Phe Val Phe
                565                 570                 575

<210> SEQ ID NO 2
<211> LENGTH: 1728
<212> TYPE: DNA
<213> ORGANISM: Salvia sclarea

<400> SEQUENCE: 2
atgtcgctcg ccttcaacgt cggagttacg cctttctccg gccaaagagt tgggagcagg      60
aaagaaaaat ttccagtcca aggatttcct gtgaccaccc ccaataggtc acgtctcatc     120
gttaactgca gccttactac aatagatttc atggcgaaaa tgaaagagaa tttcaagagg     180
gaagacgata aatttccaac gacaacgact cttcgatccg aagatatacc ctctaatttg     240
tgtataatcg acaccccttca aaggttgggg tcgatcaat tcttccaata tgaaatcaac     300
actattctag ataacacatt caggttgtgg caagaaaaac acaaagttat atatggcaat     360
gttactactc atgcaatggc atttaggctt ttgcgagtga aggatacga agtttcatca     420 gaggagttgc ctccatatgg taaccaagag gctgttagcc agcaaacaaa tgacctgccg     480
atgattattg agctttatag agcagcaaat gagagaatat atgaagaaga gggagtctt      540

-continued

```
gaaaaaattc ttgcttggac taccatcttt ctcaataagc aagtgcaaga taactcaatt    600
cccgacaaaa aactgcacaa actggtggaa ttctacttga ggaattacaa aggcataacc    660
ataagattgg gagctagacg aaacctcgag ctatatgaca tgacctacta tcaagctctg    720
aaatctacaa acaggttctc taatttatgc aacgaagatt ttctagtttt cgcaaagcaa    780
gatttcgata tacatgaagc ccagaaccag aaaggacttc aacaactgca aggtggtat     840 gcagattgta ggttggacac cttaaacttt ggaagagatg tagttattat tgctaattat    900
ttggcttcat taattattgg tgatcatgcg tttgactatg ttcgtctcgc atttgccaaa    960
acatctgtgc ttgtaacaat tatggatgat tttttcgact gtcatggctc tagtcaagag   1020
tgtgacaaga tcattgaatt agtaaaagaa tggaaggaga atccggatgc agagtacgga   1080
tctgaggagc ttgagatcct tttatggcg ttgtacaata cagtaaatga gttggcggag    1140
agggctcgtg ttgaacaggg gcgtagtgtc aaagagtttc tagtcaaact gtgggttgaa   1200
atactctcag ctttcaagat agaattagat acatggagca atggcacgca gcaaagcttc   1260
gatgaataca tttcttcgtc gtggttgtcg aacggttccc ggctgacagg tctcctgacg   1320
atgcaattcg tcggagtaaa attgtccgat gaaatgctta tgagtgaaga gtgcactgat   1380
ttggctaggc atgtctgtat ggtcggccgg ctgctcaacg acgtgtgcag ttctgagagg   1440
gagcgcgagg aaaatattgc aggaaaaagt tatagcattc tactagcaac tgagaaagat   1500
ggaagaaaag ttagtgaaga tgaagccatt gcagagatca atgaaatggt tgaatatcac   1560
tggagaaaag tgttgcagat tgtgtataaa aagaaagca ttttgccaag aagatgcaaa    1620
gatgtatttt tggagatggc taagggtacg ttttatgctt atgggatcaa cgatgaattg   1680
acttctcctc agcaatccaa ggaagatatg aaatcctttg tcttttga               1728
```

<210> SEQ ID NO 3  
<211> LENGTH: 22  
<212> TYPE: DNA  
<213> ORGANISM: Artificial sequence  
<220> FEATURE:  
<223> OTHER INFORMATION: Forward primer  
<220> FEATURE:  
<221> NAME/KEY: misc_feature  
<222> LOCATION: (6)..(6)  
<223> OTHER INFORMATION: n is a, c, g, or t  
<220> FEATURE:  
<221> NAME/KEY: misc_feature  
<222> LOCATION: (15)..(15)  
<223> OTHER INFORMATION: n is a, c, g, or t  
<220> FEATURE:  
<221> NAME/KEY: misc_feature  
<222> LOCATION: (18)..(18)  
<223> OTHER INFORMATION: n is a, c, g, or t

<400> SEQUENCE: 3

```
gayrtngayg ayacngcnat gg                                              22
```

<210> SEQ ID NO 4  
<211> LENGTH: 24  
<212> TYPE: DNA  
<213> ORGANISM: Artificial sequence  
<220> FEATURE:  
<223> OTHER INFORMATION: Reverse primer  
<220> FEATURE:  
<221> NAME/KEY: misc_feature  
<222> LOCATION: (6)..(6)  
<223> OTHER INFORMATION: n is a, c, g, or t  
<220> FEATURE:  
<221> NAME/KEY: misc_feature  
<222> LOCATION: (9)..(9)  
<223> OTHER INFORMATION: n is a, c, g, or t

```
<220> FEATURE:
<221> NAME/KEY: misc_feature
<222> LOCATION: (15)..(15)
<223> OTHER INFORMATION: n is a, c, g, or t

<400> SEQUENCE: 4
gtyttnccna kccanacrtc ryyt                                          24

<210> SEQ ID NO 5
<211> LENGTH: 354
<212> TYPE: DNA
<213> ORGANISM: Salvia sclarea

<400> SEQUENCE: 5
gcgttaggct tctcaaaatg cacggatacg acgtcgatcc aaatgtacta aaacatttca    60
agcaacaaga tggtaaattt tcctgctaca ttggtcaatc ggtcgagtct gcatctccaa   120
tgtacaatct ttatagggct gctcaactaa gatttccagg agaagaagtt cttgaagaag   180
ccactaaatt tgcctttaac ttcttgcaag aaatgctagt caaagatcga cttcaagaaa   240
gatgggtgat atccgaccac ttatttgatg agataaagct ggggttgaag atgccatggt   300
acgccactct accccgagtc gaggctgcat attatctaga ccattatgct ggtt         354

<210> SEQ ID NO 6
<211> LENGTH: 29
<212> TYPE: DNA
<213> ORGANISM: Artificial sequence
<220> FEATURE:
<223> OTHER INFORMATION: Primer designed specifically for FN23

<400> SEQUENCE: 6
gcacggatac gacgtcgatc caaatgtac                                     29

<210> SEQ ID NO 7
<211> LENGTH: 27
<212> TYPE: DNA
<213> ORGANISM: Artificial sequence
<220> FEATURE:
<223> OTHER INFORMATION: Primer designed specifically for FN23

<400> SEQUENCE: 7
gggctgctca actaagattt ccaggag                                       27

<210> SEQ ID NO 8
<211> LENGTH: 29
<212> TYPE: DNA
<213> ORGANISM: Artificial sequence
<220> FEATURE:
<223> OTHER INFORMATION: Primer designed specifically for FN23

<400> SEQUENCE: 8
gggtgatatc cgaccactta tttgatgag                                     29

<210> SEQ ID NO 9
<211> LENGTH: 36
<212> TYPE: DNA
<213> ORGANISM: Artificial sequence
<220> FEATURE:
<223> OTHER INFORMATION: Adaptor sequence to extend oligodT primers

<400> SEQUENCE: 9
aattcggtac ccgggatcct tttttttttt tttttt                             36

<210> SEQ ID NO 10
<211> LENGTH: 19
```

-continued

```
<212> TYPE: DNA
<213> ORGANISM: Artificial sequence
<220> FEATURE:
<223> OTHER INFORMATION: Primer

<400> SEQUENCE: 10
aattcggtac ccgggatcc                                                19

<210> SEQ ID NO 11
<211> LENGTH: 1271
<212> TYPE: DNA
<213> ORGANISM: Salvia sclarea

<400> SEQUENCE: 11
aagaagttct tgaagaagcc actaaatttg cctttaactt cttgcaagaa atgctagtca      60
aagatcgact tcaagaaaga tgggtgatat ccgaccactt atttgatgag ataaagctgg     120
ggttgaagat gccatggtac gccactctac cccgagtcga ggctgcatat tatctagacc     180
attatgctgg ttctggtgat gtatggattg caagagtttt ctacaggatg ccagaaatca     240
gcaatgatac atacaaggag cttgcgtatt tggatttcaa cagatgccaa acacaacatc     300
agttggagtg gatccatatg caggaatggt acgacagatg cagccttagc gaattcggga     360
taagcaaaag agagttgctt cgctcttact ttctggccgc agcaaccata ttcgaaccgg     420
agagaactca agagaggctt ctgtgggcca aaaccagaat tctttctaag atgatcactt     480
catttgtcaa cattagtgga acaacactat ctttggacta caatttcaat ggcctcgatg     540
aaataattag tagtgccaat gaagatcaag actggctggg actctgctg gcaaccttcc      600 atcaacttct agacggattc gatatataca ctctccatca actcaaacat gtttggagcc     660
aatggttcat gaaagtgcag caaggagagg gaagcggcgg ggaagacgcg gtgctcctag     720
cgaacacgct caacatctgc gccggcctca cgaagacgt gttgtccaac aatgaataca      780
cggctctgtc caccctcaca aataaaatct gcaatcgcct cgcccaaatt caagacaata     840
agattctcca agttgtggat gggagcataa aggataagga gctagaacag gatatgcagg     900
cgttggtgaa gttagtgctt caagaaaatg cggcgccgt agacagaaac atcagacaca      960 cgttttttgtc ggtttccaag actttctact acgatgccta ccacgacgat gagacgaccg    1020
atcttcatat cttcaaagta ctctttcgac cggttgtatg aaaaatatttt taagctcgtc    1080 tgcagtccac gtagataatt attttaaaat aaaggataaa ttaacgagaa acgacgccat     1140
tttaaaataa tatgttaaga atggacccta aataagagcg tcgaaacatg cattgggata    1200
taatttatta attgttacac catttcggaa taaaatgatg ttatttcttt ttcatatgta    1260
aaaaaaaaaa a                                                         1271

<210> SEQ ID NO 12
<211> LENGTH: 32
<212> TYPE: DNA
<213> ORGANISM: Artificial sequence
<220> FEATURE:
<223> OTHER INFORMATION: Primer designed specifically for FN23

<400> SEQUENCE: 12
catggcatct tcaaccccag ctttatctca tc                                  32

<210> SEQ ID NO 13
<211> LENGTH: 33
<212> TYPE: DNA
<213> ORGANISM: Artificial sequence
<220> FEATURE:
<223> OTHER INFORMATION: Primer designed specifically for FN23
```

```
<400> SEQUENCE: 13
gtggtcggat atcacccatc tttcttgaag tcg                               33

<210> SEQ ID NO 14
<211> LENGTH: 30
<212> TYPE: DNA
<213> ORGANISM: Artificial sequence
<220> FEATURE:
<223> OTHER INFORMATION: Primer designed specifically for FN23

<400> SEQUENCE: 14
cattggagat gcagactcga ccgattgacc                                   30

<210> SEQ ID NO 15
<211> LENGTH: 1449
<212> TYPE: DNA
<213> ORGANISM: Salvia sclarea

<400> SEQUENCE: 15
caaaattctc ttccattttt aagataaatag taatattcta attttccctc caaaaactcg    60
tgggaaattg aaaaatagaa ataaagatg acttctgtaa atttgagcag agcaccagca   120
gcgattatcc ggcgcaggct gcagctacag ccggaatttc atgccgagtg ttcatggctg   180
aaaagcagca gcaaacacgc gcccttgacc ttgagttgcc aaatccgtcc taagcaactc   240
tcccaaatag ctgaattgag agtaacaagc ctggatgcgt cgcaagcgag tgaaaaagac   300
atttcccttg ttcaaactcc gcataaggtt gaggttaatg aaaagatcga ggagtcaatc   360
gagtacgtcc aaaatctgtt gatgacgtcg ggcgacgggc gaataagcgt gtcaccctat   420
gacacggcag tgatcgccct gatcaaggac ttgaaagggc gcgacgcccc gcagtttccg   480
tcatgtctcg agtggatcgc gcaccaccaa ctggctgatg gctcatgggg cgacgaattc   540
ttctgtattt atgatcggat tctaaataca ttggcatgtg tcgtagcctt gaaatcatgg   600
aaccttcact ctgatattat tgaaaaagga gtgacgtaca tcaaggagaa tgtgcataaa   660
cttaaaggtg caaatgttga gcacaggaca gcggggttcg aacttgtggt tcctactttt   720
atgcaaatgg ccacagattt gggcatccaa gatctgccct atgatcatcc cctcatcaag   780
gagattgctg acacaaaaca acaaagattg aaagagatac ccaaggattt ggtttaccaa   840
atgccaacga atttactgta cagtttagaa gggttaggag atttggagtg ggaaaggcta   900
ctgaaactgc agtcgggcaa tggctccttc tcacttcgc gtcgtccac cgccgccgtc    960 ttgatgcata ccaaagatga aaaatgtttg aaatacatcg aaaacgccct caagaattgc  1020
gacggaggag caccacatac ttatccagtc gatatcttct caagactttg gcaatcgat   1080 aggctacaac gcctaggaat ttctcgtttc ttccagcacg agatcaagta tttcttagat   1140
cacatcgaaa gcgtttggga ggagaccgga gttttcagtg gaagatatac gaaatttagc   1200
gatattgatg acacgtccat gggcgttagg cttctcaaaa tgcacggata cgacgtcgat   1260
ccaaatgtac taaaacattt caagcaacaa gatggtaaat tttcctgcta cattggtcaa   1320
tcggtcgagt ctgcatctcc aatgtacaat ctttataggg ctgctcaact aagatttcca  1380
ggagaagaag ttcttgaaga agccactaaa tttgccttta acttcttgca agaaatgcta  1440
gtcaaagat                                                           1449

<210> SEQ ID NO 16
<211> LENGTH: 2655
<212> TYPE: DNA
<213> ORGANISM: Salvia sclarea
```

<400> SEQUENCE: 16

```
caaaattctc ttccattttt aagataatag taatattcta attttccctc caaaaactcg      60
tgggaaattg aaaaatagaa aataaagatg acttctgtaa atttgagcag agcaccagca     120
gcgattatcc ggcgcaggct gcagctacag ccggaatttc atgccgagtg ttcatggctg     180
aaaagcagca gcaaacacgc gcccttgacc ttgagttgcc aaatccgtcc taagcaactc     240
tcccaaatag ctgaattgag agtaacaagc ctggatgcgt cgcaagcgag tgaaaaagac     300
atttcccttg ttcaaactcc gcataaggtt gaggttaatg aaaagatcga ggagtcaatc     360
gagtacgtcc aaaatctgtt gatgacgtcg ggcgacgggc gaataagcgt gtcaccctat     420
gacacggcag tgatcgccct gatcaaggac ttgaaagggc gcgacgcccc gcagtttccg     480
tcatgtctcg agtggatcgc gcaccaccaa ctggctgatg gctcatgggg cgacgaattc     540
ttctgtattt atgatcggat tctaaataca ttggcatgtg tcgtagcctt gaaatcatgg     600
aaccttcact ctgatattat tgaaaaagga gtgacgtaca tcaaggagaa tgtgcataaa     660
cttaaaggtg caaatgttga gcacaggaca gcggggttcg aacttgtggt tcctacttt     720
atgcaaatgg ccacagattt gggcatccaa gatctgccct atgatcatcc cctcatcaag     780
gagattgctg acacaaaaca acaaagattg aaagagatac caaggatttt ggtttaccaa     840
atgccaacga atttactgta cagtttagaa gggttaggag atttggagtg ggaaaggcta     900
ctgaaactgc agtcgggcaa tggctccttc ctcacttcgc cgtcgtccac cgccgccgtc     960
ttgatgcata ccaaagatga aaatgtttg aaatacatcg aaaacgccct caagaattgc    1020
gacggaggag caccacatac ttatccagtc gatatcttct caagactttg gcaatcgat    1080
aggctacaac gcctaggaat ttctcgtttc ttccagcacg agatcaagta tttcttagat    1140
cacatcgaaa gcgtttggga ggagaccgga gttttcagtg aagatatac gaaatttagc    1200
gatattgatg acacgtccat gggcgttagg cttctcaaaa tgcacggata cgacgtcgat    1260
ccaaatgtac taaaacattt caagcaacaa gatggtaaat tttcctgcta cattggtcaa    1320
tcggtcgagt ctgcatctcc aatgtacaat ctttataggg ctgctcaact aagatttcca    1380
ggagaagaag ttcttgaaga agccactaaa tttgccttta acttcttgca agaaatgcta    1440
gtcaaagatc gacttcaaga aagatgggtg atatccgacc acttatttga tgagataaag    1500
ctggggttga agatgccatg gtacgccact ctaccccgag tcgaggctgc atattatcta    1560
gaccattatg ctggttctgg tgatgtatgg attggcaaga gttctacag gatgccagaa    1620
atcagcaatg atacatacaa ggagcttgcg atattggatt caacagatg ccaaacacaa    1680
catcagttgg agtggatcca tatgcaggaa tggtacgaca gatgcagcct tagcgaattc    1740
gggataagca aaagagagtt gcttcgctct tactttctgg ccgcagcaac catattcgaa    1800
ccggagagaa ctcaagagag gcttctgtgg gccaaaacca gaattctttc taagatgatc    1860
acttcatttg tcaacattag tggaacaaca ctatctttgg actacaattt caatggcctc    1920
gatgaaataa ttagtagtgc caatgaagat caaggactgg ctgggactct gctggcaacc    1980
ttccatcaac ttctagacgg attcgatata tacactctcc atcaactcaa acatgtttgg    2040
agccaatggt tcatgaaagt gcagcaagga gagggaagcg gcggggaaga gcgcggtgctc    2100
ctagcgaaca cgctcaacat ctgcgccggc ctcaacgaag acgtgttgtc caacaatgaa    2160
tacacggctc tgtccaccct cacaaataaa atctgcaatc gcctcgccca aattcaagac    2220
aataagattc tccaagttgt ggatgggagc ataaaggata aggagctaga acaggatatg    2280
caggcgttgg tgaagttagt gcttcaagaa aatggcggcg ccgtagacag aaacatcaga    2340
```

```
cacacgttttt tgtcggtttc caagactttc tactacgatg cctaccacga cgatgagacg    2400
accgatcttc atatcttcaa agtactcttt cgaccggttg tatgaaaaat attttaagct    2460
cgtctgcagt ccacgtagat aattatttta aaataaagga taaattaacg agaaacgacg    2520 ccatttaaa ataatatgtt aagaatggac cctaaataag agcgtcgaaa catgcattgg    2580
gatataattt attaattgtt acaccatttc ggaataaaat gatgttattt cttttcata    2640 tgtaaaaaaa aaaaa                                                     2655
```

<210> SEQ ID NO 17
<211> LENGTH: 785
<212> TYPE: PRT
<213> ORGANISM: Salvia sclarea

<400> SEQUENCE: 17

```
Met Thr Ser Val Asn Leu Ser Arg Ala Pro Ala Ala Ile Ile Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Leu Thr Leu Ser Cys Gln Ile Arg Pro
        35                  40                  45

Lys Gln Leu Ser Gln Ile Ala Glu Leu Arg Val Thr Ser Leu Asp Ala
    50                  55                  60

Ser Gln Ala Ser Glu Lys Asp Ile Ser Leu Val Gln Thr Pro His Lys
65                  70                  75                  80

Val Glu Val Asn Glu Lys Ile Glu Glu Ser Ile Glu Tyr Val Gln Asn
                85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His His Gln Leu Ala Asp
    130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Asp Leu Pro
    210                 215                 220

Tyr Asp His Pro Leu Ile Lys Glu Ile Ala Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
    290                 295                 300

Glu Asn Ala Leu Lys Asn Cys Asp Gly Gly Ala Pro His Thr Tyr Pro
305                 310                 315                 320
```

-continued

```
Val Asp Ile Phe Ser Arg Leu Trp Ala Ile Asp Arg Leu Gln Arg Leu
            325                 330                 335

Gly Ile Ser Arg Phe Phe Gln His Glu Ile Lys Tyr Phe Leu Asp His
        340                 345                 350

Ile Glu Ser Val Trp Glu Thr Gly Val Phe Ser Gly Arg Tyr Thr
            355                 360                 365

Lys Phe Ser Asp Ile Asp Asp Thr Ser Met Gly Val Arg Leu Leu Lys
370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415

Ser Pro Met Tyr Asn Leu Tyr Arg Ala Ala Gln Leu Arg Phe Pro Gly
            420                 425                 430

Glu Glu Val Leu Glu Glu Ala Thr Lys Phe Ala Phe Asn Phe Leu Gln
            435                 440                 445

Glu Met Leu Val Lys Asp Arg Leu Gln Glu Arg Trp Val Ile Ser Asp
450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
            515                 520                 525

Gln Thr Gln His Gln Leu Glu Trp Ile His Met Gln Glu Trp Tyr Asp
            530                 535                 540

Arg Cys Ser Leu Ser Glu Phe Gly Ile Ser Lys Arg Glu Leu Leu Arg
545                 550                 555                 560

Ser Tyr Phe Leu Ala Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
            580                 585                 590

Ser Phe Val Asn Ile Ser Gly Thr Thr Leu Ser Leu Asp Tyr Asn Phe
            595                 600                 605

Asn Gly Leu Asp Glu Ile Ile Ser Ser Ala Asn Glu Asp Gln Gly Leu
            610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Glu Gly Ser Gly Gly Glu Asp Ala Val Leu Leu
            660                 665                 670

Ala Asn Thr Leu Asn Ile Cys Ala Gly Leu Asn Glu Asp Val Leu Ser
            675                 680                 685

Asn Asn Glu Tyr Thr Ala Leu Ser Thr Leu Thr Asn Lys Ile Cys Asn
            690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735
```

```
Leu Val Leu Gln Glu Asn Gly Gly Ala Val Asp Arg Asn Ile Arg His
              740                 745                 750

Thr Phe Leu Ser Val Ser Lys Thr Phe Tyr Tyr Asp Ala Tyr His Asp
          755                 760                 765

Asp Glu Thr Thr Asp Leu His Ile Phe Lys Val Leu Phe Arg Pro Val
    770                 775                 780

Val
785

<210> SEQ ID NO 18
<211> LENGTH: 38
<212> TYPE: DNA
<213> ORGANISM: Artificial sequence
<220> FEATURE:
<223> OTHER INFORMATION: Primer

<400> SEQUENCE: 18
tactgacata tgacttctgt aaatttgagc agagcacc                              38

<210> SEQ ID NO 19
<211> LENGTH: 36
<212> TYPE: DNA
<213> ORGANISM: Artificial sequence
<220> FEATURE:
<223> OTHER INFORMATION: Primer

<400> SEQUENCE: 19
ttggtacctc atacaaccgg tcgaaagagt actttg                                36

<210> SEQ ID NO 20
<211> LENGTH: 31
<212> TYPE: DNA
<213> ORGANISM: Artificial sequence
<220> FEATURE:
<223> OTHER INFORMATION: Primer

<400> SEQUENCE: 20
gttggagtgg atccacatgc aggaatggta c                                     31

<210> SEQ ID NO 21
<211> LENGTH: 31
<212> TYPE: DNA
<213> ORGANISM: Artificial sequence
<220> FEATURE:
<223> OTHER INFORMATION: Primer

<400> SEQUENCE: 21
gtaccattcc tgcatctgga tccactccaa c                                     31

<210> SEQ ID NO 22
<211> LENGTH: 2358
<212> TYPE: DNA
<213> ORGANISM: Salvia sclarea

<400> SEQUENCE: 22
atgacttctg taaatttgag cagagcacca gcagcgatta cccggcgcag gctgcagcta      60
cagccggaat tcatgccga gtgttcatgg ctgaaaagca gcagcaaaca cgcgcccttg      120
accttgagtt gccaaatccg tcctaagcaa ctctcccaaa tagctgaatt gagagtaaca      180
agcctggatg cgtcgcaagc gagtgaaaaa gacatttccc ttgttcaaac tccgcataag      240
gttgaggtta atgaaaagat cgaggagtca atcgagtacg tccaaaatct gttgatgacg      300
tcgggcgacg ggcgaataag cgtgtcaccc tatgacacgc agtgatcgc cctgatcaag      360
```

-continued

```
gacttgaaag ggcgcgacgc cccgcagttt ccgtcatgtc tcgagtggat cgcgcaccac      420
caactggctg atggctcatg gggcgacgaa ttcttctgta tttatgatcg gattctaaat      480
acattggcat gtgtcgtagc cttgaaatca tggaaccttc actctgatat tattgaaaaa      540
ggagtgacgt acatcaagga gaatgtgcat aaacttaaag gtgcaaatgt tgagcacagg      600 acagcgggt tcgaacttgt ggttcctact tttatgcaaa tggccacaga tttgggcatc       660
caagatctgc cctatgatca tcccctcatc aaggagattg ctgacacaaa acaacaaaga      720
ttgaaagaga tacccaagga tttggtttac caaatgccaa cgaatttact gtacagttta      780
gaagggttag agatttgga gtgggaaagg ctactgaaac tgcagtcggg caatggctcc       840
ttcctcactt cgccgtcgtc caccgccgcc gtcttgatgc ataccaaaga tgaaaaatgt      900
ttgaaataca tcgaaaacgc cctcaagaat tgcgacggag gagcaccaca tacttatcca      960
gtcgatatct tctcaagact ttgggcaatc gataggctac aacgcctagg aatttctcgt     1020
ttcttccagc acgagatcaa gtatttctta gatcacatcg aaagcgtttg ggaggagacc     1080
ggagttttca gtggaagata tacgaaattt agcgatattg atgacacgtc catgggcgtt     1140
aggcttctca aaatgcacgg atacgacgtc gatccaaatg tactaaaaca tttcaagcaa     1200
caagatggta aattttcctg ctacattggt caatcggtcg agtctgcatc tccaatgtac     1260
aatctttata gggctgctca actaagattt ccaggagaag aagttcttga agaagccact     1320
aaatttgcct ttaacttctt gcaagaaatg ctagtcaaag atcgacttca agaaagatgg     1380
gtgatatccg accacttatt tgatgagata aagctggggt tgaagatgcc atggtacgcc     1440
actctacccc gagtcgaggc tgcatattat ctagaccatt atgctggttc tggtgatgta     1500
tggattggca agagtttcta caggatgcca gaaatcagca atgatacata caggagctt     1560 gcgatattgg atttcaacag atgccaaaca caacatcagt tggagtggat ccacatgcag     1620
gaatggtacg acagatgcag ccttagcgaa ttcgggataa gcaaaagaga gttgcttcgc     1680
tcttactttc tggccgcagc aaccatattc gaaccggaga gaactcaaga gaggcttctg     1740
tgggccaaaa ccagaattct ttctaagatg atcacttcat ttgtcaacat tagtggaaca     1800
acactatctt tggactacaa tttcaatggc ctcgatgaaa taattagtag tgccaatgaa     1860
gatcaaggac tggctgggac tctgctggca accttccatc aacttctaga cggattcgat     1920
atatacactc tccatcaact caaacatgtt tggagccaat ggttcatgaa agtgcagcaa     1980
ggagagggaa gcggcgggga agacgcggtg ctcctagcga acacgctcaa catctgcgcc     2040
ggcctcaaca agacgtgtt gtccaacaat gaatacacgg ctctgtccac cctcacaaat     2100
aaaatctgca atcgcctcgc ccaaattcaa acaataaga ttctccaagt tgtggatggg      2160
agcataaagg ataaggagct agaacaggat atgcaggcgt tggtgaagtt agtgcttcaa     2220
gaaaatggcg gcgccgtaga cagaaacatc agacacacgt ttttgtcggt ttccaagact     2280
ttctactacg atgcctacca cgacgatgag acgaccgatc ttcatatctt caaagtactc     2340
tttcgaccgg ttgtatga                                                   2358
```

```
<210> SEQ ID NO 23
<211> LENGTH: 2355
<212> TYPE: DNA
<213> ORGANISM: Salvia sclarea

<400> SEQUENCE: 23
atgacttctg taaatttgag cagagcacca gcagcgatta tccggcgcag gctgcagcta       60
cagccggaat tcatgccga gtgttcatgg ctgaaaagca gcagcaaaca cgcgccttc       120
```

```
accttgagtt gccaaatccg tcctaagcaa ctctcccaaa tagctgaatt gagagtaaca    180
agcctggatg cgtcgcaagc gagtgaaaaa gacatttccc ttgttcaaac tccgcataag    240
gttgaggtta atgaaaagat cgaggagtca atcgagtacg tccaaaatct gttgatgacg    300
tcgggcgacg ggcgaataag cgtgtcaccc tatgacacgg cagtgatcgc cctgatcaag    360
gacttgaaag ggcgcgacgc cccgcagttt ccgtcatgtc tcgagtggat cgcgcaccac    420
caactggctg atggctcatg gggcgacgaa ttcttctgta tttatgatcg gattctaaat    480
acattggcat gtgtcgtagc cttgaaatca tggaaccttc aatctgatat tattgaaaaa    540
ggtgtgacgt acatcaagga gaatgtgcat aaacttaaag gtgcaaatgt tgagcacagg    600
acagcgggt tcgaacttgt ggttcctact tttatgcaaa tggccacaga tttgggcatc    660
caaggtctgc cctatgatca tcccctcatc aaggagattg ctgacacaaa acaacaaaga    720
ttgaaagaga tacccaagga tttggtttac caaatgccaa cgaatttact gtacagttta    780
gaagggttag gagatttgga gtgggaaagg ttactgaaac tgcagtcggg caatggctcc    840
ttcctcactt cgccgtcgtc caccgccgcc gtcttgatgc ataccaaaga tgaaaaatgt    900
ttgaaataca tcgaaaacgc cctcaagaat tgcgacggag gagcaccaca tacttatcca    960
gtcgatatct tctcaagact ttgggcaatc gataggctac aacgcctagg aatttctcgt   1020
ttcttccagc acgagatcaa gtatttctta gatcacatcg aaagcgtttg ggaggagacc   1080
ggagttttca gtggaagata tacgaaattt agcgatattg atgacacgtc catgggcgtt   1140
aggcttctca aaatgcacgg atacgacgtc gatccaaatg tactaaaaca tttcaagcaa   1200
caagatggta aattttcctg ctacattggt caatcggtcg agtctgcatc tccaatgtac   1260
aatctttata gggctgctca actaagattt ccaggagaag aagttcttga agaagccact   1320
aaatttgcct ttaacttctt gcaagaaatg ctagtcaaag atcgacttca agaaagatgg   1380
gtgatatccg accacttatt tgatgagata aagctgggt tgaagatgcc atggtacgcc   1440
actctacccc gagtcgaggc tgcatattat ctagaccatt atgctggttc tggtgatgta   1500
tggattggca agagtttcta caggatgcca gaaatcagca atgatacata caaggagctt   1560
gcgatattgg atttcaacag atgccaaaca caacatcagt tggagtggat ccagatgcag   1620
gaatggtacg acagatgcag ccttagcgaa ttcgggataa gcaaaagaga gttgcttcgc   1680
tcttactttc tggccgcagc aaccatattc gaaccggaga gaactcaaga gaggcttctg   1740
tgggccaaaa ccagaattct ttctaagatg atcacttcat ttgtcaacat tagtggaaca   1800
acactatctt tggactacaa tttcaatggc ctcgatgaaa taattagtgc caatgaagat   1860
caaggactgg ctgggactct gctggcaacc ttccatcaac ttctagacgg attcgatata   1920
tacactctcc atcaactcaa acatgtttgg agccaatggt tcatgaaagt gcagcaagga   1980
gagggaagcg gcggggaaga cgcggtgctc ctagcgaaca cgctcaacat ctgcgccggc   2040
ctcaacgaag acgtgttgtc caacaatgaa tacacggctc tgtccaccct cacaaataaa   2100
atctgcaatc gcctcgccca aattcaagac aataagattc tccaagttgt ggatgggagc   2160
ataaaggata aggagctaga acaggatatg caggcgttgg tgaagttagt gcttcaagaa   2220
aatggcggcg ccgtagacag aaacatcaga cacacgtttt tgtcggtttc caagactttc   2280
tactacgatg cctaccacga cgatgagacg accgatcttc atatcttcaa agtactcttt   2340
cgaccggttg tatga                                                    2355
```

<210> SEQ ID NO 24
<211> LENGTH: 785
<212> TYPE: PRT

-continued

<213> ORGANISM: Salvia sclarea

<400> SEQUENCE: 24

Met Thr Ser Val Asn Leu Ser Arg Ala Pro Ala Ile Thr Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Leu Thr Leu Ser Cys Gln Ile Arg Pro
        35                  40                  45

Lys Gln Leu Ser Gln Ile Ala Glu Leu Arg Val Thr Ser Leu Asp Ala
50                  55                  60

Ser Gln Ala Ser Glu Lys Asp Ile Ser Leu Val Gln Thr Pro His Lys
65                  70                  75                  80

Val Glu Val Asn Glu Lys Ile Glu Glu Ser Ile Glu Tyr Val Gln Asn
                85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
        115                 120                 125

Gln Phe Pro Ser Cys Leu Glu Trp Ile Ala His His Gln Leu Ala Asp
130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu His Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Asp Leu Pro
210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
            340                 345                 350

Ile Glu Ser Val Trp Glu Glu Thr Gly Val Phe Ser Gly Arg Tyr Thr
        355                 360                 365

Lys Phe Ser Asp Ile Asp Asp Thr Ser Met Gly Val Arg Leu Leu Lys
370                 375                 380

Met His Gly Tyr Asp Val Asp Pro Asn Val Leu Lys His Phe Lys Gln
385                 390                 395                 400

```
Gln Asp Gly Lys Phe Ser Cys Tyr Ile Gly Gln Ser Val Glu Ser Ala
            405                 410                 415

Ser Pro Met Tyr Asn Leu Tyr Arg Ala Ala Gln Leu Arg Phe Pro Gly
        420                 425                 430

Glu Glu Val Leu Glu Glu Ala Thr Lys Phe Ala Phe Asn Phe Leu Gln
            435                 440                 445

Glu Met Leu Val Lys Asp Arg Leu Gln Glu Arg Trp Val Ile Ser Asp
        450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
            500                 505                 510

Ser Asn Asp Thr Tyr Lys Glu Leu Ala Ile Leu Asp Phe Asn Arg Cys
        515                 520                 525

Gln Thr Gln His Gln Leu Glu Trp Ile His Met Gln Glu Trp Tyr Asp
    530                 535                 540

Arg Cys Ser Leu Ser Glu Phe Gly Ile Ser Lys Arg Glu Leu Leu Arg
545                 550                 555                 560

Ser Tyr Phe Leu Ala Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
            580                 585                 590

Ser Phe Val Asn Ile Ser Gly Thr Thr Leu Ser Leu Asp Tyr Asn Phe
        595                 600                 605

Asn Gly Leu Asp Glu Ile Ile Ser Ser Ala Asn Glu Asp Gln Gly Leu
    610                 615                 620

Ala Gly Thr Leu Leu Ala Thr Phe His Gln Leu Leu Asp Gly Phe Asp
625                 630                 635                 640

Ile Tyr Thr Leu His Gln Leu Lys His Val Trp Ser Gln Trp Phe Met
                645                 650                 655

Lys Val Gln Gln Gly Glu Gly Ser Gly Gly Glu Asp Ala Val Leu Leu
            660                 665                 670

Ala Asn Thr Leu Asn Ile Cys Ala Gly Leu Asn Glu Asp Val Leu Ser
        675                 680                 685

Asn Asn Glu Tyr Thr Ala Leu Ser Thr Leu Thr Asn Lys Ile Cys Asn
    690                 695                 700

Arg Leu Ala Gln Ile Gln Asp Asn Lys Ile Leu Gln Val Val Asp Gly
705                 710                 715                 720

Ser Ile Lys Asp Lys Glu Leu Glu Gln Asp Met Gln Ala Leu Val Lys
                725                 730                 735

Leu Val Leu Gln Glu Asn Gly Gly Ala Val Asp Arg Asn Ile Arg His
            740                 745                 750

Thr Phe Leu Ser Val Ser Lys Thr Phe Tyr Tyr Asp Ala Tyr His Asp
        755                 760                 765

Asp Glu Thr Thr Asp Leu His Ile Phe Lys Val Leu Phe Arg Pro Val
    770                 775                 780

Val
785

<210> SEQ ID NO 25
<211> LENGTH: 784
<212> TYPE: PRT
<213> ORGANISM: Salvia sclarea
```

```
<400> SEQUENCE: 25

Met Thr Ser Val Asn Leu Ser Arg Ala Pro Ala Ala Ile Ile Arg Arg
1               5                   10                  15

Arg Leu Gln Leu Gln Pro Glu Phe His Ala Glu Cys Ser Trp Leu Lys
            20                  25                  30

Ser Ser Ser Lys His Ala Pro Phe Thr Leu Ser Cys Gln Ile Arg Pro
            35                  40                  45

Lys Gln Leu Ser Gln Ile Ala Glu Leu Arg Val Thr Ser Leu Asp Ala
        50                  55                  60

Ser Gln Ala Ser Glu Lys Asp Ile Ser Leu Val Gln Thr Pro His Lys
65                  70                  75                  80

Val Glu Val Asn Glu Lys Ile Glu Glu Ser Ile Glu Tyr Val Gln Asn
                85                  90                  95

Leu Leu Met Thr Ser Gly Asp Gly Arg Ile Ser Val Ser Pro Tyr Asp
            100                 105                 110

Thr Ala Val Ile Ala Leu Ile Lys Asp Leu Lys Gly Arg Asp Ala Pro
            115                 120                 125

Gln Phe Pro Ser Cys Leu Glu Trp Ile Ala His Gln Leu Ala Asp
130                 135                 140

Gly Ser Trp Gly Asp Glu Phe Phe Cys Ile Tyr Asp Arg Ile Leu Asn
145                 150                 155                 160

Thr Leu Ala Cys Val Val Ala Leu Lys Ser Trp Asn Leu Gln Ser Asp
                165                 170                 175

Ile Ile Glu Lys Gly Val Thr Tyr Ile Lys Glu Asn Val His Lys Leu
            180                 185                 190

Lys Gly Ala Asn Val Glu His Arg Thr Ala Gly Phe Glu Leu Val Val
        195                 200                 205

Pro Thr Phe Met Gln Met Ala Thr Asp Leu Gly Ile Gln Gly Leu Pro
210                 215                 220

Tyr Asp His Pro Leu Ile Lys Glu Ile Ala Asp Thr Lys Gln Gln Arg
225                 230                 235                 240

Leu Lys Glu Ile Pro Lys Asp Leu Val Tyr Gln Met Pro Thr Asn Leu
                245                 250                 255

Leu Tyr Ser Leu Glu Gly Leu Gly Asp Leu Glu Trp Glu Arg Leu Leu
            260                 265                 270

Lys Leu Gln Ser Gly Asn Gly Ser Phe Leu Thr Ser Pro Ser Ser Thr
        275                 280                 285

Ala Ala Val Leu Met His Thr Lys Asp Glu Lys Cys Leu Lys Tyr Ile
290                 295                 300

Glu Asn Ala Leu Lys Asn Cys Asp Gly Gly Ala Pro His Thr Tyr Pro
305                 310                 315                 320

Val Asp Ile Phe Ser Arg Leu Trp Ala Ile Asp Arg Leu Gln Arg Leu
                325                 330                 335

Gly Ile Ser Arg Phe Phe Gln His Glu Ile Lys Tyr Phe Leu Asp His
            340                 345                 350

Ile Glu Ser Val Trp Glu Glu Thr Gly Val Phe Ser Gly Arg Tyr Thr
        355                 360                 365

Lys Phe Ser Asp Ile Asp Asp Thr Ser Met Gly Val Arg Leu Leu Lys
370                 375                 380

Met His Gly Tyr Asp Val Asp Pro Asn Val Leu Lys His Phe Lys Gln
385                 390                 395                 400

Gln Asp Gly Lys Phe Ser Cys Tyr Ile Gly Gln Ser Val Glu Ser Ala
                405                 410                 415
```

Ser Pro Met Tyr Asn Leu Tyr Arg Ala Ala Gln Leu Arg Phe Pro Gly
        420                 425                 430

Glu Glu Val Leu Glu Ala Thr Lys Phe Ala Phe Asn Phe Leu Gln
    435                 440                 445

Glu Met Leu Val Lys Asp Arg Leu Gln Glu Arg Trp Val Ile Ser Asp
450                 455                 460

His Leu Phe Asp Glu Ile Lys Leu Gly Leu Lys Met Pro Trp Tyr Ala
465                 470                 475                 480

Thr Leu Pro Arg Val Glu Ala Ala Tyr Tyr Leu Asp His Tyr Ala Gly
                485                 490                 495

Ser Gly Asp Val Trp Ile Gly Lys Ser Phe Tyr Arg Met Pro Glu Ile
                500                 505                 510

Ser Asn Asp Thr Tyr Lys Glu Leu Ala Ile Leu Asp Phe Asn Arg Cys
                515                 520                 525

Gln Thr Gln His Gln Leu Glu Trp Ile Gln Met Gln Glu Trp Tyr Asp
530                 535                 540

Arg Cys Ser Leu Ser Glu Phe Gly Ile Ser Lys Arg Glu Leu Leu Arg
545                 550                 555                 560

Ser Tyr Phe Leu Ala Ala Thr Ile Phe Glu Pro Glu Arg Thr Gln
                565                 570                 575

Glu Arg Leu Leu Trp Ala Lys Thr Arg Ile Leu Ser Lys Met Ile Thr
                580                 585                 590

Ser Phe Val Asn Ile Ser Gly Thr Thr Leu Ser Leu Asp Tyr Asn Phe
        595                 600                 605

Asn Gly Leu Asp Glu Ile Ile Ser Ala Asn Glu Asp Gln Gly Leu Ala
        610                 615                 620

Gly Thr Leu Leu Ala Thr Phe His Gln Leu Leu Asp Gly Phe Asp Ile
625                 630                 635                 640

Tyr Thr Leu His Gln Leu Lys His Val Trp Ser Gln Trp Phe Met Lys
                645                 650                 655

Val Gln Gln Gly Glu Gly Ser Gly Gly Glu Asp Ala Val Leu Leu Ala
                660                 665                 670

Asn Thr Leu Asn Ile Cys Ala Gly Leu Asn Glu Asp Val Leu Ser Asn
        675                 680                 685

Asn Glu Tyr Thr Ala Leu Ser Thr Leu Thr Asn Lys Ile Cys Asn Arg
        690                 695                 700

Leu Ala Gln Ile Gln Asp Asn Lys Ile Leu Gln Val Val Asp Gly Ser
705                 710                 715                 720

Ile Lys Asp Lys Glu Leu Glu Gln Asp Met Gln Ala Leu Val Lys Leu
                725                 730                 735

Val Leu Gln Glu Asn Gly Gly Ala Val Asp Arg Asn Ile Arg His Thr
                740                 745                 750

Phe Leu Ser Val Ser Lys Thr Phe Tyr Tyr Asp Ala Tyr His Asp Asp
        755                 760                 765

Glu Thr Thr Asp Leu His Ile Phe Lys Val Leu Phe Arg Pro Val Val
        770                 775                 780

<210> SEQ ID NO 26
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)

```
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 26
tatgatacng cngtnatdgc                                               20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tatgacacgg cagtgatcgc                                               20

<210> SEQ ID NO 28
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: n is a, c, g, or t

<400> SEQUENCE: 28
tatgacacgg cakkgrtngc                                               20

<210> SEQ ID NO 29
<211> LENGTH: 23
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 29
caactggctg atggntcntg ggg                                           23

<210> SEQ ID NO 30
<211> LENGTH: 23
<212> TYPE: DNA
<213> ORGANISM: Artificial sequence
<220> FEATURE:
<223> OTHER INFORMATION: Primer

<400> SEQUENCE: 30
caactggctg atggctcatg ggg                                           23

<210> SEQ ID NO 31
<211> LENGTH: 26
<212> TYPE: DNA
<213> ORGANISM: Artificial sequence
<220> FEATURE:
```

<223> OTHER INFORMATION: Primer

<400> SEQUENCE: 31
gatcctccaa crtcrwarar rtcrtc         26

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
gatcctccac gtcgwagaag tcgtc          25

<210> SEQ ID NO 33
<211> LENGTH: 81
<212> TYPE: DNA
<213> ORGANISM: Salvia sclarea

<400> SEQUENCE: 33
ctgatgtttc tgtctacggc gccgccattt tcttgaagca ctaacttcac caacgcctgc    60
atatcctgtt ctagctcctt a                                              81

<210> SEQ ID NO 34
<211> LENGTH: 73
<212> TYPE: DNA
<213> ORGANISM: Salvia sclarea

<400> SEQUENCE: 34
attcctgcat atggatccac tccaactgat gttgtgtttg gcatctgttg aaatccaata    60
tcgcaagctc ctt                                                       73

<210> SEQ ID NO 35
<211> LENGTH: 52
<212> TYPE: DNA
<213> ORGANISM: Salvia sclarea

<400> SEQUENCE: 35
tattattgaa aaaggagtga cgtacatcaa ggagaatgtg cataaactta aa            52

<210> SEQ ID NO 36
<211> LENGTH: 857
<212> TYPE: DNA
<213> ORGANISM: Salvia sclarea

<400> SEQUENCE: 36
atgtcaccac aaacagagac taaagcaagt gttggattca agcgggtgt taaagagtac     60 aaattgactt attatactcc tgaatacgaa accaaagata ctgatatctt ggcagcattc   120
cgagtaactc ctcaacccgg agttccgcct gaagaagcag gggccgcggt agctgccgaa   180
tcttctactg gtacatggac aactgtgtgg accgatggac ttaccagcct tgatcgttac   240
aaagggcgat gctaccacat tgagcccgtt cctggagaaa aagatcaata tatctgttat   300
gtagcttacc ctttagacct ttttgaagaa ggttctgtta ctaacatgtt tacttccatt   360
gtaggaaatg tatttggatt caaagcccta cgtgctctac gtctggaaga tctgcgaatt   420
cctgttgctt atgttaaaac tttccaaggc ccgcctcatg ggatccaagt tgagagagat   480
aaattgaaca agtacggtcg tcctctgctg ggatgtacta ttaaacctaa attggggtta   540
tctgctaaaa actatggtag agcggtttat gaatgtcttc gcggtggact tgattttacc   600

```
aaagatgatg agaacgtgaa ctcccagcca tttatgcgtt ggagagaccg cttcttattt    660
tgtgccgaag caatttataa agcacaggct gaaacaggtg aaatcaaagg cattacttg     720 aatgctactg cgggtacatg cgaagagatg atgaaaagag ctatatttgc tagagaattg    780
ggagttccta tcgtaatgca cgactactta acaggaggat tcaccgcaaa taccagtttg    840
gctcattatt gccgaga                                                   857
```

<210> SEQ ID NO 37
<211> LENGTH: 540
<212> TYPE: DNA
<213> ORGANISM: Salvia sclarea

<400> SEQUENCE: 37

```
aaagtatcca ctgctttaaa ttcaaacttg atttctttcc atacctcaca agcggcagct     60
agttcaggac tccatttgca agcttcacgg ataattgcat taccttcagc agcaagatca    120
cgtccttcat tacgagcttt tacacacgct tctacagcta ctcggttagc tacagcacct    180
ggtgcattac cccaagggtg tcctaaagtt cctccaccga actgtagtac ggaatcgtct    240
ccaaagatct cggtcagagc aggcatatgc caaacgtgaa taccccctga agccacagga    300
ataacacccg gcagggagac ccaatcttga gtgaaataaa taccgcgact tcggtctttt    360
tcaataaaat catcacgcag taaatcaaca aaacctaaag taatgtctct ctctccttca    420
agtttaccta ctacggtacc agagtgaata tgatctccac cggacagacg taacgcttta    480
gctagtacac ggaagtgcat accgtgattc ttctgtctat caataactgc atgcattgca    540
```

<210> SEQ ID NO 38
<211> LENGTH: 60
<212> TYPE: DNA
<213> ORGANISM: Salvia sclarea

<400> SEQUENCE: 38

```
atgttcgtct cgcatttgcc aaaacatctg tgcttgtaac aattatggat gattttttcg     60
```

<210> SEQ ID NO 39
<211> LENGTH: 35
<212> TYPE: DNA
<213> ORGANISM: Salvia sclarea

<400> SEQUENCE: 39

```
cttctacctt ggcctgcatt cttgctctta aaaaa                                35
```

<210> SEQ ID NO 40
<211> LENGTH: 35
<212> TYPE: DNA
<213> ORGANISM: Salvia sclarea

<400> SEQUENCE: 40

```
aaaaaaaata tgatctaaaa aatggatcag tttaa                                35
```

<210> SEQ ID NO 41
<211> LENGTH: 72
<212> TYPE: DNA
<213> ORGANISM: Salvia sclarea

<400> SEQUENCE: 41

```
actactcatg caatggcatt taggcttttg cgagtgaaag gatacgaagt ttcatcagag     60
gagttggcct ca                                                         72
```

<210> SEQ ID NO 42

```
<211> LENGTH: 35
<212> TYPE: DNA
<213> ORGANISM: Salvia sclarea

<400> SEQUENCE: 42
gcaactgatg attttgtgga tgttgggggc agctc                              35

<210> SEQ ID NO 43
<211> LENGTH: 35
<212> TYPE: DNA
<213> ORGANISM: Salvia sclarea

<400> SEQUENCE: 43
gccaaaataa ttccttgcat ggctttggaa ggaga                              35

<210> SEQ ID NO 44
<211> LENGTH: 11
<212> TYPE: PRT
<213> ORGANISM: Salvia sclarea

<400> SEQUENCE: 44

Ser Thr Leu Ala Cys Ile Leu Ala Leu Lys Lys
1               5                   10

<210> SEQ ID NO 45
<211> LENGTH: 10
<212> TYPE: PRT
<213> ORGANISM: Salvia sclarea

<400> SEQUENCE: 45

Lys Lys Tyr Asp Leu Lys Asn Gly Ser Val
1               5                   10

<210> SEQ ID NO 46
<211> LENGTH: 24
<212> TYPE: PRT
<213> ORGANISM: Salvia sclarea

<400> SEQUENCE: 46

Thr Thr His Ala Met Ala Phe Arg Leu Leu Arg Val Lys Gly Tyr Glu
1               5                   10                  15

Val Ser Ser Glu Glu Leu Ala Ser
            20

<210> SEQ ID NO 47
<211> LENGTH: 11
<212> TYPE: PRT
<213> ORGANISM: Salvia sclarea

<400> SEQUENCE: 47

Ala Thr Asp Asp Phe Val Asp Val Gly Gly Ser
1               5                   10

<210> SEQ ID NO 48
<211> LENGTH: 11
<212> TYPE: PRT
<213> ORGANISM: Salvia sclarea

<400> SEQUENCE: 48

Leu Leu Pro Lys Pro Cys Lys Glu Leu Phe Trp
1               5                   10

<210> SEQ ID NO 49
<211> LENGTH: 27
<212> TYPE: DNA
```

<210> SEQ ID NO 49
<211> LENGTH: 27
<212> TYPE: DNA
<213> ORGANISM: Artificial sequence
<220> FEATURE:
<223> OTHER INFORMATION: Primer

<400> SEQUENCE: 49
cttctacctt ggcctgcatt cttgctc                                27

<210> SEQ ID NO 50
<211> LENGTH: 27
<212> TYPE: DNA
<213> ORGANISM: Artificial sequence
<220> FEATURE:
<223> OTHER INFORMATION: Primer

<400> SEQUENCE: 50
gagcaagaat gcaggccaag gtagaag                                27

<210> SEQ ID NO 51
<211> LENGTH: 31
<212> TYPE: DNA
<213> ORGANISM: Artificial sequence
<220> FEATURE:
<223> OTHER INFORMATION: Primer

<400> SEQUENCE: 51
ctactcatgc aatggcattt aggcttttgc g                           31

<210> SEQ ID NO 52
<211> LENGTH: 33
<212> TYPE: DNA
<213> ORGANISM: Salvia sclarea

<400> SEQUENCE: 52
gtgaaaggat acgaagtttc atcagaggag ttg                         33

<210> SEQ ID NO 53
<211> LENGTH: 32
<212> TYPE: DNA
<213> ORGANISM: Artificial sequence
<220> FEATURE:
<223> OTHER INFORMATION: Primer

<400> SEQUENCE: 53
gaggccaact cctctgatga aacttcgtat cc                          32

<210> SEQ ID NO 54
<211> LENGTH: 30
<212> TYPE: DNA
<213> ORGANISM: Artificial sequence
<220> FEATURE:
<223> OTHER INFORMATION: Primer

<400> SEQUENCE: 54
cactcgcaaa agcctaaatg ccattgcatg                             30

<210> SEQ ID NO 55
<211> LENGTH: 29
<212> TYPE: DNA
<213> ORGANISM: Artificial sequence
<220> FEATURE:
<223> OTHER INFORMATION: Primer

<400> SEQUENCE: 55
ctgatgattt tgtggatgtt gggggcagc                              29

<210> SEQ ID NO 56

```
<211> LENGTH: 29
<212> TYPE: DNA
<213> ORGANISM: Artificial sequence
<220> FEATURE:
<223> OTHER INFORMATION: Primer

<400> SEQUENCE: 56
gctgccccca acatccacaa aatcatcag                                    29

<210> SEQ ID NO 57
<211> LENGTH: 33
<212> TYPE: DNA
<213> ORGANISM: Artificial sequence
<220> FEATURE:
<223> OTHER INFORMATION: Primer

<400> SEQUENCE: 57
ctccttccaa agccatgcaa ggaattattt tgg                               33

<210> SEQ ID NO 58
<211> LENGTH: 33
<212> TYPE: DNA
<213> ORGANISM: Artificial sequence
<220> FEATURE:
<223> OTHER INFORMATION: Primer

<400> SEQUENCE: 58
ccaaaataat tccttgcatg gctttggaag gag                               33

<210> SEQ ID NO 59
<211> LENGTH: 24
<212> TYPE: DNA
<213> ORGANISM: Artificial sequence
<220> FEATURE:
<223> OTHER INFORMATION: Primer

<400> SEQUENCE: 59
gcgtatctga ttcctgccct ttgc                                         24

<210> SEQ ID NO 60
<211> LENGTH: 28
<212> TYPE: DNA
<213> ORGANISM: Artificial sequence
<220> FEATURE:
<223> OTHER INFORMATION: Primer

<400> SEQUENCE: 60
gtttaattcc atagggggatt tcttcaag                                    28

<210> SEQ ID NO 61
<211> LENGTH: 24
<212> TYPE: DNA
<213> ORGANISM: Artificial sequence
<220> FEATURE:
<223> OTHER INFORMATION: Primer

<400> SEQUENCE: 61
atgtcgcttc ctctctccac ttgc                                         24

<210> SEQ ID NO 62
<211> LENGTH: 32
<212> TYPE: DNA
<213> ORGANISM: Artificial sequence
<220> FEATURE:
<223> OTHER INFORMATION: Primer

<400> SEQUENCE: 62
```
cgaatgggtt tctcttttat atatagatac ag                                   32

<210> SEQ ID NO 63
<211> LENGTH: 28
<212> TYPE: DNA
<213> ORGANISM: Artificial sequence
<220> FEATURE:
<223> OTHER INFORMATION: Primer

<400> SEQUENCE: 63
ttatatcctt gctcctgttt gttccttg                                        28

<210> SEQ ID NO 64
<211> LENGTH: 32
<212> TYPE: DNA
<213> ORGANISM: Artificial sequence
<220> FEATURE:
<223> OTHER INFORMATION: Primer

<400> SEQUENCE: 64
tcaaaagaca aaggatttca tatcttcctt gg                                   32

<210> SEQ ID NO 65
<211> LENGTH: 26
<212> TYPE: DNA
<213> ORGANISM: Artificial sequence
<220> FEATURE:
<223> OTHER INFORMATION: Primer

<400> SEQUENCE: 65
caccctaata tcacccgtac caaacg                                          26

<210> SEQ ID NO 66
<211> LENGTH: 36
<212> TYPE: DNA
<213> ORGANISM: Artificial sequence
<220> FEATURE:
<223> OTHER INFORMATION: Primer

<400> SEQUENCE: 66
cctatagtgt caaaagacaa aggatttcat atcttc                               36

<210> SEQ ID NO 67
<211> LENGTH: 31
<212> TYPE: DNA
<213> ORGANISM: Artificial sequence
<220> FEATURE:
<223> OTHER INFORMATION: Primer

<400> SEQUENCE: 67
gcttattgag aaagatggta gtccaagcaa g                                    31

<210> SEQ ID NO 68
<211> LENGTH: 32
<212> TYPE: DNA
<213> ORGANISM: Artificial sequence
<220> FEATURE:
<223> OTHER INFORMATION: Primer

<400> SEQUENCE: 68
gctctataaa gctcaataat catcggcagg tc                                   32

<210> SEQ ID NO 69
<211> LENGTH: 39
<212> TYPE: DNA
<213> ORGANISM: Artificial sequence
<220> FEATURE:

```
<223> OTHER INFORMATION: Primer

<400> SEQUENCE: 69
ccacaacctg aatgtgttat ctagaatagt gttgatttc                              39

<210> SEQ ID NO 70
<211> LENGTH: 32
<212> TYPE: DNA
<213> ORGANISM: Artificial sequence
<220> FEATURE:
<223> OTHER INFORMATION: Primer

<400> SEQUENCE: 70
ggaagaattg atcgaccccc aacctttgaa gg                                     32

<210> SEQ ID NO 71
<211> LENGTH: 34
<212> TYPE: DNA
<213> ORGANISM: Artificial sequence
<220> FEATURE:
<223> OTHER INFORMATION: Primer

<400> SEQUENCE: 71
ggcaatgtta ctactcatgc aatggcattt aggc                                   34

<210> SEQ ID NO 72
<211> LENGTH: 34
<212> TYPE: DNA
<213> ORGANISM: Artificial sequence
<220> FEATURE:
<223> OTHER INFORMATION: Primer

<400> SEQUENCE: 72
gcctaaatgc cattgcatga gtagtaacat tgcc                                   34

<210> SEQ ID NO 73
<211> LENGTH: 28
<212> TYPE: DNA
<213> ORGANISM: Artificial sequence
<220> FEATURE:
<223> OTHER INFORMATION: Primer

<400> SEQUENCE: 73
ggtggtcaca ggaaatcctt ggactgga                                          28

<210> SEQ ID NO 74
<211> LENGTH: 25
<212> TYPE: DNA
<213> ORGANISM: Artificial sequence
<220> FEATURE:
<223> OTHER INFORMATION: Primer

<400> SEQUENCE: 74
cctgctccca actctttggc cggag                                             25

<210> SEQ ID NO 75
<211> LENGTH: 28
<212> TYPE: DNA
<213> ORGANISM: Artificial sequence
<220> FEATURE:
<223> OTHER INFORMATION: Primer

<400> SEQUENCE: 75
cgtaactccg acgttgaagg cgagcgac                                          28

<210> SEQ ID NO 76
```

```
<211> LENGTH: 23
<212> TYPE: DNA
<213> ORGANISM: Artificial sequence
<220> FEATURE:
<223> OTHER INFORMATION: Primer

<400> SEQUENCE: 76
caccatgtcg ctcgccttca acg                                            23

<210> SEQ ID NO 77
<211> LENGTH: 33
<212> TYPE: DNA
<213> ORGANISM: Artificial sequence
<220> FEATURE:
<223> OTHER INFORMATION: Primer

<400> SEQUENCE: 77
caccatggcg aaaatgaaag agaatttcaa gag                                 33

<210> SEQ ID NO 78
<211> LENGTH: 24
<212> TYPE: DNA
<213> ORGANISM: Artificial sequence
<220> FEATURE:
<223> OTHER INFORMATION: Primer

<400> SEQUENCE: 78
caccatgtcg cttcctctct ccac                                           24

<210> SEQ ID NO 79
<211> LENGTH: 27
<212> TYPE: DNA
<213> ORGANISM: Artificial sequence
<220> FEATURE:
<223> OTHER INFORMATION: Primer

<400> SEQUENCE: 79
caccatggaa actgggcttc aaactgc                                        27

<210> SEQ ID NO 80
<211> LENGTH: 30
<212> TYPE: DNA
<213> ORGANISM: Artificial sequence
<220> FEATURE:
<223> OTHER INFORMATION: Primer

<400> SEQUENCE: 80
ttatatcctt gctcctgttt gttccttgag                                     30

<210> SEQ ID NO 81
<211> LENGTH: 547
<212> TYPE: DNA
<213> ORGANISM: Salvia sclarea

<400> SEQUENCE: 81
agcggccgct gaattctaga atttggatgt ggaatagaat tgacgaatgg cgtgcaagcg    60
cgcctctctc ctctctcctc tctctagaaa atatgattgt gcagttgagt tggcaaaagc   120
gtatctgatt cctgcccttt gctaactttc ccaaattttg tcccgtttaa ttccataggg   180
gatttcttca aggccgccat gtcgcttcct ctctccactt gcaatggatc acatttcgg    240 agataccgct tgtctcctgc ttcagcagct tctatggaaa ctgggcttca aactgctact   300
tcagcaaaaa tcgcctctat gccagcgtgc tttgaggaga cgagagggag gatagcaaag   360
ttgtttcata aggatgaact ttctgtgtcg acatatgata cagcatgggt tgccatggtc   420
```

```
ccttctccaa cttcgttaga ggaaccttgc ttccccgatt gtctaaactg gttgctcgag    480
aaccagtgcc atgatggttc gtgggcccgt ccccaccatc actctttgct aatgaaagat    540
gtccttt                                                              547
```

<210> SEQ ID NO 82
<211> LENGTH: 1473
<212> TYPE: DNA
<213> ORGANISM: Salvia sclarea

<400> SEQUENCE: 82

```
ctccatatgg taaccaagag gctgttagcc agcaaacaaa tgacctgccg atgattattg     60
agctttatag agcagcaaat gagagaatat atgaagaaga gaggagtctt gaaaaaattc    120
ttgcttggac taccatcttt ctcaataagc aagtgcaaga taactcaatt cccgacaaaa    180
aactgcacaa actggtggaa ttctacttga ggaattacaa aggcataacc ataagattgg    240
gagctagacg aaacctcgag ctatatgaca tgacctacta tcaagctctg aaatctacaa    300
acaggttctc taatttatgc aacgaagatt ttctagtttt cgcaaagcaa gatttcgata    360
tacatgaagc ccagaaccag aaaggacttc aacaactgca aggtggtat gcagattgta    420 ggttggacac cttaaacttt ggaagagatg tagttattat tgctaattat ttggcttcat    480
taattattgg tgatcatgcg tttgactatg ttcgtctcgc atttgccaaa acatctgtgc    540
ttgtaacaat tatggatgat ttttcgact gtcatggctc tagtcaagag tgtgacaaga    600
tcattgaatt agtaaaagaa tggaaggaga atccggatgc agagtacgga tctgaggagc    660
ttgagatcct ttttatggcg ttgtacaata cagtaaatga gttggcggag agggctcgtg    720
ttgaacaggg gcgtagtgtc aaagagtttc tagtcaaact gtgggttgaa atactctcag    780 cttcaagat agaattagat acatggagca atggcacgca gcaaagcttc gatgaataca    840
tttcttcgtc gtggttgtcg aacggttccc ggctgacagg tctcctgacg atgcaattcg    900
tcggagtaaa attgtccgat gaaatgctta tgagtgaaga gtgcactgat ttggctaggc    960
atgtctgtat ggtcggccgg ctgctcaacg acgtgtgcag ttctgagagg gagcgcgagg   1020
aaaatattgc aggaaaaagt tatagcattc tactagcaac tgaaaagat ggaagaaaag    1080 ttagtgaaga tgaagccatt gcagagatca tgaaatggt tgaatatcac tggagaaaag    1140
tgttgcagat tgtgtataaa aagaaagca ttttgccaag aagatgcaaa gatgtatttt    1200
tggagatggc taagggtacg ttttatgctt atgggatcaa cgatgaattg acttctcctc    1260
agcaatccaa ggaagatatg aaatcctttg tcttttgaca ctataggctc gtttggtacg    1320
ggtgatatta gggtgtgtaa tacaattatg acactgtaat attttatttt gtacaaaaca    1380
cgtggttctt tgcatatcaa aaatttgaaa atgttataag gatttgtatc cactataaga    1440
aattgttgga taaaaaaaaa aaaaaaaaaa aaa                                 1473
```

<210> SEQ ID NO 83
<211> LENGTH: 207
<212> TYPE: DNA
<213> ORGANISM: Salvia sclarea

<400> SEQUENCE: 83

```
cacatgtgct ccgtggtcca tctattctac agtaaagacg acggattcac ctcgcaggat     60
ttgattcaag ttgtaaatgc aattattcac aaacctattg tcctcaagga acaaacagga    120
gcaaggatat aattttttta atctgtatct atatataaaa gagaaaccca ttcgttaaaa    180
taaaaaaaaa aaaaaaaaa aaaaaaa                                         207
```

<210> SEQ ID NO 84
<211> LENGTH: 464
<212> TYPE: DNA
<213> ORGANISM: Salvia sclarea

<400> SEQUENCE: 84

| | | | | | |
|---|---|---|---|---|---|
| aaattaatta | ggaataaaaa | aaattggact | ttatatttat | tagaaacggc | cgccgccgca | 60 |
| aaaaaatgtc | gctcgccttc | aacgtcggag | ttacgccttt | ctccggccaa | agagttggga | 120 |
| gcaggaaaga | aaaatttcca | gtccaaggat | ttcctgtgac | cacccccaat | aggtcacgtc | 180 |
| tcatcgttaa | ctgcagcctt | actacaatag | atttcatggc | gaaaatgaaa | gagaatttca | 240 |
| agagggaaga | cgataaattt | ccaacgacaa | cgactcttcg | atccgaagat | atacccctcta | 300 |
| atttgtgtat | aatcgacacc | cttcaaaggt | tgggggtcga | tcaattcttc | caatatgaaa | 360 |
| tcaacactat | tctagataac | acattcaggt | tgtggcaaga | aaaacacaaa | gttatatatg | 420 |
| gcaatgttac | tactcatgca | atggcattta | ggcttttgcg | agtg | | 464 |

<210> SEQ ID NO 85
<211> LENGTH: 2388
<212> TYPE: DNA
<213> ORGANISM: Salvia sclarea

<400> SEQUENCE: 85

| | | | | | |
|---|---|---|---|---|---|
| atgtcgcttc | ctctctccac | ttgcaatgga | tcacattttc | ggagataccg | cttgtctcct | 60 |
| gcttcagctt | ctatggaaac | tgggcttcaa | actgctactt | cagcaaaaat | cgcctctatg | 120 |
| ccagcgtgct | ttgaggagac | gagagggagg | atagcaaagt | tgtttcataa | ggatgaactt | 180 |
| tctgtgtcga | catatgatac | agcatgggtt | gccatggtcc | cttctccaac | ttcgttagag | 240 |
| gaaccttgct | tccccgattg | tctaaactgg | ttgctcgaga | accagtgcca | tgatggttcg | 300 |
| tgggcccgtc | cccaccatca | ctcttttgcta | atgaaagatg | tcctttcttc | taccttggcc | 360 |
| tgcattcttg | ctcttaaaaa | atggggagtt | ggtgaaaaac | agattaacag | gggcttgcat | 420 |
| tttatggagt | tgaattttgc | ttcagctact | gagaagtgtc | agattactcc | catgggattt | 480 |
| gatattgtat | ttcctgccat | gcttgattat | gccagagact | tctctttgga | catgcattta | 540 |
| gagccaacta | cgttgaatga | tttgatacat | aagagggatt | tggagcttaa | aagcaagcca | 600 |
| gattttttcat | cggatgggga | agcctattgg | gcatatatag | ctgaaggaat | ggggaattta | 660 |
| cggaactggg | aatcagttat | gaaatatcaa | agaaggaatg | gatctctttt | caactgtcct | 720 |
| tccacgacag | cagctgcttt | tgttgcactg | ggcaattctg | actgcctcaa | ctacctgcat | 780 |
| tcagccttaa | agaagtttgg | gaatgcagtt | cctgcagttt | atcctctaga | tatatattct | 840 |
| cacctgtgca | tagttgacaa | tcttgaaagg | ttggggatca | gccgttattt | tttgactgag | 900 |
| attcaaagcg | tgttagatga | aacacacaga | tgttggatgc | agggcaatga | agagatcttc | 960 |
| atggatgcct | caacttgtgc | tttagctttc | cggatattgc | gattgaacgg | atacgatgta | 1020 |
| acttcagatc | cggttacaaa | aattcaacac | gagtgctttt | cgagttcctt | tcatggaaat | 1080 |
| gtgatggaca | ttaacacgac | tcttgaatta | tatagggcat | ctgaactcat | actatatcca | 1140 |
| gatgaaagag | atctagtgag | acaaaattta | aggcttaaac | aaatactaga | gcaagagcta | 1200 |
| tccaatggtt | ttattcaatc | atgtcaactt | ggaagaagtg | ttaatgcaga | ggtgaaccag | 1260 |
| gctatcgagt | atccatttta | tgcaattatg | gacaggggttg | caaaacggaa | aaatatagag | 1320 |
| aactacaact | tgataatac | aagaattctg | aaaacttcat | attgttcacc | aaattttggc | 1380 |
| aacaaggatt | ttcttttttct | gtccgtagag | gacttcaatc | tgtgtcaagc | cacacatcgc | 1440 |

-continued

```
gaagaactca gggaacttga aagatgggtc gtagagaata gattggacga gctgcagttt    1500
gcaaggagta agtctgcata ttgttatttt tctgcagcag caaccttttc tgctccagaa    1560
ctacgtgatg cacgcatgtc gtgggccaaa ggtggtgttc tgactacagt gattgatgac    1620 tttttgacg tcggaggttc tatggaagaa ttgaagaact taattcattt ggttgaaaaa     1680
tgggatgtgg atgttagcac agaatgctct cccataatg tccagataat attttcagca    1740
cttaagagca caatccgtga aattggatac aaagggttga agctacaagg gcgttgtatt    1800
actaaccata taattggcat ttggttagat ttgctgaatt ctatgatgaa agaaactgaa    1860
tgggctagag acaactatgt cccaacaatt gatgaatata tgagcaatgc atatgtgtca    1920
tttgctctgg ggccaattgt tctgccaact ctatatcttg ttgggccgaa gctctcagaa    1980
gagatggcaa accaccccga gtactataaa ctattcaaat tgatgagcac atgcggacgc    2040
cttttaaatg acatccgtgg ttatgagaga gaactcaaag atggtaaact gaacgcgcta    2100
tctttgtaca tggctaatca tggtggtgaa gtaagtaaag aagcagccat ttcagagatc    2160
aaaagttgga ttgagagcag taggagagaa ttactgagat tagttttgga ggggaagaag    2220
agtgtccttc caaagccatg caaggaatta ttttggcaca tgtgctctgt ggtccatcta    2280
ttctacagta agacgacgg attcacctcg caggatttga ttcaagttgt aaatgcaatt    2340
attcacaaac ctattgtcct caaggaacaa acaggagcaa ggatataa                 2388
```

```
<210> SEQ ID NO 86
<211> LENGTH: 795
<212> TYPE: PRT
<213> ORGANISM: Salvia sclarea

<400> SEQUENCE: 86

Met Ser Leu Pro Leu Ser Thr Cys Asn Gly Ser His Phe Arg Arg Tyr
1               5                   10                  15

Arg Leu Ser Pro Ala Ser Ala Ser Met Glu Thr Gly Leu Gln Thr Ala
                20                  25                  30

Thr Ser Ala Lys Ile Ala Ser Met Pro Ala Cys Phe Glu Glu Thr Arg
            35                  40                  45

Gly Arg Ile Ala Lys Leu Phe His Lys Asp Glu Leu Ser Val Ser Thr
        50                  55                  60

Tyr Asp Thr Ala Trp Val Ala Met Val Pro Ser Pro Thr Ser Leu Glu
65                  70                  75                  80

Glu Pro Cys Phe Pro Asp Cys Leu Asn Trp Leu Leu Glu Asn Gln Cys
                85                  90                  95

His Asp Gly Ser Trp Ala Arg Pro His His His Ser Leu Leu Met Lys
                100                 105                 110

Asp Val Leu Ser Ser Thr Leu Ala Cys Ile Leu Ala Leu Lys Lys Trp
            115                 120                 125

Gly Val Gly Glu Lys Gln Ile Asn Arg Gly Leu His Phe Met Glu Leu
        130                 135                 140

Asn Phe Ala Ser Ala Thr Glu Lys Cys Gln Ile Thr Pro Met Gly Phe
145                 150                 155                 160

Asp Ile Val Phe Pro Ala Met Leu Asp Tyr Ala Arg Asp Phe Ser Leu
                165                 170                 175

Asp Met His Leu Glu Pro Thr Thr Leu Asn Asp Leu Ile His Lys Arg
                180                 185                 190

Asp Leu Glu Leu Lys Ser Lys Pro Asp Phe Ser Ser Asp Gly Glu Ala
            195                 200                 205
```

-continued

```
Tyr Trp Ala Tyr Ile Ala Glu Gly Met Gly Asn Leu Arg Asn Trp Glu
210                 215                 220

Ser Val Met Lys Tyr Gln Arg Arg Asn Gly Ser Leu Phe Asn Cys Pro
225                 230                 235                 240

Ser Thr Thr Ala Ala Phe Val Ala Leu Gly Asn Ser Asp Cys Leu
                245                 250                 255

Asn Tyr Leu His Ser Ala Leu Lys Lys Phe Gly Asn Ala Val Pro Ala
                260                 265                 270

Val Tyr Pro Leu Asp Ile Tyr Ser His Leu Cys Ile Val Asp Asn Leu
        275                 280                 285

Glu Arg Leu Gly Ile Ser Arg Tyr Phe Leu Thr Glu Ile Gln Ser Val
        290                 295                 300

Leu Asp Glu Thr His Arg Cys Trp Met Gln Gly Asn Glu Glu Ile Phe
305                 310                 315                 320

Met Asp Ala Ser Thr Cys Ala Leu Ala Phe Arg Ile Leu Arg Leu Asn
                325                 330                 335

Gly Tyr Asp Val Thr Ser Asp Pro Val Thr Lys Ile Gln His Glu Cys
                340                 345                 350

Phe Ser Ser Ser Phe His Gly Asn Val Met Asp Ile Asn Thr Thr Leu
        355                 360                 365

Glu Leu Tyr Arg Ala Ser Glu Leu Ile Leu Tyr Pro Asp Glu Arg Asp
        370                 375                 380

Leu Val Arg Gln Asn Leu Arg Leu Lys Gln Ile Leu Glu Gln Glu Leu
385                 390                 395                 400

Ser Asn Gly Phe Ile Gln Ser Cys Gln Leu Gly Arg Ser Val Asn Ala
                405                 410                 415

Glu Val Asn Gln Ala Ile Glu Tyr Pro Phe Tyr Ala Ile Met Asp Arg
                420                 425                 430

Val Ala Lys Arg Lys Asn Ile Glu Asn Tyr Asn Phe Asp Asn Thr Arg
        435                 440                 445

Ile Leu Lys Thr Ser Tyr Cys Ser Pro Asn Phe Gly Asn Lys Asp Phe
        450                 455                 460

Leu Phe Leu Ser Val Glu Asp Phe Asn Leu Cys Gln Ala Thr His Arg
465                 470                 475                 480

Glu Glu Leu Arg Glu Leu Glu Arg Trp Val Val Glu Asn Arg Leu Asp
                485                 490                 495

Glu Leu Gln Phe Ala Arg Ser Lys Ser Ala Tyr Cys Tyr Phe Ser Ala
                500                 505                 510

Ala Ala Thr Phe Ser Ala Pro Glu Leu Arg Asp Ala Arg Met Ser Trp
        515                 520                 525

Ala Lys Gly Gly Val Leu Thr Thr Val Ile Asp Asp Phe Phe Asp Val
        530                 535                 540

Gly Gly Ser Met Glu Glu Leu Lys Asn Leu Ile His Leu Val Glu Lys
545                 550                 555                 560

Trp Asp Val Asp Val Ser Thr Glu Cys Ser Ser His Asn Val Gln Ile
                565                 570                 575

Ile Phe Ser Ala Leu Lys Ser Thr Ile Arg Glu Ile Gly Tyr Lys Gly
                580                 585                 590

Leu Lys Leu Gln Gly Arg Cys Ile Thr Asn His Ile Ile Gly Ile Trp
        595                 600                 605

Leu Asp Leu Leu Asn Ser Met Met Lys Glu Thr Glu Trp Ala Arg Asp
        610                 615                 620

Asn Tyr Val Pro Thr Ile Asp Glu Tyr Met Ser Asn Ala Tyr Val Ser
625                 630                 635                 640
```

Phe Ala Leu Gly Pro Ile Val Leu Pro Thr Leu Tyr Leu Val Gly Pro
            645                 650                 655

Lys Leu Ser Glu Glu Met Ala Asn His Pro Glu Tyr Tyr Lys Leu Phe
        660                 665                 670

Lys Leu Met Ser Thr Cys Gly Arg Leu Leu Asn Asp Ile Arg Gly Tyr
            675                 680                 685

Glu Arg Glu Leu Lys Asp Gly Lys Leu Asn Ala Leu Ser Leu Tyr Met
        690                 695                 700

Ala Asn His Gly Gly Glu Val Ser Lys Glu Ala Ile Ser Glu Ile
705                 710                 715                 720

Lys Ser Trp Ile Glu Ser Ser Arg Arg Glu Leu Leu Arg Leu Val Leu
            725                 730                 735

Glu Gly Lys Lys Ser Val Leu Pro Lys Pro Cys Lys Glu Leu Phe Trp
        740                 745                 750

His Met Cys Ser Val Val His Leu Phe Tyr Ser Lys Asp Asp Gly Phe
            755                 760                 765

Thr Ser Gln Asp Leu Ile Gln Val Val Asn Ala Ile Ile His Lys Pro
        770                 775                 780

Ile Val Leu Lys Glu Gln Thr Gly Ala Arg Ile
785                 790                 795

<210> SEQ ID NO 87
<211> LENGTH: 536
<212> TYPE: DNA
<213> ORGANISM: Salvia sclarea

<400> SEQUENCE: 87
aaattaatta ggaataaaaa aaattggact ttatatttat tagaaacggc cgccgccgca      60
aaaaaatgtc gctcgccttc aacgtcggag ttacgccttt ctccggccaa agagttggga     120
gcaggaaaga aaaatttcca gtccaaggat ttcctgtgac cacccccaat aggtcacgtc     180
tcatcgttaa ctgcagcctt actacaatag atttcatggc gaaaatgaaa gagaatttca     240
agagggaaga cgataaattt ccaacgacaa cgactcttcg atccgaagat atacctcta      300 atttgtgtat aatcgacacc cttcaaaggt tgggggtcga tcaattcttc caatatgaaa     360
tcaacactat tctagataac acattcaggt tgtggcaaga aaaacacaaa gttatatatg     420
gcaatgttac tactcatgca atggcattta ggcttttgcg agtgaaagga tacgaagttt     480
catcagagga gttggctcca tatggtaacc aagaggctgt tagccagcaa acaaat        536

<210> SEQ ID NO 88
<211> LENGTH: 95
<212> TYPE: DNA
<213> ORGANISM: Salvia sclarea

<400> SEQUENCE: 88
ttgcatcttc ttggcaaaat gctttctttt ttatacacaa tctgcaacac ttttctccag      60
tgatattcaa ccatttcatt gatctctgca atggc                                95

<210> SEQ ID NO 89
<211> LENGTH: 55
<212> TYPE: DNA
<213> ORGANISM: Salvia sclarea

<400> SEQUENCE: 89
tgaagcccag aaccagaaag gacttcaaca actgcaaagg tggtatgcag attgt           55

```
<210> SEQ ID NO 90
<211> LENGTH: 53
<212> TYPE: DNA
<213> ORGANISM: Salvia sclarea

<400> SEQUENCE: 90
tactctgcat ccggattctc cttccattct tttactaatt caatgatctt gtc          53

<210> SEQ ID NO 91
<211> LENGTH: 2391
<212> TYPE: DNA
<213> ORGANISM: Salvia sclarea

<400> SEQUENCE: 91
atgtcgcttc ctctctccac ttgcaatgga tcacattttc ggagataccg cttgtctcct    60
gcttcagctt ctatggaaac tgggcttcaa actgctactt cagcaaaaat cgcctctatg   120
ccagcgtgct ttgaggagac gagagggagg atagcaaagt tgtttcataa ggatgaactt   180
tctgtgtcga catatgatac agcatgggtt gccatggtcc cttctccaac ttcgttagag   240
gaaccttgct cccccgattg tctaaactgg ttgctcgaga accagtgcca tgatggttcg   300
tgggcccgtc cccaccatca ctctttgcta atgaaagatg tcctttcttc taccttggcc   360
tgcattcttg ctcttaaaaa atggggagtt ggtgaaaaac agattaacag gggcttgcat   420
tttatggagt tgaattttgc ttcagctact gagaagtgtc agattactcc catgggattt   480
gatattgtat ttcctgccat gcttgattat gccagagact tctctttgga catgcattta   540
gagccaacta cgttgaatga tttgatacat aagagggatt tggagcttaa aagcaagcca   600 gattttcat cggatgggga agcctattgg gcatatatag ctgaaggaat ggggaattta   660
cggaactggg aatcagttat gaaatatcaa agaaggaatg gatctctttt caactgtcct   720
tccacgacag cagctgcttt tgttgcactg gcaattctg actgcctcaa ctacctgcat   780
tcagccttaa agaagtttgg gaatgcagtt cctgcagttt atcctctaga tatatattct   840
cacctgtgca tagttgacaa tcttgaaagg ttggggatca gccgttattt tttgactgag   900
attcaaagcg tgttagatga acacacagat gttggatgc agggcaatga agagatcttc   960
atggatgcct caacttgtgc tttagctttc cggatattgc gattgaacgg atacgatgta  1020
acttcagatc cggttacaaa aattcaacac gagtgctttt cgagttcctt tcatggaaat  1080
gtgatggaca ttaacacgac tcttgaatta tagggcat ctgaactcat actatatcca  1140
gatgaaagag atctagtgag acaaaattta aggcttaaac aaatactaga gcaagagcta  1200
tccaatggtt ttattcaatc atgtcaactt ggaagaagtg ttaatgcaga ggtgaaccag  1260
gctatcgagt atccatttta tgcaattatg acaggggttg caaaacggaa aaatatagag  1320
aactacaact tgataatac aagaattctg aaaacttcat attgttcacc aaattttggc  1380
aacaaggatt ttcttttttct gtccgtagag gacttcaatc tgtgtcaagc cacacatcgc  1440
gaagaactca gggaacttga agatgggtc gtagagaata gattggacga gctgcagttt  1500
gcaaggagta agtctgcata ttgttattt tctgcagcag caacctttc tgctccagaa  1560 ctacgtgatg cacgcatgtc gtgggccaaa ggtgtgttc tgactacagt gattgatgac  1620 tttttgacg tcggaggtc tatgaagaa ttgaagaact taattcattt ggttgaaaaa  1680
tgggatgtgg atgttagcac agaatgctct tcccataatg tccagataat attttcagca  1740
cttaagagca caatccgtga aattggatac aaagggttga agctacaagg gcgttgtatt  1800
actaaccata taattggcat ttggttagat ttgctgaatt ctatgatgaa agaaactgaa  1860
tgggctagag acaactatgt cccaacaatt gatgaatata tgagcaatgc atatgtgtca  1920
```

```
tttgctctgg ggccaattgt tctgccaact ctatatcttg ttgggccgaa gctctcagaa    1980
gagatggcaa accaccccga gtactataaa ctattcaaat tgatgagcac atgcggacgc    2040
cttttaaatg acatccgtgg ttatgagaga gaactcaaag atggtaaact gaacgcgcta    2100
tctttgtaca tggctaatca tggtggtgaa gtaagtaaag aagcagccat ttcagagatc    2160
aaaagttgga ttgagagcag taggagagaa ttactgagat tagttttgga ggggaagaag    2220
agtgtccttc caaagccatg caaggaatta ttttggcaca tgtgctctgt ggtccatcta    2280
ttctacagta aagacgacgg attcacctcg caggatttga ttcaagttgt aaatgcaatt    2340
attcacaaac ctattgtcct caaggaacaa acaggagcaa ggatataaaa g             2391

<210> SEQ ID NO 92
<211> LENGTH: 2316
<212> TYPE: DNA
<213> ORGANISM: Salvia sclarea

<400> SEQUENCE: 92
atggaaactg ggcttcaaac tgctacttca gcaaaaatcg cctctatgcc agcgtgcttt      60
gaggagacga gagggaggat agcaaagttg tttcataagg atgaactttc tgtgtcgaca     120
tatgatacag catgggttgc catggtccct tctccaactt cgttagagga accttgcttc     180
cccgattgtc taaactggtt gctcgagaac cagtgccatg atggttcgtg ggcccgtccc     240
caccatcact ctttgctaat gaaagatgtc cttttcttcta ccttggcctg cattcttgct     300
cttaaaaaat ggggagttgg tgaaaaacag attaacaggg gcttgcattt tatggagttg     360
aattttgctt cagctactga gaagtgtcag attactccca tgggatttga tattgtattt     420
cctgccatgc ttgattatgc cagagacttc tcttttggaca tgcatttaga gccaactacg     480
ttgaatgatt tgatacataa gagggatttg gagcttaaaa gcaagccaga tttttcatcg     540
gatggggaag cctattgggc atatatagct gaaggaatgg ggaatttacg gaactgggaa     600
tcagttatga aatatcaaag aaggaatgga tctctttttca actgtccttc cacgacagca     660
gctgcttttg ttgcactggg caattctgac tgcctcaact acctgcattc agccttaaag     720
aagtttggga atgcagttcc tgcagtttat cctctagata tatattctca cctgtgcata     780
gttgacaatc ttgaaaggtt ggggatcagc cgttattttt tgactgagat tcaaagcgtg     840
ttagatgaaa cacacagatg ttggatgcag ggcaatgaag agatcttcat ggatgcctca     900
acttgtgctt tagcttttcg gatattgcga ttgaacggat acgatgtaac ttcagatccg     960
gttacaaaaa ttcaacacga gtgcttttcg agttcctttc atggaaatgt gatggacatt    1020
aacacgactc ttgaattata tgggcatctg gaactcatac tatatccaga tgaaagagat    1080
ctagtgagac aaaatttaag gcttaaacaa atactagagc aagagctatc caatggtttt    1140
attcaatcat gtcaacttgg aagaagtgtt aatgcagagg tgaaccaggc tatcgagtat    1200
ccattttatg caattatgga cagggttgca aaacggaaaa atatagagaa ctacaacttt    1260
gataatacaa gaattctgaa aacttcatat tgttcaccaa ttttggcaa caaggatttt    1320 ctttttctgt ccgtagagga cttcaatctg tgtcaagcca cacatcgcga agaactcagg    1380
gaacttgaaa gatgggtcgt agagaataga ttggacgagc tgcagtttgc aaggagtaag    1440
tctgcatatt gttattttttc tgcagcagca acctttctg ctccagaact acgtgatgca    1500
cgcatgtcgt gggccaaagg tggtgttctg actacagtga ttgatgactt ttttgacgtc    1560
ggaggttcta tggaagaatt gaagaactta attcatttgg ttgaaaaatg ggatgtggat    1620
gttagcacag aatgctcttc ccataatgtc cagataatat tttcagcact aagagcaca    1680
```

```
atccgtgaaa ttggatacaa agggttgaag ctacaagggc gttgtattac taaccatata    1740
attggcattt ggttagattt gctgaattct atgatgaaag aaactgaatg ggctagagac    1800
aactatgtcc caacaattga tgaatatatg agcaatgcat atgtgtcatt tgctctgggg    1860
ccaattgttc tgccaactct atatcttgtt gggccgaagc tctcagaaga gatggcaaac    1920
caccccgagt actataaact attcaaattg atgagcacat gcggacgcct tttaaatgac    1980
atccgtggtt atgagagaga actcaaagat ggtaaactga acgcgctatc tttgtacatg    2040
gctaatcatg gtggtgaagt aagtaaagaa gcagccattt cagagatcaa aagttggatt    2100
gagagcagta ggagagaatt actgagatta gttttggagg ggaagaagag tgtccttcca    2160
aagccatgca aggaattatt ttggcacatg tgctctgtgg tccatctatt ctacagtaaa    2220
gacgacggat tcacctcgca ggatttgatt caagttgtaa atgcaattat tcacaaacct    2280
attgtcctca aggaacaaac aggagcaagg atataa                              2316

<210> SEQ ID NO 93
<211> LENGTH: 1578
<212> TYPE: DNA
<213> ORGANISM: Salvia sclarea

<400> SEQUENCE: 93
atggcgaaaa tgaaagagaa tttcaagagg gaagacgata aatttccaac gacaacgact      60
cttcgatccg aagatatacc ctctaatttg tgtataatcg acacccttca aaggttgggg     120
gtcgatcaat tcttccaata tgaaatcaac actattctag ataacacatt caggttgtgg     180
caagaaaaac acaaagttat atatggcaat gttactactc atgcaatggc atttaggctt     240
ttgcgagtga aaggatacga agtttcatca gaggagttgg ctccatatgg taaccaagag     300
gctgttagcc agcaaacaaa tgacctgccg atgattattg agctttatag agcagcaaat     360
gagagaatat atgaagaaga gaggagtctt gaaaaaattc ttgcttggac taccatcttt     420
ctcaataagc aagtgcaaga taactcaatt cccgacaaaa aactgcacaa actggtggaa     480
ttctacttga ggaattacaa aggcataacc ataagattgg gagctagacg aaacctcgag     540
ctatatgaca tgacctacta tcaagctctg aaatctacaa acaggttctc taatttatgc     600
aacgaagatt ttctagtttt cgcaaagcaa gatttcgata tacatgaagc ccagaaccag     660
aaaggacttc aacaactgca aggtggtat gcagattgta ggttggacac cttaaacttt     720
ggaagagatg tagttattat tgctaattat ttggcttcat taattattgg tgatcatgcg     780
tttgactatg ttcgtctcgc atttgccaaa acatctgtgc ttgtaacaat tatggatgat     840
tttttcgact gtcatggctc tagtcaagag tgtgacaaga tcattgaatt agtaaaagaa     900
tggaaggaga atccggatgc agagtacgga tctgaggagc ttgagatcct ttttatggcg     960
ttgtacaata cagtaaatga gttggcggag agggctcgtg ttgaacaggg cgtagtgtc    1020 aaagagtttc tagtcaaact gtgggttgaa atactctcag ctttcaagat agaattagat    1080
acatggagca atggcacgca gcaaagcttc gatgaataca tttcttcgtc gtggttgtcg    1140
aacggttccc ggctgacagg tctcctgacg atgcaattcg tcggagtaaa attgtccgat    1200
gaaatgctta tgagtgaaga gtgcactgat ttggctaggc atgtctgtat ggtcggccgg    1260
ctgctcaacg acgtgtgcag ttctgagagg gagcgcgagg aaaatattgc aggaaaaagt    1320
tatagcattc tactagcaac tgagaaagat ggaagaaaag ttagtgaaga tgaagccatt    1380
gcagagatca atgaaatggt tgaatatcac tggaaaaag tgttgcagat tgtgtataaa    1440
aaagaaagca ttttgccaag aagatgcaaa gatgtatttt tggagatggc taagggtacg    1500
```

```
tttatgctt atgggatcaa cgatgaattg acttctcctc agcaatccaa ggaagatatg    1560
aaatcctttg tcttttga                                                 1578
```

<210> SEQ ID NO 94
<211> LENGTH: 795
<212> TYPE: PRT
<213> ORGANISM: Salvia sclarea

<400> SEQUENCE: 94

```
Met Ser Leu Pro Leu Ser Thr Cys Asn Gly Ser His Phe Arg Arg Tyr
1               5                   10                  15

Arg Leu Ser Pro Ala Ser Ala Ser Met Glu Thr Gly Leu Gln Thr Ala
            20                  25                  30

Thr Ser Ala Lys Ile Ala Ser Met Pro Ala Cys Phe Glu Glu Thr Arg
        35                  40                  45

Gly Arg Ile Ala Lys Leu Phe His Lys Asp Glu Leu Ser Val Ser Thr
    50                  55                  60

Tyr Asp Thr Ala Trp Val Ala Met Val Pro Ser Pro Thr Ser Leu Glu
65                  70                  75                  80

Glu Pro Cys Phe Pro Asp Cys Leu Asn Trp Leu Leu Glu Asn Gln Cys
                85                  90                  95

His Asp Gly Ser Trp Ala Arg Pro His His His Ser Leu Leu Met Lys
            100                 105                 110

Asp Val Leu Ser Ser Thr Leu Ala Cys Ile Leu Ala Leu Lys Lys Trp
        115                 120                 125

Gly Val Gly Glu Lys Gln Ile Asn Arg Gly Leu His Phe Met Glu Leu
    130                 135                 140

Asn Phe Ala Ser Ala Thr Glu Lys Cys Gln Ile Thr Pro Met Gly Phe
145                 150                 155                 160

Asp Ile Val Phe Pro Ala Met Leu Asp Tyr Ala Arg Asp Phe Ser Leu
                165                 170                 175

Asp Met His Leu Glu Pro Thr Thr Leu Asn Asp Leu Ile His Lys Arg
            180                 185                 190

Asp Leu Glu Leu Lys Ser Lys Pro Asp Phe Ser Ser Asp Gly Glu Ala
        195                 200                 205

Tyr Trp Ala Tyr Ile Ala Glu Gly Met Gly Asn Leu Arg Asn Trp Glu
    210                 215                 220

Ser Val Met Lys Tyr Gln Arg Arg Asn Gly Ser Leu Phe Asn Cys Pro
225                 230                 235                 240

Ser Thr Thr Ala Ala Ala Phe Val Ala Leu Gly Asn Ser Asp Cys Leu
                245                 250                 255

Asn Tyr Leu His Ser Ala Leu Lys Lys Phe Gly Asn Ala Val Pro Ala
            260                 265                 270

Val Tyr Pro Leu Asp Ile Tyr Ser His Leu Cys Ile Val Asp Asn Leu
        275                 280                 285

Glu Arg Leu Gly Ile Ser Arg Tyr Phe Leu Thr Glu Ile Gln Ser Val
    290                 295                 300

Leu Asp Glu Thr His Arg Cys Trp Met Gln Gly Asn Glu Glu Ile Phe
305                 310                 315                 320

Met Asp Ala Ser Thr Cys Ala Leu Ala Phe Arg Ile Leu Arg Leu Asn
                325                 330                 335

Gly Tyr Asp Val Thr Ser Asp Pro Val Thr Lys Ile Gln His Glu Cys
            340                 345                 350
```

-continued

```
Phe Ser Ser Ser Phe His Gly Asn Val Met Asp Ile Asn Thr Thr Leu
        355                 360                 365

Glu Leu Tyr Arg Ala Ser Glu Leu Ile Leu Tyr Pro Asp Glu Arg Asp
370                 375                 380

Leu Val Arg Gln Asn Leu Arg Leu Lys Gln Ile Leu Glu Gln Glu Leu
385                 390                 395                 400

Ser Asn Gly Phe Ile Gln Ser Cys Gln Leu Gly Arg Ser Val Asn Ala
                405                 410                 415

Glu Val Asn Gln Ala Ile Glu Tyr Pro Phe Tyr Ala Ile Met Asp Arg
            420                 425                 430

Val Ala Lys Arg Lys Asn Ile Glu Asn Tyr Asn Phe Asp Asn Thr Arg
        435                 440                 445

Ile Leu Lys Thr Ser Tyr Cys Ser Pro Asn Phe Gly Asn Lys Asp Phe
    450                 455                 460

Leu Phe Leu Ser Val Glu Asp Phe Asn Leu Cys Gln Ala Thr His Arg
465                 470                 475                 480

Glu Glu Leu Arg Glu Leu Arg Trp Val Glu Asn Arg Leu Asp
                485                 490                 495

Glu Leu Gln Phe Ala Arg Ser Lys Ser Ala Tyr Cys Tyr Phe Ser Ala
                500                 505                 510

Ala Ala Thr Phe Ser Ala Pro Glu Leu Arg Asp Ala Arg Met Ser Trp
            515                 520                 525

Ala Lys Gly Gly Val Leu Thr Thr Val Ile Asp Asp Phe Phe Asp Val
530                 535                 540

Gly Gly Ser Met Glu Glu Leu Lys Asn Leu Ile His Leu Val Glu Lys
545                 550                 555                 560

Trp Asp Val Asp Val Ser Thr Glu Cys Ser Ser His Asn Val Gln Ile
                565                 570                 575

Ile Phe Ser Ala Leu Lys Ser Thr Ile Arg Glu Ile Gly Tyr Lys Gly
            580                 585                 590

Leu Lys Leu Gln Gly Arg Cys Ile Thr Asn His Ile Ile Gly Ile Trp
        595                 600                 605

Leu Asp Leu Leu Asn Ser Met Met Lys Glu Thr Glu Trp Ala Arg Asp
    610                 615                 620

Asn Tyr Val Pro Thr Ile Asp Glu Tyr Met Ser Asn Ala Tyr Val Ser
625                 630                 635                 640

Phe Ala Leu Gly Pro Ile Val Leu Pro Thr Leu Tyr Leu Val Gly Pro
                645                 650                 655

Lys Leu Ser Glu Glu Met Ala Asn His Pro Glu Tyr Tyr Lys Leu Phe
            660                 665                 670

Lys Leu Met Ser Thr Cys Gly Arg Leu Leu Asn Asp Ile Arg Gly Tyr
        675                 680                 685

Glu Arg Glu Leu Lys Asp Gly Lys Leu Asn Ala Leu Ser Leu Tyr Met
    690                 695                 700

Ala Asn His Gly Gly Glu Val Ser Lys Glu Ala Ile Ser Glu Ile
705                 710                 715                 720

Lys Ser Trp Ile Glu Ser Ser Arg Arg Glu Leu Leu Arg Leu Val Leu
                725                 730                 735

Glu Gly Lys Lys Ser Val Leu Pro Lys Pro Cys Lys Glu Leu Phe Trp
            740                 745                 750

His Met Cys Ser Val Val His Leu Phe Tyr Ser Lys Asp Asp Gly Phe
        755                 760                 765

Thr Ser Gln Asp Leu Ile Gln Val Val Asn Ala Ile Ile His Lys Pro
    770                 775                 780
```

```
Ile Val Leu Lys Glu Gln Thr Gly Ala Arg Ile
785                 790                 795

<210> SEQ ID NO 95
<211> LENGTH: 771
<212> TYPE: PRT
<213> ORGANISM: Salvia sclarea

<400> SEQUENCE: 95

Met Glu Thr Gly Leu Gln Thr Ala Thr Ser Ala Lys Ile Ala Ser Met
1               5                   10                  15

Pro Ala Cys Phe Glu Glu Thr Arg Gly Arg Ile Ala Lys Leu Phe His
            20                  25                  30

Lys Asp Glu Leu Ser Val Ser Thr Tyr Asp Thr Ala Trp Val Ala Met
        35                  40                  45

Val Pro Ser Pro Thr Ser Leu Glu Glu Pro Cys Phe Pro Asp Cys Leu
    50                  55                  60

Asn Trp Leu Leu Glu Asn Gln Cys His Asp Gly Ser Trp Ala Arg Pro
65                  70                  75                  80

His His His Ser Leu Leu Met Lys Asp Val Leu Ser Ser Thr Leu Ala
                85                  90                  95

Cys Ile Leu Ala Leu Lys Lys Trp Gly Val Gly Glu Lys Gln Ile Asn
            100                 105                 110

Arg Gly Leu His Phe Met Glu Leu Asn Phe Ala Ser Ala Thr Glu Lys
        115                 120                 125

Cys Gln Ile Thr Pro Met Gly Phe Asp Ile Val Phe Pro Ala Met Leu
    130                 135                 140

Asp Tyr Ala Arg Asp Phe Ser Leu Asp Met His Leu Glu Pro Thr Thr
145                 150                 155                 160

Leu Asn Asp Leu Ile His Lys Arg Asp Leu Glu Leu Lys Ser Lys Pro
                165                 170                 175

Asp Phe Ser Ser Asp Gly Glu Ala Tyr Trp Ala Tyr Ile Ala Glu Gly
            180                 185                 190

Met Gly Asn Leu Arg Asn Trp Glu Ser Val Met Lys Tyr Gln Arg Arg
        195                 200                 205

Asn Gly Ser Leu Phe Asn Cys Pro Ser Thr Thr Ala Ala Ala Phe Val
    210                 215                 220

Ala Leu Gly Asn Ser Asp Cys Leu Asn Tyr Leu His Ser Ala Leu Lys
225                 230                 235                 240

Lys Phe Gly Asn Ala Val Pro Ala Val Tyr Pro Leu Asp Ile Tyr Ser
                245                 250                 255

His Leu Cys Ile Val Asp Asn Leu Glu Arg Leu Gly Ile Ser Arg Tyr
            260                 265                 270

Phe Leu Thr Glu Ile Gln Ser Val Leu Asp Glu Thr His Arg Cys Trp
        275                 280                 285

Met Gln Gly Asn Glu Glu Ile Phe Met Asp Ala Ser Thr Cys Ala Leu
    290                 295                 300

Ala Phe Arg Ile Leu Arg Leu Asn Gly Tyr Asp Val Thr Ser Asp Pro
305                 310                 315                 320

Val Thr Lys Ile Gln His Glu Cys Phe Ser Ser Phe His Gly Asn
                325                 330                 335

Val Met Asp Ile Asn Thr Thr Leu Glu Leu Tyr Arg Ala Ser Glu Leu
            340                 345                 350

Ile Leu Tyr Pro Asp Glu Arg Asp Leu Val Arg Gln Asn Leu Arg Leu
        355                 360                 365
```

```
Lys Gln Ile Leu Glu Gln Glu Leu Ser Asn Gly Phe Ile Gln Ser Cys
    370                 375                 380
Gln Leu Gly Arg Ser Val Asn Ala Glu Val Asn Gln Ala Ile Glu Tyr
385                 390                 395                 400
Pro Phe Tyr Ala Ile Met Asp Arg Val Ala Lys Arg Lys Asn Ile Glu
                405                 410                 415
Asn Tyr Asn Phe Asp Asn Thr Arg Ile Leu Lys Thr Ser Tyr Cys Ser
            420                 425                 430
Pro Asn Phe Gly Asn Lys Asp Phe Leu Phe Leu Ser Val Glu Asp Phe
        435                 440                 445
Asn Leu Cys Gln Ala Thr His Arg Glu Glu Leu Arg Glu Leu Glu Arg
    450                 455                 460
Trp Val Val Glu Asn Arg Leu Asp Glu Leu Gln Phe Ala Arg Ser Lys
465                 470                 475                 480
Ser Ala Tyr Cys Tyr Phe Ser Ala Ala Thr Phe Ser Ala Pro Glu
                485                 490                 495
Leu Arg Asp Ala Arg Met Ser Trp Ala Lys Gly Gly Val Leu Thr Thr
            500                 505                 510
Val Ile Asp Asp Phe Phe Asp Val Gly Gly Ser Met Glu Glu Leu Lys
        515                 520                 525
Asn Leu Ile His Leu Val Glu Lys Trp Asp Val Asp Val Ser Thr Glu
    530                 535                 540
Cys Ser Ser His Asn Val Gln Ile Ile Phe Ser Ala Leu Lys Ser Thr
545                 550                 555                 560
Ile Arg Glu Ile Gly Tyr Lys Gly Leu Lys Leu Gln Gly Arg Cys Ile
                565                 570                 575
Thr Asn His Ile Ile Gly Ile Trp Leu Asp Leu Leu Asn Ser Met Met
            580                 585                 590
Lys Glu Thr Glu Trp Ala Arg Asp Asn Tyr Val Pro Thr Ile Asp Glu
        595                 600                 605
Tyr Met Ser Asn Ala Tyr Val Ser Phe Ala Leu Gly Pro Ile Val Leu
    610                 615                 620
Pro Thr Leu Tyr Leu Val Gly Pro Lys Leu Ser Glu Glu Met Ala Asn
625                 630                 635                 640
His Pro Glu Tyr Tyr Lys Leu Phe Lys Leu Met Ser Thr Cys Gly Arg
                645                 650                 655
Leu Leu Asn Asp Ile Arg Gly Tyr Glu Arg Glu Leu Lys Asp Gly Lys
            660                 665                 670
Leu Asn Ala Leu Ser Leu Tyr Met Ala Asn His Gly Gly Glu Val Ser
        675                 680                 685
Lys Glu Ala Ala Ile Ser Glu Ile Lys Ser Trp Ile Glu Ser Ser Arg
    690                 695                 700
Arg Glu Leu Leu Arg Leu Val Leu Glu Gly Lys Lys Ser Val Leu Pro
705                 710                 715                 720
Lys Pro Cys Lys Glu Leu Phe Trp His Met Cys Ser Val Val His Leu
                725                 730                 735
Phe Tyr Ser Lys Asp Asp Gly Phe Thr Ser Gln Asp Leu Ile Gln Val
            740                 745                 750
Val Asn Ala Ile Ile His Lys Pro Ile Val Leu Lys Glu Gln Thr Gly
        755                 760                 765
Ala Arg Ile
770
```

<210> SEQ ID NO 96
<211> LENGTH: 525
<212> TYPE: PRT
<213> ORGANISM: Salvia sclarea

<400> SEQUENCE: 96

Met Ala Lys Met Lys Glu Asn Phe Lys Arg Glu Asp Asp Lys Phe Pro
1               5                   10                  15

Thr Thr Thr Thr Leu Arg Ser Glu Asp Ile Pro Ser Asn Leu Cys Ile
            20                  25                  30

Ile Asp Thr Leu Gln Arg Leu Gly Val Asp Gln Phe Phe Gln Tyr Glu
        35                  40                  45

Ile Asn Thr Ile Leu Asp Asn Thr Phe Arg Leu Trp Gln Glu Lys His
    50                  55                  60

Lys Val Ile Tyr Gly Asn Val Thr Thr His Ala Met Ala Phe Arg Leu
65                  70                  75                  80

Leu Arg Val Lys Gly Tyr Glu Val Ser Glu Glu Leu Ala Pro Tyr
                85                  90                  95

Gly Asn Gln Glu Ala Val Ser Gln Gln Thr Asn Asp Leu Pro Met Ile
            100                 105                 110

Ile Glu Leu Tyr Arg Ala Ala Asn Glu Arg Ile Tyr Glu Glu Arg
        115                 120                 125

Ser Leu Glu Lys Ile Leu Ala Trp Thr Thr Ile Phe Leu Asn Lys Gln
130                 135                 140

Val Gln Asp Asn Ser Ile Pro Asp Lys Lys Leu His Lys Leu Val Glu
145                 150                 155                 160

Phe Tyr Leu Arg Asn Tyr Lys Gly Ile Thr Ile Arg Leu Gly Ala Arg
                165                 170                 175

Arg Asn Leu Glu Leu Tyr Asp Met Thr Tyr Tyr Gln Ala Leu Lys Ser
            180                 185                 190

Thr Asn Arg Phe Ser Asn Leu Cys Asn Glu Asp Phe Leu Val Phe Ala
        195                 200                 205

Lys Gln Asp Phe Asp Ile His Glu Ala Gln Asn Gln Lys Gly Leu Gln
    210                 215                 220

Gln Leu Gln Arg Trp Tyr Ala Asp Cys Arg Leu Asp Thr Leu Asn Phe
225                 230                 235                 240

Gly Arg Asp Val Val Ile Ile Ala Asn Tyr Leu Ala Ser Leu Ile Ile
                245                 250                 255

Gly Asp His Ala Phe Asp Tyr Val Arg Leu Ala Phe Ala Lys Thr Ser
            260                 265                 270

Val Leu Val Thr Ile Met Asp Asp Phe Phe Asp Cys His Gly Ser Ser
        275                 280                 285

Gln Glu Cys Asp Lys Ile Ile Glu Leu Val Lys Glu Trp Lys Glu Asn
    290                 295                 300

Pro Asp Ala Glu Tyr Gly Ser Glu Glu Leu Glu Ile Leu Phe Met Ala
305                 310                 315                 320

Leu Tyr Asn Thr Val Asn Glu Leu Ala Glu Arg Ala Arg Val Glu Gln
                325                 330                 335

Gly Arg Ser Val Lys Glu Phe Leu Val Lys Leu Trp Val Glu Ile Leu
            340                 345                 350

Ser Ala Phe Lys Ile Glu Leu Asp Thr Trp Ser Asn Gly Thr Gln Gln
        355                 360                 365

Ser Phe Asp Glu Tyr Ile Ser Ser Trp Leu Ser Asn Gly Ser Arg
    370                 375                 380

```
Leu Thr Gly Leu Leu Thr Met Gln Phe Val Gly Val Lys Leu Ser Asp
385                 390                 395                 400

Glu Met Leu Met Ser Glu Glu Cys Thr Asp Leu Ala Arg His Val Cys
            405                 410                 415

Met Val Gly Arg Leu Leu Asn Asp Val Cys Ser Ser Glu Arg Glu Arg
            420                 425                 430

Glu Glu Asn Ile Ala Gly Lys Ser Tyr Ser Ile Leu Leu Ala Thr Glu
            435                 440                 445

Lys Asp Gly Arg Lys Val Ser Glu Asp Glu Ala Ile Ala Glu Ile Asn
            450                 455                 460

Glu Met Val Glu Tyr His Trp Arg Lys Val Leu Gln Ile Val Tyr Lys
465                 470                 475                 480

Lys Glu Ser Ile Leu Pro Arg Arg Cys Lys Asp Val Phe Leu Glu Met
                485                 490                 495

Ala Lys Gly Thr Phe Tyr Ala Tyr Gly Ile Asn Asp Glu Leu Thr Ser
            500                 505                 510

Pro Gln Gln Ser Lys Glu Asp Met Lys Ser Phe Val Phe
            515                 520                 525

<210> SEQ ID NO 97
<211> LENGTH: 805
<212> TYPE: PRT
<213> ORGANISM: Salvia sclarea

<400> SEQUENCE: 97

Met Gly Ser Ser His His His His His His Ser Ser Gly Leu Val Pro
1               5                   10                  15

Arg Gly Ser His Met Thr Ser Val Asn Leu Ser Arg Ala Pro Ala Ala
            20                  25                  30

Ile Thr Arg Arg Arg Leu Gln Leu Gln Pro Glu Phe His Ala Glu Cys
        35                  40                  45

Ser Trp Leu Lys Ser Ser Ser Lys His Ala Pro Leu Thr Leu Ser Cys
    50                  55                  60

Gln Ile Arg Pro Lys Gln Leu Ser Gln Ile Ala Glu Leu Arg Val Thr
65                  70                  75                  80

Ser Leu Asp Ala Ser Gln Ala Ser Glu Lys Asp Ile Ser Leu Val Gln
                85                  90                  95

Thr Pro His Lys Val Glu Val Asn Glu Lys Ile Glu Ser Ile Glu
            100                 105                 110

Tyr Val Gln Asn Leu Leu Met Thr Ser Gly Asp Gly Arg Ile Ser Val
            115                 120                 125

Ser Pro Tyr Asp Thr Ala Val Ile Ala Leu Ile Lys Asp Leu Lys Gly
    130                 135                 140

Arg Asp Ala Pro Gln Phe Pro Ser Cys Leu Glu Trp Ile Ala His His
145                 150                 155                 160

Gln Leu Ala Asp Gly Ser Trp Gly Asp Glu Phe Phe Cys Ile Tyr Asp
                165                 170                 175

Arg Ile Leu Asn Thr Leu Ala Cys Val Val Ala Leu Lys Ser Trp Asn
            180                 185                 190

Leu His Ser Asp Ile Ile Glu Lys Gly Val Thr Tyr Ile Lys Glu Asn
            195                 200                 205

Val His Lys Leu Lys Gly Ala Asn Val Glu His Arg Thr Ala Gly Phe
    210                 215                 220

Glu Leu Val Val Pro Thr Phe Met Gln Met Ala Thr Asp Leu Gly Ile
225                 230                 235                 240
```

-continued

```
Gln Asp Leu Pro Tyr Asp His Pro Leu Ile Lys Glu Ile Ala Asp Thr
                245                 250                 255

Lys Gln Gln Arg Leu Lys Glu Ile Pro Lys Asp Leu Val Tyr Gln Met
            260                 265                 270

Pro Thr Asn Leu Leu Tyr Ser Leu Glu Gly Leu Gly Asp Leu Glu Trp
        275                 280                 285

Glu Arg Leu Leu Lys Leu Gln Ser Gly Asn Gly Ser Phe Leu Thr Ser
    290                 295                 300

Pro Ser Ser Thr Ala Ala Val Leu Met His Thr Lys Asp Glu Lys Cys
305                 310                 315                 320

Leu Lys Tyr Ile Glu Asn Ala Leu Lys Asn Cys Asp Gly Gly Ala Pro
                325                 330                 335

His Thr Tyr Pro Val Asp Ile Phe Ser Arg Leu Trp Ala Ile Asp Arg
            340                 345                 350

Leu Gln Arg Leu Gly Ile Ser Arg Phe Phe Gln His Glu Ile Lys Tyr
        355                 360                 365

Phe Leu Asp His Ile Glu Ser Val Trp Glu Glu Thr Gly Val Phe Ser
    370                 375                 380

Gly Arg Tyr Thr Lys Phe Ser Asp Ile Asp Asp Thr Ser Met Gly Val
385                 390                 395                 400

Arg Leu Leu Lys Met His Gly Tyr Asp Val Asp Pro Asn Val Leu Lys
                405                 410                 415

His Phe Lys Gln Gln Asp Gly Lys Phe Ser Cys Tyr Ile Gly Gln Ser
            420                 425                 430

Val Glu Ser Ala Ser Pro Met Tyr Asn Leu Tyr Arg Ala Ala Gln Leu
        435                 440                 445

Arg Phe Pro Gly Glu Glu Val Leu Glu Ala Thr Lys Phe Ala Phe
    450                 455                 460

Asn Phe Leu Gln Glu Met Leu Val Lys Asp Arg Leu Gln Glu Arg Trp
465                 470                 475                 480

Val Ile Ser Asp His Leu Phe Asp Glu Ile Lys Leu Gly Leu Lys Met
                485                 490                 495

Pro Trp Tyr Ala Thr Leu Pro Arg Val Glu Ala Ala Tyr Tyr Leu Asp
            500                 505                 510

His Tyr Ala Gly Ser Gly Asp Val Trp Ile Gly Lys Ser Phe Tyr Arg
        515                 520                 525

Met Pro Glu Ile Ser Asn Asp Thr Tyr Lys Glu Leu Ala Ile Leu Asp
    530                 535                 540

Phe Asn Arg Cys Gln Thr Gln His Gln Leu Glu Trp Ile His Met Gln
545                 550                 555                 560

Glu Trp Tyr Asp Arg Cys Ser Leu Ser Glu Phe Gly Ile Ser Lys Arg
                565                 570                 575

Glu Leu Leu Arg Ser Tyr Phe Leu Ala Ala Ala Thr Ile Phe Glu Pro
            580                 585                 590

Glu Arg Thr Gln Glu Arg Leu Leu Trp Ala Lys Thr Arg Ile Leu Ser
        595                 600                 605

Lys Met Ile Thr Ser Phe Val Asn Ile Ser Gly Thr Thr Leu Ser Leu
    610                 615                 620

Asp Tyr Asn Phe Asn Gly Leu Asp Glu Ile Ile Ser Ser Ala Asn Glu
625                 630                 635                 640

Asp Gln Gly Leu Ala Gly Thr Leu Leu Ala Thr Phe His Gln Leu Leu
                645                 650                 655

Asp Gly Phe Asp Ile Tyr Thr Leu His Gln Leu Lys His Val Trp Ser
            660                 665                 670
```

-continued

```
Gln Trp Phe Met Lys Val Gln Gln Gly Glu Gly Ser Gly Gly Glu Asp
            675                 680                 685

Ala Val Leu Leu Ala Asn Thr Leu Asn Ile Cys Ala Gly Leu Asn Glu
        690                 695                 700

Asp Val Leu Ser Asn Asn Glu Tyr Thr Ala Leu Ser Thr Leu Thr Asn
705                 710                 715                 720

Lys Ile Cys Asn Arg Leu Ala Gln Ile Gln Asp Asn Lys Ile Leu Gln
                725                 730                 735

Val Val Asp Gly Ser Ile Lys Asp Lys Glu Leu Glu Gln Asp Met Gln
            740                 745                 750

Ala Leu Val Lys Leu Val Leu Gln Glu Asn Gly Gly Ala Val Asp Arg
        755                 760                 765

Asn Ile Arg His Thr Phe Leu Ser Val Ser Lys Thr Phe Tyr Tyr Asp
770                 775                 780

Ala Tyr His Asp Asp Glu Thr Thr Asp Leu His Ile Phe Lys Val Leu
785                 790                 795                 800

Phe Arg Pro Val Val
                805

<210> SEQ ID NO 98
<211> LENGTH: 804
<212> TYPE: PRT
<213> ORGANISM: Salvia sclarea

<400> SEQUENCE: 98

Met Gly Ser Ser His His His His His His Ser Ser Gly Leu Val Pro
1               5                   10                  15

Arg Gly Ser His Met Thr Ser Val Asn Leu Ser Arg Ala Pro Ala Ala
            20                  25                  30

Ile Ile Arg Arg Arg Leu Gln Leu Gln Pro Glu Phe His Ala Glu Cys
        35                  40                  45

Ser Trp Leu Lys Ser Ser Ser Lys His Ala Pro Phe Thr Leu Ser Cys
    50                  55                  60

Gln Ile Arg Pro Lys Gln Leu Ser Gln Ile Ala Glu Leu Arg Val Thr
65                  70                  75                  80

Ser Leu Asp Ala Ser Gln Ala Ser Glu Lys Asp Ile Ser Leu Val Gln
                85                  90                  95

Thr Pro His Lys Val Glu Val Asn Glu Lys Ile Glu Glu Ser Ile Glu
            100                 105                 110

Tyr Val Gln Asn Leu Leu Met Thr Ser Gly Asp Gly Arg Ile Ser Val
        115                 120                 125

Ser Pro Tyr Asp Thr Ala Val Ile Ala Leu Ile Lys Asp Leu Lys Gly
    130                 135                 140

Arg Asp Ala Pro Gln Phe Pro Ser Cys Leu Glu Trp Ile Ala His His
145                 150                 155                 160

Gln Leu Ala Asp Gly Ser Trp Gly Asp Glu Phe Phe Cys Ile Tyr Asp
                165                 170                 175

Arg Ile Leu Asn Thr Leu Ala Cys Val Val Ala Leu Lys Ser Trp Asn
            180                 185                 190

Leu Gln Ser Asp Ile Ile Glu Lys Gly Val Thr Tyr Ile Lys Glu Asn
        195                 200                 205

Val His Lys Leu Lys Gly Ala Asn Val Glu His Arg Thr Ala Gly Phe
    210                 215                 220

Glu Leu Val Val Pro Thr Phe Met Gln Met Ala Thr Asp Leu Gly Ile
225                 230                 235                 240
```

-continued

```
Gln Gly Leu Pro Tyr Asp His Pro Leu Ile Lys Glu Ile Ala Asp Thr
            245                 250                 255
Lys Gln Gln Arg Leu Lys Glu Ile Pro Lys Asp Leu Val Tyr Gln Met
            260                 265                 270
Pro Thr Asn Leu Leu Tyr Ser Leu Glu Gly Leu Gly Asp Leu Glu Trp
            275                 280                 285
Glu Arg Leu Leu Lys Leu Gln Ser Gly Asn Gly Ser Phe Leu Thr Ser
            290                 295                 300
Pro Ser Ser Thr Ala Ala Val Leu Met His Thr Lys Asp Glu Lys Cys
305                 310                 315                 320
Leu Lys Tyr Ile Glu Asn Ala Leu Lys Asn Cys Asp Gly Gly Ala Pro
            325                 330                 335
His Thr Tyr Pro Val Asp Ile Phe Ser Arg Leu Trp Ala Ile Asp Arg
            340                 345                 350
Leu Gln Arg Leu Gly Ile Ser Arg Phe Phe Gln His Glu Ile Lys Tyr
            355                 360                 365
Phe Leu Asp His Ile Glu Ser Val Trp Glu Glu Thr Gly Val Phe Ser
            370                 375                 380
Gly Arg Tyr Thr Lys Phe Ser Asp Ile Asp Asp Thr Ser Met Gly Val
385                 390                 395                 400
Arg Leu Leu Lys Met His Gly Tyr Asp Val Asp Pro Asn Val Leu Lys
            405                 410                 415
His Phe Lys Gln Gln Asp Gly Lys Phe Ser Cys Tyr Ile Gly Gln Ser
            420                 425                 430
Val Glu Ser Ala Ser Pro Met Tyr Asn Leu Tyr Arg Ala Ala Gln Leu
            435                 440                 445
Arg Phe Pro Gly Glu Glu Val Leu Glu Glu Ala Thr Lys Phe Ala Phe
            450                 455                 460
Asn Phe Leu Gln Glu Met Leu Val Lys Asp Arg Leu Gln Glu Arg Trp
465                 470                 475                 480
Val Ile Ser Asp His Leu Phe Asp Glu Ile Lys Leu Gly Leu Lys Met
            485                 490                 495
Pro Trp Tyr Ala Thr Leu Pro Arg Val Glu Ala Ala Tyr Tyr Leu Asp
            500                 505                 510
His Tyr Ala Gly Ser Gly Asp Val Trp Ile Gly Lys Ser Phe Tyr Arg
            515                 520                 525
Met Pro Glu Ile Ser Asn Asp Thr Tyr Lys Glu Leu Ala Ile Leu Asp
            530                 535                 540
Phe Asn Arg Cys Gln Thr Gln His Gln Leu Glu Trp Ile Gln Met Gln
545                 550                 555                 560
Glu Trp Tyr Asp Arg Cys Ser Leu Ser Glu Phe Gly Ile Ser Lys Arg
            565                 570                 575
Glu Leu Leu Arg Ser Tyr Phe Leu Ala Ala Ala Thr Ile Phe Glu Pro
            580                 585                 590
Glu Arg Thr Gln Glu Arg Leu Leu Trp Ala Lys Thr Arg Ile Leu Ser
            595                 600                 605
Lys Met Ile Thr Ser Phe Val Asn Ile Ser Gly Thr Thr Leu Ser Leu
            610                 615                 620
Asp Tyr Asn Phe Asn Gly Leu Asp Glu Ile Ile Ser Ala Asn Glu Asp
625                 630                 635                 640
Gln Gly Leu Ala Gly Thr Leu Leu Ala Thr Phe His Gln Leu Leu Asp
            645                 650                 655
```

```
Gly Phe Asp Ile Tyr Thr Leu His Gln Leu Lys His Val Trp Ser Gln
                660                 665                 670

Trp Phe Met Lys Val Gln Gly Glu Gly Ser Gly Glu Asp Ala
        675                 680                 685

Val Leu Leu Ala Asn Thr Leu Asn Ile Cys Ala Gly Leu Asn Glu Asp
        690                 695                 700

Val Leu Ser Asn Asn Glu Tyr Thr Ala Leu Ser Thr Leu Thr Asn Lys
705                 710                 715                 720

Ile Cys Asn Arg Leu Ala Gln Ile Gln Asp Asn Lys Ile Leu Gln Val
                725                 730                 735

Val Asp Gly Ser Ile Lys Asp Lys Glu Leu Gln Asp Met Gln Ala
        740                 745                 750

Leu Val Lys Leu Val Leu Gln Glu Asn Gly Gly Ala Val Asp Arg Asn
        755                 760                 765

Ile Arg His Thr Phe Leu Ser Val Ser Lys Thr Phe Tyr Tyr Asp Ala
        770                 775                 780

Tyr His Asp Asp Glu Thr Thr Asp Leu His Ile Phe Lys Val Leu Phe
785                 790                 795                 800

Arg Pro Val Val

<210> SEQ ID NO 99
<211> LENGTH: 816
<212> TYPE: PRT
<213> ORGANISM: Oryza sativa

<400> SEQUENCE: 99

Met Met Leu Leu Ser Ser Ser Tyr Ser Gly Gly Gln Phe Pro Gly Val
1               5                   10                  15

Ser Pro Leu Gly Thr Arg Pro Lys Arg Ser Thr Thr Val Val Pro Leu
            20                  25                  30

Pro Val Val Thr Arg Ala Thr Ala Gly Gly Val Arg Asn Asn Leu Glu
        35                  40                  45

Val Val Gly Asn Ala Gly Thr Leu Gln Gly Met Asp Ile Asp Glu Leu
    50                  55                  60

Arg Val Ile Val Arg Lys Gln Leu Gln Gly Val Glu Leu Ser Pro Ser
65                  70                  75                  80

Ser Tyr Asp Thr Ala Trp Val Ala Met Val Pro Val Gln Gly Ser Pro
                85                  90                  95

Gln Ser Pro Cys Phe Pro Gln Cys Val Glu Trp Ile Leu Gln Asn Gln
            100                 105                 110

Gln Glu Asp Gly Ser Trp Gly His Ser Ala Gly Pro Ser Gly Glu Val
        115                 120                 125

Asn Lys Asp Ile Leu Leu Ser Thr Leu Ala Cys Val Leu Ala Leu Asn
    130                 135                 140

Thr Trp Asn Val Gly Gln Asp His Ile Arg Arg Gly Leu Ser Phe Ile
145                 150                 155                 160

Gly Arg Asn Phe Ser Val Ala Ile Asp Gly Gln Cys Ala Ala Pro Val
                165                 170                 175

Gly Phe Asn Ile Thr Phe Ser Gly Met Leu His Leu Ala Ile Gly Met
            180                 185                 190

Gly Leu Lys Phe Pro Val Met Glu Thr Asp Ile Asp Ser Ile Phe Arg
        195                 200                 205

Leu Arg Glu Val Glu Phe Glu Arg Asp Ala Gly Gly Thr Ala Ser Ala
    210                 215                 220
```

```
Arg Lys Ala Phe Met Ala Tyr Val Ser Glu Gly Leu Gly Arg Glu Gln
225                 230                 235                 240

Asp Trp Asp His Val Met Ala Tyr Gln Arg Lys Asn Gly Ser Leu Phe
                245                 250                 255

Asn Ser Pro Ser Thr Thr Ala Ala Ser Ala Ile His Ser Cys Asn Asp
            260                 265                 270

Arg Ala Leu Asp Tyr Leu Val Ser Leu Thr Ser Lys Leu Gly Gly Pro
            275                 280                 285

Val Pro Ala Ile His Pro Asp Lys Val Tyr Ser Gln Leu Cys Met Val
        290                 295                 300

Asp Thr Leu Glu Lys Met Gly Ile Ser Ser Asp Phe Ala Cys Asp Ile
305                 310                 315                 320

Arg Asp Ile Leu Asp Met Thr Tyr Ser Cys Trp Met Gln Asp Glu Glu
                325                 330                 335

Glu Ile Met Leu Asp Met Ala Thr Cys Ala Lys Ala Phe Arg Leu Leu
                340                 345                 350

Arg Met His Gly Tyr Asp Val Ser Ser Glu Gly Met Ala Arg Phe Ala
                355                 360                 365

Glu Arg Ser Ser Phe Asp Asp Ser Ile His Ala Tyr Leu Asn Asp Thr
370                 375                 380

Lys Pro Leu Leu Glu Leu Tyr Lys Ser Ser Gln Leu His Phe Leu Glu
385                 390                 395                 400

Glu Asp Leu Ile Leu Glu Asn Ile Ser Ser Trp Ser Ala Lys Leu Leu
                405                 410                 415

Lys Gln Gln Leu Ser Ser Asn Lys Ile Met Lys Ser Leu Met Pro Glu
                420                 425                 430

Val Glu Tyr Ala Leu Lys Tyr Pro Leu Tyr Ser Thr Val Asp Ala Leu
                435                 440                 445

Glu His Arg Gly Asn Ile Glu Arg Phe Asn Val Asn Gly Phe Gln Arg
                450                 455                 460

Pro Lys Ser Gly Tyr Cys Gly Ser Gly Ala Asp Lys Glu Ile Leu Ala
465                 470                 475                 480

Leu Ala Val Asp Lys Phe His Tyr Asn Gln Ser Val Tyr Gln Gln Glu
                485                 490                 495

Leu Arg Tyr Leu Glu Ser Trp Val Ala Glu Phe Gly Leu Asp Glu Leu
                500                 505                 510

Lys Phe Ala Arg Val Ile Pro Leu Gln Ser Leu Leu Ser Ala Leu Val
                515                 520                 525

Pro Leu Phe Pro Ala Glu Leu Ser Asp Ala Arg Ile Ala Phe Ser Gln
530                 535                 540

Asn Cys Met Leu Thr Thr Met Val Asp Asp Phe Phe Asp Gly Gly Gly
545                 550                 555                 560

Ser Met Glu Glu Met Val Asn Phe Val Ala Leu Ile Asp Glu Trp Asp
                565                 570                 575

Asn His Gly Glu Ile Gly Phe Cys Ser Asn Asn Val Glu Ile Met Phe
                580                 585                 590

Asn Ala Ile Tyr Asn Thr Thr Lys Arg Asn Cys Ala Lys Ala Ala Leu
                595                 600                 605

Val Gln Asn Arg Cys Val Met Asp His Ile Ala Lys Gln Trp Gln Val
                610                 615                 620

Met Val Arg Ala Met Lys Thr Glu Ala Glu Trp Ala Ala Ser Arg His
625                 630                 635                 640

Ile Pro Ala Thr Met Glu Glu Tyr Met Ser Val Gly Glu Pro Ser Phe
                645                 650                 655
```

```
Ala Leu Gly Pro Ile Val Pro Leu Ser Ala Tyr Leu Leu Gly Glu Glu
            660                 665                 670

Leu Pro Glu Glu Ala Val Arg Ser Pro Glu Tyr Gly Gln Leu Leu Arg
        675                 680                 685

His Ala Ser Ala Val Gly Arg Leu Leu Asn Asp Val Met Thr Tyr Glu
690                 695                 700

Lys Glu Val Leu Thr Trp Thr Pro Asn Ser Val Leu Gln Ala Leu
705                 710                 715                 720

Ala Ala Ala Arg Gly Gly Glu Ser Pro Thr Pro Ser Pro Ala
            725                 730                 735

Cys Ala Glu Ala Ala Arg Gly Glu Val Arg Arg Ala Ile Gln Ala Ser
            740                 745                 750

Trp Arg Asp Leu His Arg Leu Val Phe Arg Asp Asp Gly Ser Ser
        755                 760                 765

Ile Val Pro Arg Ala Cys Arg Glu Leu Phe Trp Gly Thr Ala Lys Val
    770                 775                 780

Ala Asn Val Phe Tyr Gln Glu Val Asp Gly Tyr Thr Pro Lys Ala Met
785                 790                 795                 800

Arg Gly Met Ala Asn Ala Val Ile Leu Asp Pro Leu His Leu Gln Gln
            805                 810                 815
```

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104
<211> LENGTH: 18
<212> TYPE: PRT
<213> ORGANISM: Salvia sclarea

<400> SEQUENCE: 104

```
Arg Leu Ala Phe Ala Lys Thr Ser Val Leu Val Thr Ile Met Asp Asp
1               5                   10                  15

Phe Phe
```

<210> SEQ ID NO 105

<400> SEQUENCE: 105

000

<210> SEQ ID NO 106
<211> LENGTH: 745
<212> TYPE: PRT
<213> ORGANISM: Cucumis sativus

<400> SEQUENCE: 106

| | | | | | | | | | | | | | | |
|---|---|---|---|---|---|---|---|---|---|---|---|---|---|---|
| Met | Asn | Leu | Ser | Arg | Pro | Thr | Asn | Leu | Gly | Cys | Phe | Thr | Ala | Ser | Ser |
| 1 | | | | 5 | | | | | 10 | | | | | 15 | |
| Ser | Ala | Ser | Leu | Phe | Pro | Gly | Leu | Asp | Val | Gly | Thr | Lys | Thr | Lys | Thr |
| | | | 20 | | | | | 25 | | | | | 30 | | |
| Gly | Ala | Leu | Arg | Phe | Glu | Glu | Thr | Lys | Glu | Arg | Ile | Lys | Lys | Leu | Phe |
| | | | 35 | | | | 40 | | | | | 45 | | | |
| Lys | Asn | Val | Glu | Leu | Ser | Val | Ser | Thr | Tyr | Asp | Thr | Ala | Trp | Val | Ala |
| 50 | | | | | 55 | | | | | 60 | | | | | |
| Met | Val | Pro | Ser | Pro | Thr | Ser | Leu | Asn | Lys | Pro | Leu | Phe | Pro | Glu | Cys |
| 65 | | | | | 70 | | | | | 75 | | | | | 80 |
| Ile | Asn | Trp | Val | Leu | Asp | His | Gln | Asn | Pro | Asp | Gly | Ser | Trp | Gly | Ile |
| | | | | 85 | | | | | 90 | | | | | 95 | |
| Leu | His | Asp | His | Gln | Leu | Val | Met | Lys | Ala | Thr | Leu | Leu | Ser | Thr | Leu |
| | | | 100 | | | | | 105 | | | | | 110 | | |
| Ala | Cys | Val | Leu | Thr | Leu | Lys | Arg | Trp | Asp | Ile | Gly | Asp | Asp | His | Met |
| | | | 115 | | | | | 120 | | | | | 125 | | |
| Ser | Lys | Ala | Leu | Ser | Phe | Ile | Lys | Ser | Asn | Ile | Ala | Ser | Ala | Thr | Asp |
| | 130 | | | | | 135 | | | | | 140 | | | | |
| Glu | Asn | Gln | Arg | Ser | Pro | Val | Gly | Phe | Asp | Ile | Ile | Phe | Pro | Gly | Met |
| 145 | | | | | 150 | | | | | 155 | | | | | 160 |
| Ile | Glu | Tyr | Ala | Lys | Asp | Leu | Asn | Leu | Asn | Leu | Pro | Leu | Ala | Ser | Met |
| | | | | 165 | | | | | 170 | | | | | 175 | |
| Asn | Val | Asp | Ala | Leu | Val | Gln | Lys | Lys | Glu | Leu | Glu | Leu | Arg | Ser | Cys |
| | | | 180 | | | | | 185 | | | | | 190 | | |
| Cys | Ser | Asn | Ser | Glu | Gly | Gly | Lys | Ala | Tyr | Leu | Ala | Tyr | Val | Ser | Glu |
| | | | 195 | | | | | 200 | | | | | 205 | | |
| Gly | Ile | Gly | Lys | Leu | Gln | Asp | Trp | Glu | Met | Val | Met | Arg | Tyr | Gln | Arg |
| | 210 | | | | | 215 | | | | | 220 | | | | |
| Lys | Asn | Gly | Ser | Leu | Phe | Ser | Ser | Pro | Ser | Thr | Thr | Ala | Val | Ala | Phe |
| 225 | | | | | 230 | | | | | 235 | | | | | 240 |
| Met | His | Arg | Asn | Asp | Asp | Gly | Cys | Phe | Asn | Tyr | Leu | Arg | Ser | Val | Leu |
| | | | | 245 | | | | | 250 | | | | | 255 | |
| Gln | Lys | Phe | His | Ser | Ser | Val | Pro | Ala | Ile | Tyr | Pro | Leu | Asp | Ile | Tyr |
| | | | 260 | | | | | 265 | | | | | 270 | | |
| Ala | Arg | Leu | His | Met | Val | Asp | Ser | Leu | Gln | Lys | Leu | Gly | Ile | Asp | Gly |
| | | | 275 | | | | | 280 | | | | | 285 | | |
| His | Phe | Lys | Asp | Glu | Ile | Arg | Ser | Val | Leu | Asp | Glu | Thr | Tyr | Ser | Cys |
| | 290 | | | | | 295 | | | | | 300 | | | | |
| Trp | Met | Gln | Gly | Glu | Glu | Asn | Ile | Phe | Leu | Asp | Ala | Ser | Thr | Cys | Ala |
| 305 | | | | | 310 | | | | | 315 | | | | | 320 |
| Met | Ala | Phe | Arg | Met | Leu | Arg | Val | Glu | Gly | Tyr | Asp | Val | Ser | Ser | Asp |
| | | | | 325 | | | | | 330 | | | | | 335 | |
| Gln | Leu | Thr | Gln | Phe | Ser | Glu | Gly | Leu | Phe | Ser | Asn | Cys | Leu | Gly | Gly |
| | | | 340 | | | | | 345 | | | | | 350 | | |
| His | Leu | Lys | Asp | Phe | Ser | Ala | Ser | Leu | Glu | Leu | Phe | Lys | Ala | Ser | Gln |
| | | | 355 | | | | | 360 | | | | | 365 | | |
| Ile | Ile | Ile | Tyr | Pro | Asp | Glu | Phe | Ile | Leu | Glu | Asn | Ile | Asn | Ser | Trp |
| | 370 | | | | | 375 | | | | | 380 | | | | |

```
Thr Ser Arg Phe Leu Asn His Gly Leu Ser Ser Gly Ser Val His Ser
385                 390                 395                 400

Asp Arg Thr Glu Arg Leu Val Lys Gln Glu Ala Val Asn Ala Phe Glu
            405                 410                 415

Phe Pro Tyr Asn Ser Thr Leu Glu Arg Leu Ser Asn Lys Arg Ala Leu
        420                 425                 430

Glu Ser Tyr Ser Gly Asp Ile Val Arg Ile Ser Lys Thr Ala Tyr Ala
    435                 440                 445

Cys Leu Asn Phe Gly His Gln Asp Phe Leu Glu Leu Ala Val Glu Asp
450                 455                 460

Phe Asn Thr Leu Gln Gly Ile His Arg Lys Leu Lys Glu Leu Glu
465                 470                 475                 480

Lys Trp Val Ile Glu Asn Lys Leu Asp Lys Leu Lys Phe Ala Arg Gln
                485                 490                 495

Lys Leu Ala Tyr Cys Tyr Phe Ser Ala Ala Ala Thr Leu Thr Ser Pro
            500                 505                 510

Glu Leu Cys Asp Ala Arg Leu Ser Trp Ala Lys Asn Gly Val Leu Thr
        515                 520                 525

Thr Val Val Asp Asp Phe Phe Asp Val Gly Gly Ser Glu Glu Glu Leu
530                 535                 540

Val Asn Leu Ile Gln Leu Val Glu Lys Trp Asp Ala Ser Gly Glu Thr
545                 550                 555                 560

Gly Tyr Cys Ser Lys Glu Val Glu Ile Ile Phe Leu Ala Leu His Ser
                565                 570                 575

Thr Ile Cys Glu Ile Gly Lys Lys Ala Leu Pro Trp Gln Gly Arg Ser
            580                 585                 590

Val Met Arg Asn Val Ile Asp Ile Trp Leu Ala Leu Leu Glu Ser Met
        595                 600                 605

Arg Lys Glu Ala Glu Trp Leu Lys Asn Lys Val Val Pro Ser Leu Asp
610                 615                 620

Glu Tyr Leu Met Ser Thr Ser Gly Arg Leu Leu Asn Asp Thr Arg Thr
625                 630                 635                 640

Phe Asp Arg Glu Ser Ser Glu Gly Lys Leu Asn Ala Leu Ser Leu Tyr
                645                 650                 655

Met Ile Ser Ala Gly Gly Lys Leu Thr Lys Glu Glu Ala Thr Glu Ala
            660                 665                 670

Met Lys Gly Asp Val Asp Arg Thr Arg Glu Leu Leu Arg Leu Val
        675                 680                 685

Leu Gln Glu Asn Ser Thr Ile Pro Arg Ala Cys Lys Asp Leu Phe Trp
690                 695                 700

Lys Met Ser Cys Val Val His Leu Phe Tyr Arg Lys Asp Asp Gly Phe
705                 710                 715                 720

Thr Ser His Glu Leu Met Asn Ser Ala Lys Ala Leu Phe Glu Gln Pro
                725                 730                 735

Met Val Leu Asp Glu Leu Leu Asn Lys
            740                 745

<210> SEQ ID NO 107
<211> LENGTH: 759
<212> TYPE: PRT
<213> ORGANISM: Nicotiana tabacum

<400> SEQUENCE: 107

Met Glu Glu Ala Lys Glu Arg Ile Arg Glu Thr Phe Gly Lys Ile Glu
1               5                   10                  15
```

-continued

```
Leu Ser Pro Ser Ser Tyr Asp Thr Ala Trp Val Ala Met Val Pro Ser
         20                  25                  30
Arg Tyr Ser Met Asn Gln Pro Cys Phe Pro Gln Cys Leu Asp Trp Ile
             35                  40                  45
Leu Glu Asn Gln Arg Glu Asp Gly Ser Trp Gly Leu Asn Pro Ser His
 50                  55                  60
Pro Leu Val Lys Asp Ser Leu Ser Ser Thr Leu Ala Ser Leu Leu
 65                  70                  75                  80
Ala Leu Arg Lys Trp Arg Ile Gly Asp Asn Gln Val Gln Arg Gly Leu
                 85                  90                  95
Gly Phe Ile Glu Thr His Gly Trp Ala Val Asp Asn Lys Asp Gln Ile
                100                 105                 110
Ser Pro Leu Gly Phe Glu Ile Ile Phe Pro Cys Met Thr Asn Tyr Ala
            115                 120                 125
Glu Lys Leu Asn Leu Asp Leu Pro Leu Asp Pro Asn Leu Val Asn Met
        130                 135                 140
Met Leu Cys Glu Arg Glu Leu Thr Ile Glu Arg Ala Leu Lys Asn Glu
145                 150                 155                 160
Phe Glu Gly Asn Met Ala Asn Val Glu Tyr Phe Ala Glu Gly Leu Gly
                165                 170                 175
Glu Ser Cys His Trp Lys Glu Met Met Leu Arg Gln Arg His Asn Gly
            180                 185                 190
Ser Leu Phe Asp Ser Pro Ala Thr Thr Ala Ala Ala Leu Ile Tyr His
            195                 200                 205
Gln Tyr Asp Glu Lys Cys Phe Gly Tyr Leu Asn Ser Ile Leu Lys Leu
    210                 215                 220
His Asp Asn Trp Val His Thr Ile Cys Pro Thr Lys Ile His Ser Asn
225                 230                 235                 240
Leu Phe Leu Val Asp Ala Leu Gln Asn Leu Gly Val Asp Arg Tyr Phe
                245                 250                 255
Lys Thr Glu Val Lys Arg Val Leu Asp Glu Ile Tyr Arg Leu Trp Leu
            260                 265                 270
Glu Lys Asn Glu Glu Ile Phe Ser Asp Val Ala His Cys Ala Met Ala
        275                 280                 285
Phe Arg Leu Leu Arg Met Asn Asn Tyr Glu Val Ser Ser Glu Glu Leu
290                 295                 300
Glu Gly Phe Val Asp Gln Glu His Phe Phe Thr Thr Ser Ser Gly Lys
305                 310                 315                 320
Leu Met Asn His Val Ala Ile Leu Glu Leu His Arg Ala Ser Gln Val
                325                 330                 335
Ala Ile His Glu Arg Lys Asp His Ile Leu Asp Lys Ile Ser Thr Trp
            340                 345                 350
Thr Arg Asn Phe Met Glu Gln Lys Leu Leu Asp Lys His Ile Pro Asp
        355                 360                 365
Arg Ser Lys Lys Glu Met Glu Phe Ala Met Arg Lys Phe Tyr Gly Thr
    370                 375                 380
Phe Asp Arg Val Glu Thr Arg Arg Tyr Ile Glu Ser Tyr Lys Met Asp
385                 390                 395                 400
Ser Phe Lys Ile Leu Lys Ala Ala Tyr Arg Ser Ser Gly Ile Asn Asn
                405                 410                 415
Ile Asp Leu Leu Lys Phe Ser Glu His Asp Phe Asn Leu Cys Gln Thr
            420                 425                 430
Arg His Lys Glu Glu Leu Gln Gln Met Lys Arg Trp Phe Thr Asp Cys
        435                 440                 445
```

Lys Leu Glu Gln Val Gly Leu Ser Gln Gln Tyr Leu Tyr Thr Ser Tyr
        450                 455                 460

Phe Ile Ile Ala Ala Ile Leu Phe Glu Pro Glu Tyr Ala Asp Ala Arg
465                 470                 475                 480

Leu Ala Tyr Ala Lys Tyr Ala Ile Ile Thr Ala Val Asp Asp Phe
                485                 490                 495

Phe Asp Cys Phe Ile Cys Lys Glu Glu Leu Gln Asn Ile Ile Glu Leu
                500                 505                 510

Val Glu Arg Trp Glu Gly Tyr Ser Thr Val Gly Phe Arg Ser Glu Arg
            515                 520                 525

Val Arg Ile Phe Phe Leu Ala Leu Tyr Lys Met Val Glu Glu Ile Ala
        530                 535                 540

Ala Lys Ala Glu Thr Lys Gln Gly Arg Cys Val Lys Asp His Leu Ile
545                 550                 555                 560

Asn Leu Trp Ile Asp Met Leu Lys Cys Met Leu Val Glu Leu Asp Leu
                565                 570                 575

Trp Lys Ile Lys Ser Thr Thr Pro Ser Ile Glu Glu Tyr Leu Ser Val
            580                 585                 590

Ala Cys Val Thr Ile Gly Val Pro Cys Phe Val Leu Thr Ser Leu Tyr
        595                 600                 605

Leu Leu Gly Pro Lys Leu Ser Lys Asp Val Ile Glu Ser Ser Glu Val
        610                 615                 620

Ser Ala Leu Cys Asn Cys Thr Ala Ala Val Ala Arg Leu Ile Asn Asp
625                 630                 635                 640

Ile His Ser Tyr Lys Arg Glu Gln Ala Glu Ser Ser Thr Asn Met Val
                645                 650                 655

Ser Ile Leu Ile Thr Gln Ser Gln Gly Thr Ile Ser Glu Glu Ala
            660                 665                 670

Ile Arg Gln Ile Lys Glu Met Met Glu Ser Lys Arg Arg Glu Leu Leu
            675                 680                 685

Gly Met Val Leu Gln Asn Lys Glu Ser Gln Leu Pro Gln Val Cys Lys
    690                 695                 700

Asp Leu Phe Trp Thr Thr Ile Asn Ala Ala Ala Tyr Ser Ile His Thr
705                 710                 715                 720

His Gly Arg Trp Val Ser Leu Pro Arg Gly Ile Gln Glu Pro Tyr Gln
                725                 730                 735

Arg Cys Asn Leu Gln Thr Thr Gln Ser Ile Phe Pro Ile Ile Cys Leu
            740                 745                 750

Lys Ser Phe Thr Ile Cys Tyr
        755

<210> SEQ ID NO 108
<211> LENGTH: 830
<212> TYPE: PRT
<213> ORGANISM: Oryza sativa

<400> SEQUENCE: 108

Met Met Leu Leu Gly Ser Pro Ser Gly Tyr Gly Gly Lys Phe
1               5                   10                  15

Ala Gly Ala Ser Pro Ala Gly Gly Thr Thr Met Ala Pro Ser Ala
                20                  25                  30

Lys Gln Pro Ser Ser Arg Ala Pro Pro Gly Ile Thr Gly Gly Arg
            35                  40                  45

Asn Asp Leu Arg Ile Leu Ser Pro Ala Ala Ala Ala Ala Val Gly
        50                  55                  60

-continued

```
Gly Leu Glu Met Lys Lys Pro Glu Ala Glu Gly Ile Ala Glu Ser Leu
 65                  70                  75                  80

Gln Ala Thr His Arg Lys Glu Leu Glu Ala Ser Ile Arg Lys Gln Leu
                 85                  90                  95

Gln Gly Val Glu Leu Ser Pro Ser Pro Tyr Asp Thr Ala Trp Val Ala
            100                 105                 110

Met Val Pro Leu Arg Gly Ser Ser His Asn Pro Ser Phe Pro Gln Cys
        115                 120                 125

Val Asp Trp Ile Leu Glu Asn Gln Trp Asp Asp Gly Ser Trp Ser Ile
    130                 135                 140

Asp Gly Ser Ile Ser Thr Ala Asn Lys Asp Val Leu Ser Ser Thr Leu
145                 150                 155                 160

Ala Cys Val Leu Ala Leu Asn Lys Trp Asn Val Gly Arg Glu His Ile
                165                 170                 175

Arg Arg Gly Leu Ser Phe Ile Gly Arg Asn Phe Ser Ile Ala Met Asp
            180                 185                 190

Asp Gln Ala Val Ala Pro Ile Gly Phe Gly Ile Thr Phe Pro Ala Met
        195                 200                 205

Leu Thr Leu Ala Asn Gly Ser Gly Leu Glu Val Pro Val Arg Gln Asn
    210                 215                 220

Asp Ile Asp Ser Leu Asn His Leu Arg Glu Met Lys Ile Gln Arg Glu
225                 230                 235                 240

Ala Gly Asn His Ser Arg Gly Arg Lys Ala Tyr Met Ala Tyr Leu Ala
                245                 250                 255

Glu Gly Phe Gly Asn Leu Leu Glu Trp Asp Glu Ile Met Met Phe Gln
            260                 265                 270

Arg Lys Asn Gly Ser Leu Phe Asn Cys Pro Ser Ser Thr Ala Gly Ala
        275                 280                 285

Leu Ala Asn Tyr His Asp Asp Lys Ala Leu Gln Tyr Leu Gln Ser Leu
    290                 295                 300

Val Asn Lys Phe Asp Gly Val Val Pro Thr Leu Tyr Pro Leu Asn Ile
305                 310                 315                 320

Tyr Cys Gln Leu Ser Met Val Asp Ala Leu Glu Asn Met Gly Ile Ser
                325                 330                 335

Gln Tyr Phe Ala Ser Glu Ile Lys Ser Ile Leu Asp Met Thr Tyr Ser
            340                 345                 350

Ser Trp Leu Gly Arg Asp Glu Glu Ile Met Leu Asp Val Thr Thr Cys
        355                 360                 365

Ala Met Ala Phe Arg Leu Leu Arg Met Asn Gly Tyr Asp Val Ser Ser
    370                 375                 380

Asp Glu Leu Ser His Val Ala Gly Ala Ser Gly Phe Arg Asp Ser Leu
385                 390                 395                 400

Gln Gly Tyr Leu Asn Asp Arg Lys Ser Val Leu Glu Val Tyr Lys Thr
                405                 410                 415

Ser Lys His Ser Ile Ser Glu Asn Asp Leu Ile Leu Asp Ser Ile Gly
            420                 425                 430

Ser Trp Ser Gly Ser Leu Leu Lys Glu Met Leu Cys Ser Asn Gly Ile
        435                 440                 445

Gln Gly Thr Pro Gly Arg Glu Glu Ile Glu Phe Ala Leu Lys Tyr Pro
    450                 455                 460

Phe Tyr Ser Thr Leu Glu Arg Leu Val His Arg Lys Asn Ile Val Leu
465                 470                 475                 480
```

```
Phe Asp Ala Lys Gly Ser Gln Met Leu Lys Thr Glu Cys Met Pro Val
            485                 490                 495
His Asp Ser Gln Asp Phe Leu Ala Leu Ala Val Asp Asp Phe Cys Ile
        500                 505                 510
Ser Gln Ser Asn Tyr Gln Asn Glu Leu Asn Tyr Leu Glu Ser Trp Val
    515                 520                 525
Lys Asp Asn Arg Leu Asp Gln Leu His Phe Ala Arg Gln Lys Ile Thr
530                 535                 540
Tyr Cys Tyr Leu Ser Gly Ala Ala Thr Thr Phe Arg Pro Glu Met Gly
545                 550                 555                 560
Tyr Ala Arg Thr Ser Trp Ala Arg Thr Ala Trp Leu Thr Ala Val Ile
                565                 570                 575
Asp Asp Leu Phe Asp Val Gly Gly Leu Glu Gln Glu Gln Glu Asn Leu
            580                 585                 590
Leu Ala Leu Met Glu Lys Trp Glu Glu Pro Gly Glu Asp Glu Tyr Tyr
        595                 600                 605
Ser Glu Asp Val Lys Ile Val Phe Gln Ala Leu Tyr Asn Thr Val Asn
    610                 615                 620
Glu Ile Gly Ala Lys Ala Ser Ala Leu Gln Gly His Asp Val Thr Lys
625                 630                 635                 640
Tyr Leu Val Asp Val Trp Leu His Val Val Arg Cys Met Lys Val Glu
                645                 650                 655
Ala Glu Trp Gln Arg Ser Gln His Leu Pro Thr Phe Glu Glu Tyr Met
            660                 665                 670
Glu Ser Gly Met Val Ser Leu Gly Gln Gly Ala Thr Val Met Ser Ala
        675                 680                 685
Leu Phe Leu Ile Gly Glu Lys Leu Pro Glu Gly Val Val Glu Leu Glu
    690                 695                 700
Glu Tyr Asp Glu Met Phe Arg Leu Met Gly Thr Cys Gly Arg Leu Leu
705                 710                 715                 720
Asn Asp Ile Arg Gly Ile Glu Arg Glu Glu Ser Asp Gly Lys Met Thr
                725                 730                 735
Asn Gly Val Ser Leu Leu Val His Ala Ser Gly Gly Ser Met Ser Val
            740                 745                 750
Asp Glu Ala Lys Thr Glu Val Met Lys Arg Ile Asp Ala Ser Arg Arg
        755                 760                 765
Lys Leu Leu Ser Leu Val Val Gly Glu Gln Glu Gly Pro Ile Pro Arg
    770                 775                 780
Pro Cys Lys Gln Leu Phe Trp Lys Met Cys Lys Ile Leu His Leu Phe
785                 790                 795                 800
Tyr Tyr Gln Thr Asp Gly Phe Ser Ser Pro Lys Glu Met Val Ser Ala
                805                 810                 815
Val Asp Ala Val Ile Lys Glu Pro Leu Gln Leu Arg Leu Leu
            820                 825                 830

<210> SEQ ID NO 109
<211> LENGTH: 738
<212> TYPE: PRT
<213> ORGANISM: Vitis vinifera

<400> SEQUENCE: 109

Met Phe Asp Lys Val Glu Leu Ser Val Ser Ser Tyr Asp Thr Ala Trp
1               5                   10                  15
Val Ala Met Val Pro Ser Pro Tyr Ser Ser Gln Ala Pro Tyr Phe Pro
            20                  25                  30
```

-continued

```
Glu Cys Val Asn Trp Leu Leu Glu Asn Gln Ser His Asp Gly Ser Trp
         35                  40                  45
Gly Leu Pro His Pro His Pro Met Leu Val Lys Asp Ala Leu Ser Ser
 50                  55                  60
Thr Leu Ala Ser Val Leu Ala Leu Lys Arg Trp Gly Val Gly Glu Glu
 65                  70                  75                  80
Gln Arg Asn Lys Gly Leu Trp Phe Ile Ala Ser Asn Phe Ala Ser Val
             85                  90                  95
Ser Asp Glu Lys Gln His Ser Pro Ile Gly Phe Asp Ile Ile Phe Pro
            100                 105                 110
Gly Met Ile Glu Tyr Ala Lys Glu Leu Asp Leu Asn Leu Pro Leu Gly
            115                 120                 125
Gln Arg Asp Val Asp Ala Met Leu Gln Lys Arg Asp Leu Glu Leu Lys
130                 135                 140
Gly Ser Leu Gly Ser Asn Thr Lys Ser Arg Glu Ala Tyr Leu Ala Tyr
145                 150                 155                 160
Ile Ser Glu Gly Met Gly Arg Leu Gln Asp Trp Glu Met Val Met Lys
                165                 170                 175
Tyr Gln Met Lys Asn Gly Ser Leu Leu Asn Ser Pro Ser Ala Thr Ala
            180                 185                 190
Ala Ala Leu Ser His Leu Gln Asn Ala Gly Cys Leu Asn Tyr Leu Arg
        195                 200                 205
Ser Leu Leu Glu Lys Phe Gly Asn Ala Val Pro Thr Val Tyr Pro Leu
210                 215                 220
Asp Leu Tyr Ala Arg Leu Cys Leu Val Asp Asn Leu Glu Arg Leu Gly
225                 230                 235                 240
Ile Asp Arg Tyr Phe Arg Met Glu Ile Arg Ser Val Leu Asp Glu Thr
                245                 250                 255
Tyr Arg Cys Trp Leu Gln Arg Glu Glu Glu Ile Phe Ala Asp Arg Ala
            260                 265                 270
Thr Cys Ala Ile Ala Phe Arg Ile Leu Arg Leu Asn Gly Tyr Asp Ile
        275                 280                 285
Ser Ser Val Pro Leu Ala Gln Phe Ala Glu Asp Gln Tyr Phe Lys
290                 295                 300
Phe Gly Gln Asp Phe Lys Asp Leu Gly Ala Ala Leu Glu Leu Phe Arg
305                 310                 315                 320
Ala Ser Glu Met Ile Ile His Pro Asp Glu Val Val Leu Glu Lys Gln
                325                 330                 335
Asn Ser Trp Ser Ser His Phe Leu Arg Gln Gly Leu Ser Asn Ser Ser
            340                 345                 350
Ile His Ala Asp Arg Leu Asn Lys Tyr Ile Ala Gln Glu Val Glu Asp
        355                 360                 365
Ala Leu Arg Phe Pro Tyr Tyr Ala Asn Leu Asp Arg Ile Ala Asn Arg
370                 375                 380
Arg Ser Ile Glu His Tyr Asn Val Asp Asp Thr Arg Ile Leu Lys Thr
385                 390                 395                 400
Ala Tyr Arg Ser Ser His Val Cys Asn Lys Asp Phe Leu Lys Leu Ala
                405                 410                 415
Val Glu Asp Phe Asn Phe Cys Gln Ser Ile His Gln Asn Glu Leu Lys
            420                 425                 430
Gln Leu Glu Arg Trp Ile Ile Glu Asn Arg Leu Asp Lys Leu Lys Phe
        435                 440                 445
Ala Arg Gln Lys Leu Ala Tyr Cys Tyr Phe Ser Ala Ala Ala Thr Ile
450                 455                 460
```

```
Phe Ser Pro Glu Gln Ser Asp Ala Arg Leu Ser Trp Ala Lys Asn Ser
465                 470                 475                 480

Val Leu Thr Thr Val Val Asp Phe Phe Asp Ile Gly Gly Ser Glu
        485                 490                 495

Glu Glu Leu Leu Asn Leu Ile Gln Leu Val Glu Lys Trp Asp Ile Asp
            500                 505                 510

Val Ala Val Asp Cys Cys Ser Glu Gln Val Glu Ile Val Phe Ser Ala
        515                 520                 525

Leu His Ser Thr Ile Ser Glu Ile Gly Val Lys Ala Ser Ala Trp Gln
        530                 535                 540

Ala Arg Asn Val Thr Ser His Ile Ile Asp Ile Trp Leu Lys Leu Leu
545                 550                 555                 560

Arg Ser Met Leu Gln Glu Ala Gln Trp Val Ser Asn Lys Ser Ala Pro
                565                 570                 575

Thr Met Asp Glu Tyr Met Thr Asn Ala Tyr Val Ser Phe Ala Leu Gly
                580                 585                 590

Pro Ile Val Leu Pro Ala Leu Tyr Phe Val Gly Pro Lys Leu Ser Glu
            595                 600                 605

Glu Val Val Glu Gly Pro Glu Cys His Lys Leu Tyr Lys Leu Met Ser
        610                 615                 620

Thr Cys Gly Arg Leu Leu Asn Asp Ile His Ser Phe Lys Arg Glu Ser
625                 630                 635                 640

Lys Glu Gly Lys Ala Asn Ala Leu Ala Leu His Met Ile His Gly Asn
                645                 650                 655

Gly Val Thr Thr Glu Glu Gln Ala Ile Arg Glu Met Lys Gly Leu Val
            660                 665                 670

Lys Ser Gln Arg Arg Glu Leu Gln Arg Leu Val Leu Glu Lys Gly
        675                 680                 685

Ser Thr Val Pro Arg Ile Cys Lys Asp Leu Phe Trp Lys Met Ser Lys
        690                 695                 700

Val Leu His Thr Phe Tyr Glu Lys Asp Asp Gly Phe Thr Ser His Asp
705                 710                 715                 720

Met Leu Arg Ala Val Lys Ser Val Ile Tyr Glu Pro Val Leu Leu Ala
                725                 730                 735

Glu Phe

<210> SEQ ID NO 110
<211> LENGTH: 788
<212> TYPE: PRT
<213> ORGANISM: Lactuca sativa

<400> SEQUENCE: 110

Met Asn Ile Ala Gln Ile Thr Ser Ser Ala Met Leu Val Pro Ser Ser
1               5                   10                  15

His Ile Pro His Arg Ser Trp Val Val Asn Cys Cys Met Val Gln Tyr
                20                  25                  30

Asn Pro Ser Gly Leu Arg Thr Ala Ser Ser Gln Ala Gly Gln Val Asn
            35                  40                  45

Pro Thr Val Met Thr Leu Asp Val Thr Lys Glu Arg Ile Arg Lys Leu
        50                  55                  60

Phe Asn Asn Val Glu Val Ser Val Ser Ser Tyr Asp Thr Ala Trp Val
65                  70                  75                  80

Ala Met Val Pro Ser Pro Asn Ser Pro Lys Ser Pro Cys Phe Pro Asp
                85                  90                  95
```

```
Cys Leu Asn Trp Leu Leu Asp Asn Gln Leu Asp Asp Gly Ser Trp Gly
                100                 105                 110
Leu Leu Pro His Gln Ser Pro Leu Ile Lys Asp Thr Leu Ser Ser Thr
            115                 120                 125
Leu Ala Cys Val Leu Ala Leu Lys Arg Trp Asn Val Gly Lys Asp Gln
        130                 135                 140
Ile Asn Lys Gly Leu His Tyr Ile Glu Ser Asn Phe Ala Ser Val Thr
145                 150                 155                 160
Asp Lys Asn Gln Ala Ser Pro Phe Gly Phe Asp Ile Ile Phe Pro Gly
                165                 170                 175
Met Leu Glu Tyr Ala Lys Asp Leu Asp Ile Lys Leu Pro Leu Asn Gln
            180                 185                 190
Thr His Leu Ser Val Met Leu His Glu Arg Glu Leu Glu Leu Arg Arg
        195                 200                 205
Cys His Ser Asn Gly Arg Glu Ala Tyr Leu Ala Tyr Ile Ser Glu Gly
        210                 215                 220
Leu Gly Asn Leu Asn Asp Trp Asn Met Val Met Lys Tyr Gln Met Lys
225                 230                 235                 240
Asn Gly Ser Leu Phe Asn Ser Pro Ser Ala Thr Ala Ser Val Leu Ile
                245                 250                 255
His His Gln Asn Ala Gly Cys Leu His Tyr Leu Thr Ser Leu Leu Asp
            260                 265                 270
Lys Phe Gly Asn Ala Val Pro Thr Val Tyr Pro Ile Asp Leu Tyr Val
        275                 280                 285
Arg Leu Ser Met Val Asp Thr Leu Glu Arg Leu Gly Ile Lys Arg His
        290                 295                 300
Phe Met Val Glu Ile Gln Asn Val Leu Asp Glu Thr Tyr Arg Cys Trp
305                 310                 315                 320
Val Gln Gly Asp Val Gln Ile Phe Met Asp Val Val Thr Cys Ala Leu
                325                 330                 335
Ala Phe Arg Val Leu Arg Ser Asn Gly Tyr Glu Val Ser Ser Asp Pro
            340                 345                 350
Leu Ala Lys Ile Thr Lys Glu Gly Asp Tyr Met Asn Ser Pro Glu Lys
        355                 360                 365
Pro Phe Lys Asp Val Tyr Thr Ser Leu Glu Val Tyr Lys Ala Ser Gln
        370                 375                 380
Ile Ile Tyr Gln Glu Glu Leu Ala Phe Arg Glu Gln Asn Leu Thr Ser
385                 390                 395                 400
Tyr Leu Pro Ser Ser Asn Lys Leu Ser Asn Tyr Ile Leu Lys Glu Val
                405                 410                 415
Asp Asp Ala Leu Lys Phe Pro Phe Asn Gly Ser Leu Glu Arg Met Ser
            420                 425                 430
Thr Arg Arg Asn Ile Glu His Tyr Asn Leu Asn His Thr Arg Ile Leu
        435                 440                 445
Lys Thr Thr Tyr Ser Ser Ser Asn Ile Ser Asn Lys Asp Tyr Leu Lys
        450                 455                 460
Leu Ala Val Gln Asp Phe Asn Glu Cys Gln Ser Ile Tyr Cys Glu Glu
465                 470                 475                 480
Leu Lys Asp Leu Glu Arg Trp Val Val Glu Asn Arg Leu Asp Lys Leu
                485                 490                 495
Lys Phe Ala Arg Gln Lys Thr Ala Tyr Cys Tyr Phe Ser Ala Ala Ser
            500                 505                 510
Phe Leu Ser Ser Pro Asp Leu Ser Asp Ala Arg Ile Ser Trp Ala Lys
        515                 520                 525
```

```
Ser Ser Ile Leu Thr Thr Val Ile Asp Asp Phe Phe Asp Val Gly Gly
        530                 535                 540

Ser Met Asp Glu Leu Val Asn Phe Val His Ile Ile Glu Lys Trp Asn
545                 550                 555                 560

Val Asn Val Glu Asn Asp Cys Cys Ser Glu Glu Val Gly Val Leu Phe
                565                 570                 575

Leu Ala Leu Lys Asp Ala Val Cys Trp Ile Gly Asp Lys Ala Phe Lys
            580                 585                 590

Ile Gln Glu Arg Asn Ile Thr Ser His Val Ile Glu Ile Trp Leu Asp
        595                 600                 605

Leu Val Lys Ser Met Leu Arg Glu Ala Ile Trp Ala Lys Asp Gly Ser
    610                 615                 620

Ile Pro Thr Ile Asn Glu Tyr Met Glu Asn Gly Tyr Val Ser Phe Ala
625                 630                 635                 640

Leu Gly Pro Ile Val Leu Pro Thr Leu Tyr Phe Leu Gly Val Lys Leu
                645                 650                 655

Ser Glu Glu Val Val Gln Ser Ser Gly Tyr His Lys Leu Tyr Glu Val
            660                 665                 670

Met Ser Thr Gln Gly Arg Leu Met Asn Asp Ile His Ser Phe Lys Arg
        675                 680                 685

Glu Lys Lys Ala Gly Lys Leu Asn Ala Val Ala Leu Tyr Met Ser Asp
    690                 695                 700

Gly Lys Ser Gly Ser Val Glu Glu Val Val Glu Glu Met Lys Ile
705                 710                 715                 720

Leu Thr Lys Ser Gln Arg Lys Glu Met Met Lys Leu Val Leu Glu Thr
                725                 730                 735

Lys Gly Ser Val Val Pro Arg Val Cys Lys Asp Val Phe Trp Asn Met
            740                 745                 750

Cys Asn Val Leu Asn Leu Phe Tyr Ala Thr Asp Asp Gly Phe Thr Gly
        755                 760                 765

Asn Ala Ile Leu Asp Val Val Lys Glu Ile Ile Tyr Glu Pro Val Ser
    770                 775                 780

His Glu Leu Ile
785

<210> SEQ ID NO 111
<211> LENGTH: 789
<212> TYPE: PRT
<213> ORGANISM: Cucurbita maxima

<400> SEQUENCE: 111

Met Tyr Leu Ser Arg Pro Thr Gly Val Ala Arg Phe Ala Ala Ser Ser
1               5                   10                  15

Ser Ser Ser Ser Ser Ala Ser Leu Phe Pro Gly Val Asp Val Asp Thr
                20                  25                  30

Thr Thr Lys Thr Gly Ala Leu His Phe Glu Glu Thr Lys Glu Arg Ile
            35                  40                  45

Lys Lys Leu Phe Asp Lys Val Glu Leu Ser Val Ser Ala Tyr Asp Thr
        50                  55                  60

Ala Trp Val Ala Met Val Pro Ser Pro Asn Ser Leu Asn Gln Pro Leu
65                  70                  75                  80

Phe Pro Glu Cys Ile Asn Trp Val Leu Asp Ser Gln His Ala Asp Gly
                85                  90                  95

Ser Trp Gly Leu Leu His Asn Asp Gln Leu Leu Met Lys Ala Asn Leu
            100                 105                 110
```

```
Leu Ser Thr Leu Ala Cys Val Leu Thr Leu Lys Arg Trp Asn Ile Gly
        115                 120                 125

His Asp His Met Ser Lys Ala Leu Asp Phe Ile Lys Ser Asn Ile Ala
    130                 135                 140

Ser Ala Thr Asp Glu Asn Gln Arg Ser Pro Val Gly Phe Asp Ile Ile
145                 150                 155                 160

Phe Pro Gly Met Ile Glu Tyr Ala Lys Asp Leu Asn Leu Asn Leu Pro
                165                 170                 175

Leu Ala Pro Thr Asn Val Asp Ala Leu Val Arg Lys Glu Leu Glu
            180                 185                 190

Leu Arg Ser Cys Arg Ser Asn Ser Glu Gly Gly Lys Ala Tyr Leu Ala
        195                 200                 205

Tyr Val Ser Glu Gly Ile Gly Lys Leu Gln Asp Trp Asp Met Val Met
    210                 215                 220

Gln Tyr Gln Arg Lys Asn Gly Ser Leu Phe Asn Ser Pro Ser Thr Thr
225                 230                 235                 240

Ala Ala Ala Phe Met His Arg Asn Asp Asp Gly Cys Phe Asp Tyr Leu
                245                 250                 255

Arg Ser Leu Leu Gln Lys Phe Asp Gly Ser Val Pro Thr Ile Tyr Pro
            260                 265                 270

Leu Asp Ile Tyr Ala Arg Leu His Met Val Asp Ser Leu Gln Lys Phe
        275                 280                 285

Gly Ile Ala Arg His Phe Lys Glu Glu Ile Arg Ser Val Leu Asp Glu
    290                 295                 300

Thr Tyr Arg Cys Trp Met Gln Gly Glu Glu Asn Ile Phe Leu Asp Ala
305                 310                 315                 320

Ser Thr Cys Ala Met Ala Phe Arg Met Leu Arg Val Glu Gly Tyr Asp
                325                 330                 335

Val Ser Ser Asp Gln Leu Thr Gln Phe Ser Glu Asp Ile Phe Pro Asn
            340                 345                 350

Cys Leu Gly Gly Tyr Leu Lys Asp Phe Gly Ala Ser Leu Glu Leu Tyr
        355                 360                 365

Lys Ala Ser Gln Ile Ile Thr His Pro Asp Glu Ser Val Leu Glu Asn
    370                 375                 380

Ile Asn Ser Trp Thr Ser Arg Phe Leu Lys His Gly Leu Ser Ser Asp
385                 390                 395                 400

Ser Val Trp Ser Asp Arg Thr Asp Ser Val Lys Gln Glu Ala Val
                405                 410                 415

Asn Ala Leu Glu Phe Pro Tyr Asn Ala Thr Leu Glu Arg Leu Ile Ser
            420                 425                 430

Lys Arg Ala Met Glu Ser Tyr Ser Gly Asp Ile Val Arg Ile Ser Lys
        435                 440                 445

Ser Pro Tyr Ala Cys Leu Asn Phe Gly His Gln Asp Phe Leu Glu Leu
    450                 455                 460

Ala Val Glu Asp Phe Asn Thr Leu Gln Arg Ile His Leu Lys Glu Leu
465                 470                 475                 480

Glu Glu Leu Gln Arg Trp Val Val Glu Asn Lys Leu Asp Glu Leu Lys
                485                 490                 495

Phe Phe Arg Leu His Leu Gly Tyr Cys Tyr Phe Ala Ala Ala Ala Thr
            500                 505                 510

Leu Thr Asp Pro Glu Leu His Asp Ala Arg Ile Ala Trp Ala Gln Asn
        515                 520                 525
```

-continued

```
Gly Val Leu Thr Thr Val Val Asp Asp Phe Tyr Asp Gly Gly Ser
            530             535             540

Glu Glu Glu Leu Asp Asn Leu Ile Glu Leu Val Glu Lys Trp Asp Pro
545             550             555             560

Asp Gly Glu Val Gly Tyr Cys Ser Lys Asp Val Glu Ile Val Phe Leu
                565             570             575

Ala Leu His Ser Thr Val Cys Glu Ile Gly Arg Arg Ala Leu Val Trp
            580             585             590

Gln Gly Arg Ser Val Met Arg Asn Val Ile Asp Gly Trp Leu Ala Leu
            595             600             605

Leu Lys Val Met Arg Lys Glu Ala Glu Trp Ser Thr Asn Lys Val Val
            610             615             620

Pro Ser Met Gly Glu Tyr Met Glu Gln Ala His Val Ser Phe Ala Leu
625             630             635             640

Gly Pro Ile Ile Leu Pro Met Leu Phe Phe Val Gly Pro Lys Leu Ser
                645             650             655

Glu Glu Met Ile Gly Ser Cys Glu Tyr Gln Lys Leu Tyr Lys Leu Met
            660             665             670

Ser Thr Ala Gly Arg Leu Lys Asn Asp Ile Arg Ser Tyr Asp Arg Glu
            675             680             685

Cys Lys Glu Gly Lys Leu Asn Ile Leu Ser Leu Trp Met Ile Asp Gly
    690             695             700

Gly Gly Asn Val Thr Lys Glu Glu Ala Ile Glu Ala Ile Lys Gly Asp
705             710             715             720

Phe Glu Arg Ala Ile Arg Glu Leu Leu Gly Leu Val Leu Gln Glu Asn
                725             730             735

Thr Thr Ile Pro Arg Ala Cys Lys Asp Leu Phe Trp Lys Leu Met Ser
            740             745             750

Ile Val Asn Leu Phe Tyr Met Glu Asp Asp Gly Tyr Thr Ser Asn Arg
            755             760             765

Leu Met Asn Thr Val Lys Ala Met Phe Glu Gln Pro Met Asp Leu Asp
    770             775             780

Ala Leu Leu Asn Lys
785
```